US011517615B2

(12) United States Patent
Crotty et al.

(10) Patent No.: US 11,517,615 B2
(45) Date of Patent: Dec. 6, 2022

(54) DIAGNOSIS AND TREATMENT OF INFECTION INVOLVING KILLER T FOLLICULAR HELPER CELLS, METHODS OF PREPARATION, AND USES THEREOF

(71) Applicant: LA JOLLA INSTITUTE FOR ALLERGY AND IMMUNOLOGY, La Jolla, CA (US)

(72) Inventors: Shane Crotty, San Diego, CA (US); Jennifer Dan, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 102 days.

(21) Appl. No.: 16/609,784

(22) PCT Filed: May 3, 2018

(86) PCT No.: PCT/US2018/030948
§ 371 (c)(1),
(2) Date: Oct. 31, 2019

(87) PCT Pub. No.: WO2018/204690
PCT Pub. Date: Nov. 8, 2018

(65) Prior Publication Data
US 2020/0061180 A1 Feb. 27, 2020

Related U.S. Application Data

(60) Provisional application No. 62/500,499, filed on May 3, 2017.

(51) Int. Cl.
| | |
|---|---|
| A61K 39/00 | (2006.01) |
| A61K 39/09 | (2006.01) |
| A61P 37/04 | (2006.01) |
| A61P 31/04 | (2006.01) |
| A61K 35/17 | (2015.01) |
| G01N 33/563 | (2006.01) |
| G01N 33/569 | (2006.01) |

(52) U.S. Cl.
CPC ............ *A61K 39/092* (2013.01); *A61K 35/17* (2013.01); *A61P 31/04* (2018.01); *A61P 37/04* (2018.01); *G01N 33/563* (2013.01); *G01N 33/56972* (2013.01); *G01N 33/56977* (2013.01); *G01N 2800/14* (2013.01); *G01N 2800/26* (2013.01); *G01N 2800/50* (2013.01); *G01N 2800/52* (2013.01)

(58) Field of Classification Search
CPC ........... G01N 2800/14; G01N 2800/50; G01N 33/56977; A61K 39/092
USPC ...... 424/9.1, 9.2, 184.1, 234.1, 236.1, 244.1
See application file for complete search history.

(56) References Cited

FOREIGN PATENT DOCUMENTS

WO 2018204690 A1 11/2018

OTHER PUBLICATIONS

Federal Institute of Industrial Property (ISA), International Search Report and Written Opinion for PCT/US2018/030948 dated Aug. 2, 2018, 12 pp.
Roggiani, et al. "Toxoids of Streptococcal Pyrogenic Exotoxin A Are Protective in Rabbit Models of Streptococcal Toxic Shock Syndrome" Infection and Immunity, Sep. 2000, pp. 5011-5017.
Wong, et al. "*Streptococcus pyogenes* and re-emergence of scarlet fever as a public health problem" Emerging Microbes and Infections (2012), published online Jul. 11, 2012.
Kasper, et al. "Bacterial Superantigens Promote Acute Nasopharyngeal Infection by *Streptococcus pyogenes* in a Human MHC Class II-Dependent Manner" PLOS Pathogens, May 2014, vol. 10, Issue 5, e1004155.
Forward, et al. "A comparison between the Strep A Rapid Test Device and conventional culture for the diagnosis ol streptococcal pharyngitis" Can J Infect Dis Med Microbiol, vol. 17, No. 4, Jul./Aug. 2006, pp. 221-223.
Dan, et al. "A Cytokine-Independent Approach To Identify Antigen-Specific Human Germinal Center T Follicular Helper Cells and Rare Antigen-Specific CD4+ T Cells in Blood" J Immunol 2016; 197:983-993; Prepublished online Jun. 24, 2016.
Crotty, Shane "T follicular helper cell differentiation, function, and roles in disease" Immunity. Oct. 16, 2014;41 (4):529-42. doi: 10.1016/j.immuni.2014.10.004.

*Primary Examiner* — Albert M Navarro
(74) *Attorney, Agent, or Firm* — Edwin S. Flores; Daniel J. Chalker; Chalker Flores, LLP

(57) ABSTRACT

Recurrent tonsillitis disease (RT) is a common indication for pediatric tonsillectomy, the most frequent childhood surgery. It is unknown why some children develop RT. The present disclosure demonstrates that RT tonsils exhibit significantly smaller germinal centers than non-RT tonsils, concomitant with a bias against Group A *Streptococcus* (GAS)-specific germinal center follicular helper CD4+ T cells (GC Tfh), and significantly reduced antibodies to the GAS virulence factor SpeA. The present disclosure also shows a significant immunogenetic component to this disease, with the identification of 'at risk' and 'protective' HLA alleles for RT. Finally, the present disclosure identifies a new cell type, granzyme B+GC Tfh cells, which are activated by SpeA, are significantly more abundant in RT GC Tfh cells, and have the capacity to kill B cells, thus, providing a window into the immunology and genetics of a classic childhood disease and identifies a new type of pathogenic T cell.

14 Claims, 32 Drawing Sheets

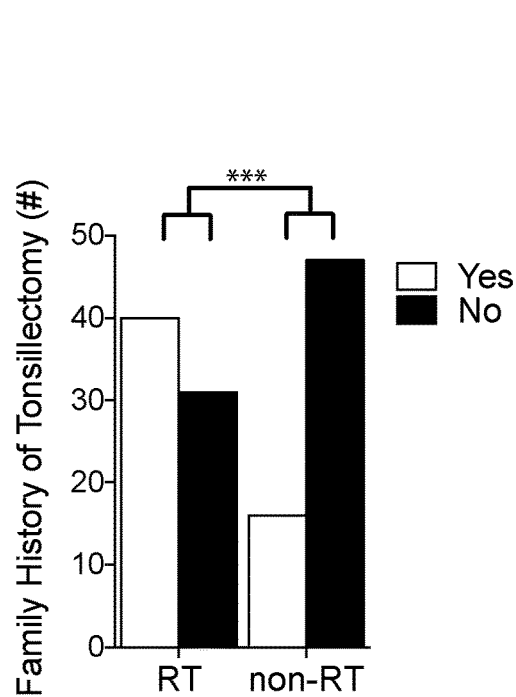
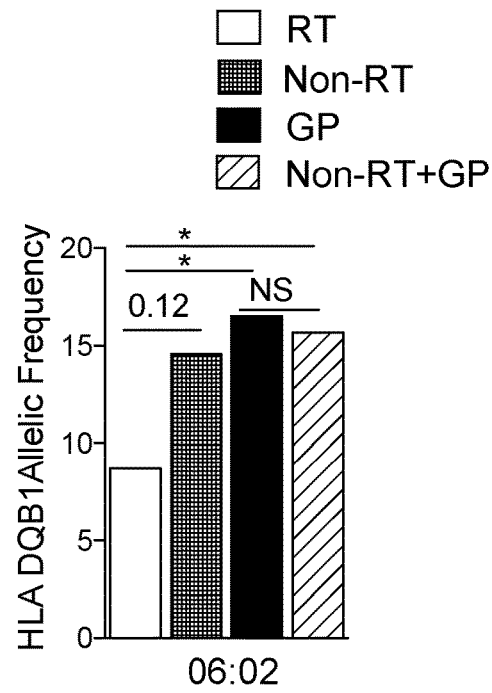
Figure 4A
Figure 4B
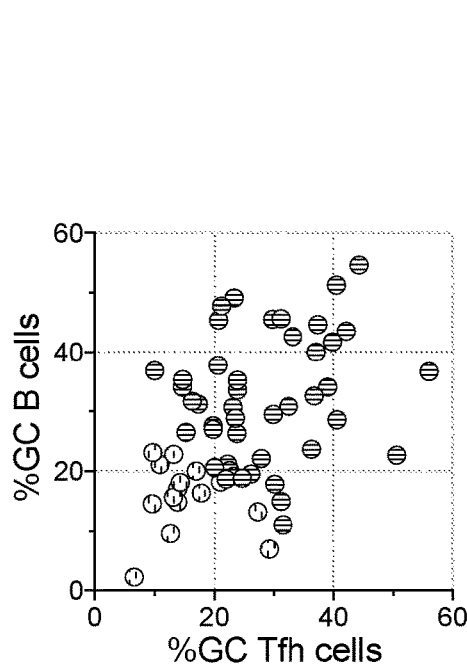
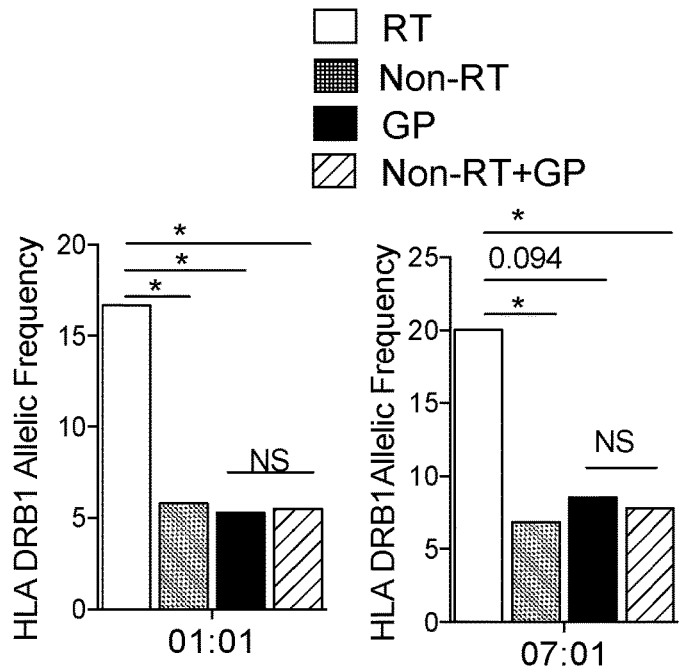
Figure 4C

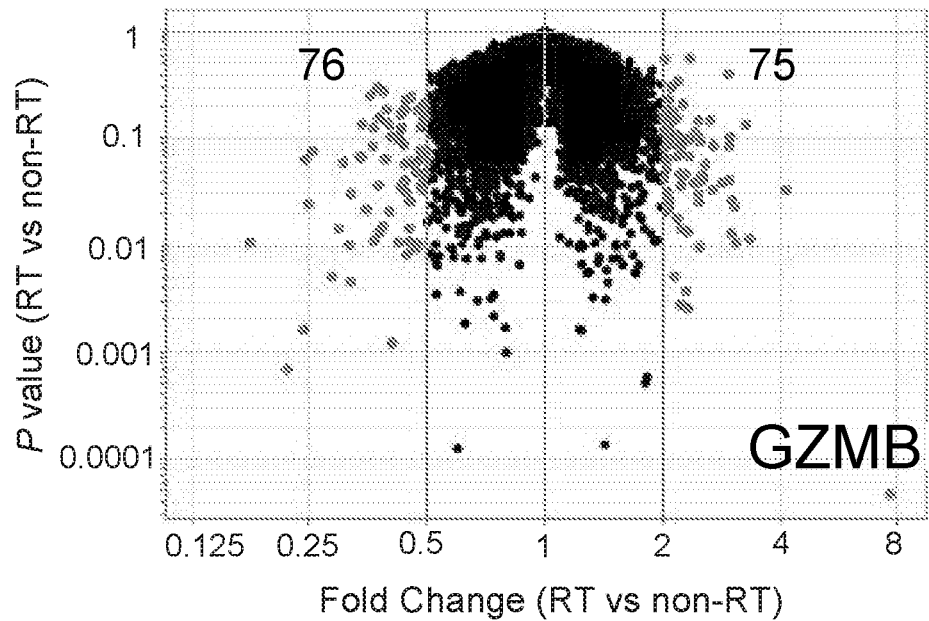
Figure 6A
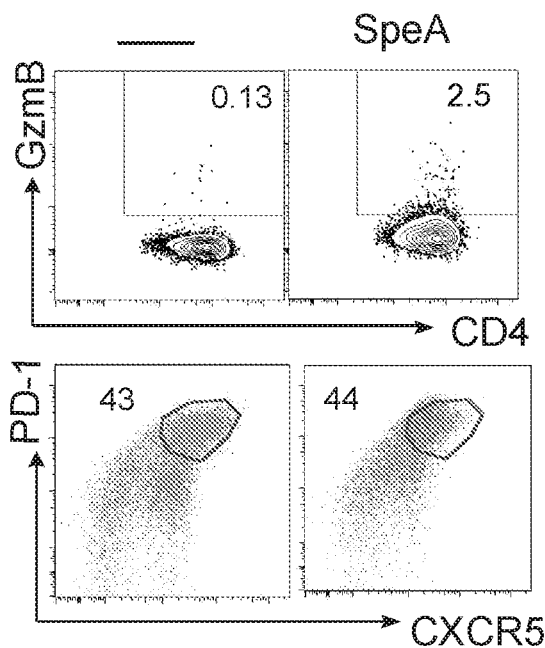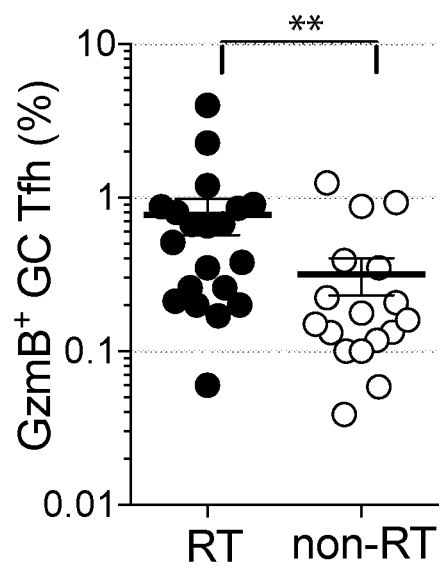
Figure 6B
Figure 6C

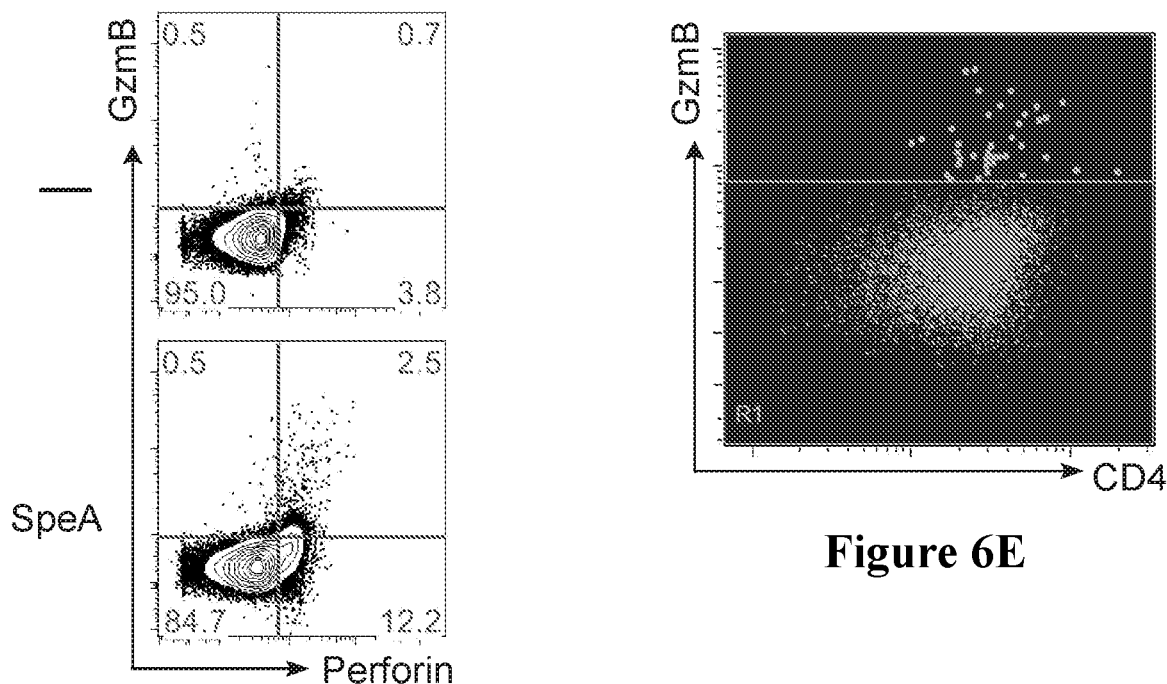
Figure 6D
Figure 6E
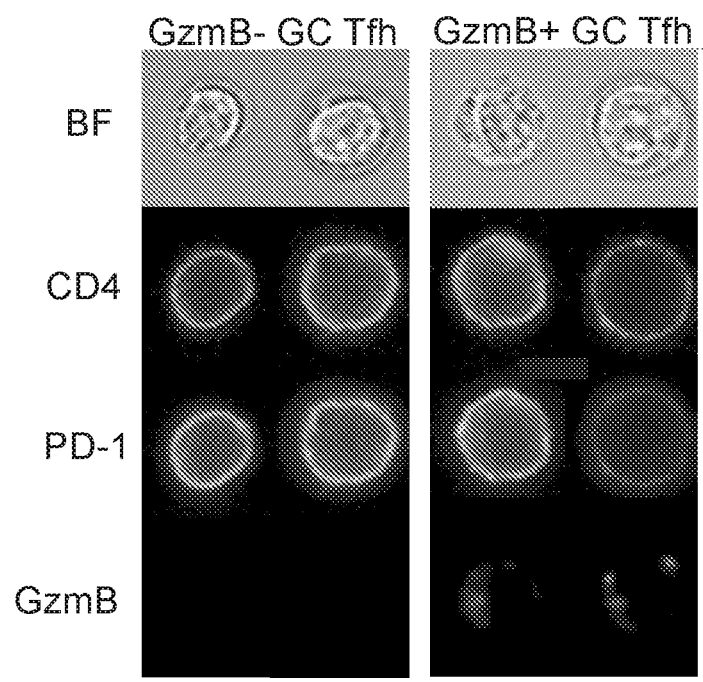
Figure 6F

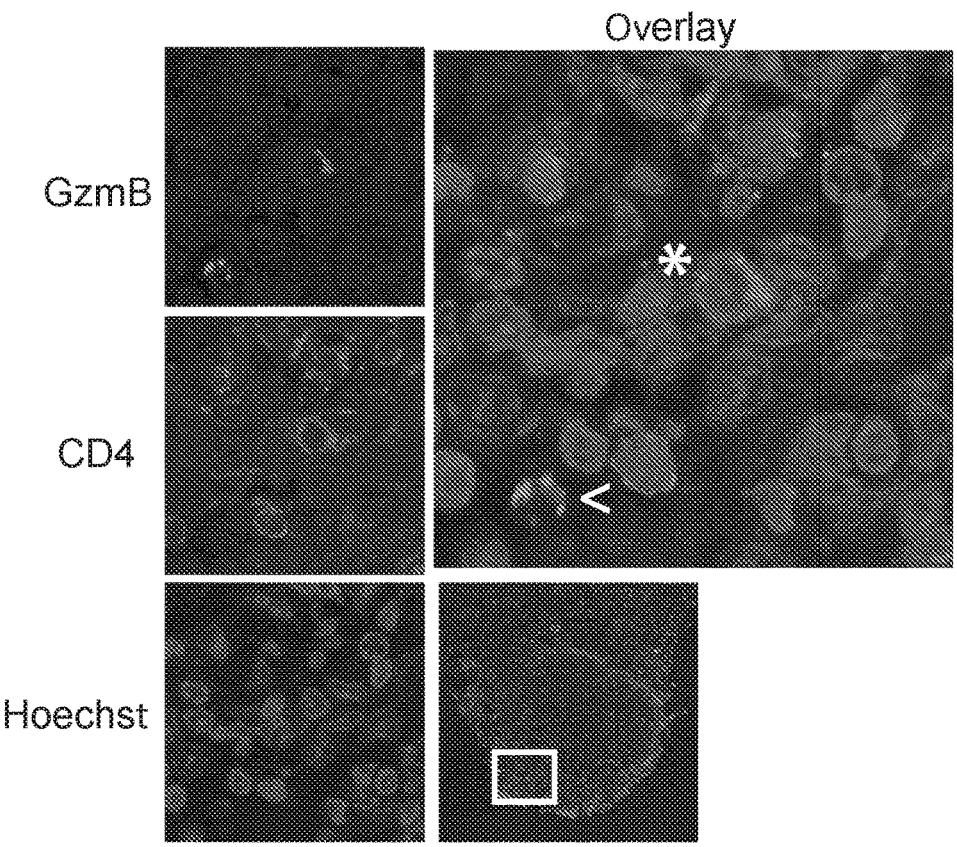
Figure 6G
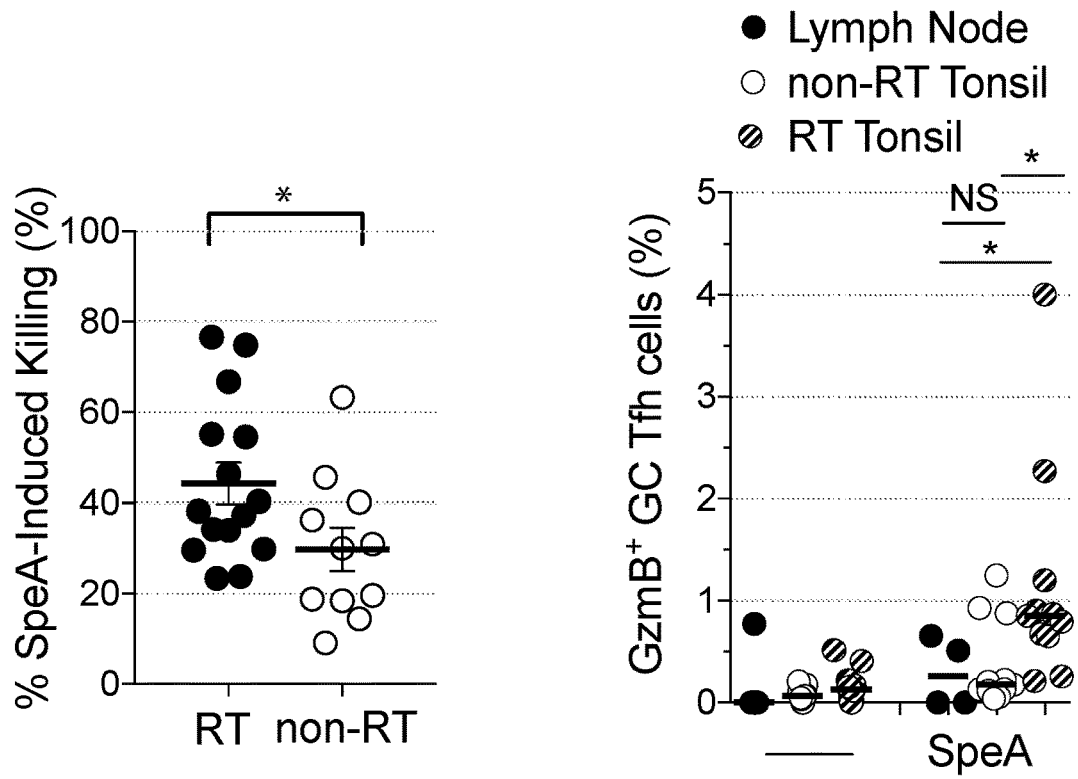
Figure 6H
Figure 6I

| HLA Allele | RT + | RT - | Non-RT + | Non-RT - | P | GP + | GP - | P | Non-RT+GP + | Non-RT+GP - | P |
|---|---|---|---|---|---|---|---|---|---|---|---|
| DQB1*06:02 | 12 | 126 | 28 | 164 | 0.12 | 40 | 202 | 0.042 | 68 | 366 | 0.048 |
| DRB1*01:01 | 13 | 125 | 11 | 179 | 0.28 | 13 | 233 | 0.14 | 24 | 412 | 0.11 |
| DRB1*07:01 | 11 | 127 | 13 | 177 | 0.83 | 21 | 225 | 1.00 | 34 | 402 | 1.00 |
| DRB1*01:01+GC$^{lo}$ | 5 | 25 | 11 | 179 | 0.049 | 13 | 233 | 0.034 | 24 | 412 | 0.031 |
| DRB1*07:01+GC$^{lo}$ | 6 | 24 | 13 | 177 | 0.029 | 21 | 225 | 0.094 | 34 | 402 | 0.034 |

Figure 9B

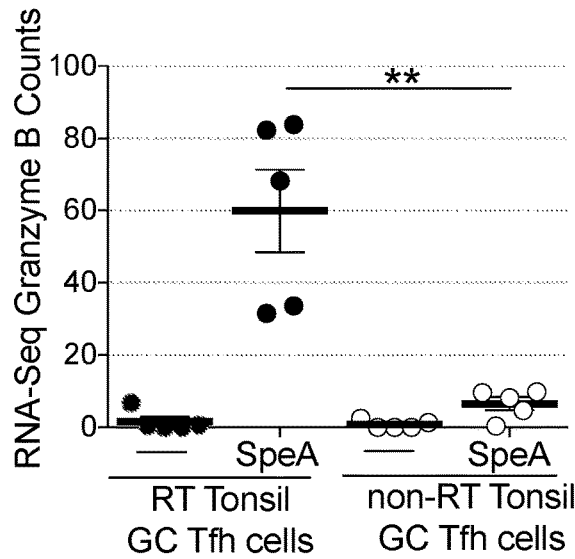
Figure 11B
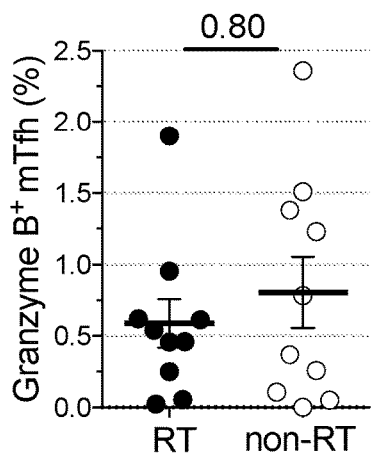 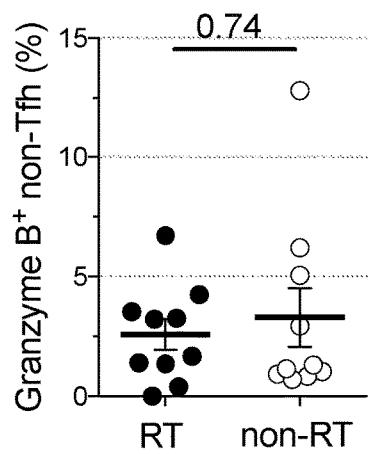 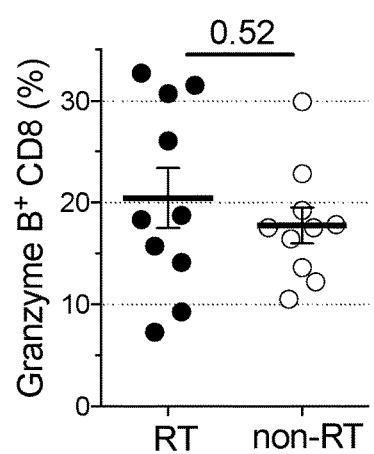
Figure 12A Figure 12B Figure 12C

DIAGNOSIS AND TREATMENT OF INFECTION INVOLVING KILLER T FOLLICULAR HELPER CELLS, METHODS OF PREPARATION, AND USES THEREOF

CROSS-REFERENCE TO RELATED APPLICATIONS

This application is a National Stage of International Application No. PCT/US2018/030948, filed May 3, 2018, which claims the benefit of U.S. Provisional Application No. 62/500,499, filed May 3, 2017. The contents of each of which are incorporated by reference in their entirety.

TECHNICAL FIELD

STATEMENT OF FEDERALLY FUNDED RESEARCH

Not applicable.

This application generally relates to the field of therapeutic remedies and diagnostic methods, more specifically, to the diagnosis and treatment of infection involving Streptococcal pyrogenic exotoxin A (SpeA) and/or killer T follicular helper cells, methods of preparation and use thereof.

BACKGROUND

Recurrent tonsillitis (RT) is a common pediatric disease for which *Streptococcus pyogenes* is the most frequent bacterial infection. Tonsillectomies are the most common pediatric surgery in America. There are over 530,000 tonsillectomies performed annually in the US, with recurrent tonsillitis associated with *S. pyogenes* being the most common indication. Strep throat accounts for 20-30% of pediatric sore throat visits. If left untreated, it can result in the serious adverse sequellae of acute rheumatic fever and rheumatic heart disease. Given the extensive burden of *S. pyogenes* in recurrent tonsillitis, the recurrent tonsillitis immune response needs to be further elucidated.

*S. pyogenes* is the most common bacterial cause of RT or strep throat. Elective tonsillectomy is indicated after a child experiences at least seven episodes of strep throat in one year, five episodes in each of the previous two years, or three episodes in each of the previous three years per the American Academy of Otolaryngology[36]. RT can be a severe disease, resulting in substantial morbidity and school absences in hundreds of thousands of kids per year. FIG. 2 shows mean of 12 tonsillitis episodes among RT children compared to 0.5 episodes among non-RT children (p<0.0001). Children presenting with fever, tonsillar swelling or exudates, enlarged cervical lymph nodes, and absence of cough warrant testing for *S. pyogenes*[37]. Prompt antibiotic treatment is necessary for persons who test positive[38]. Untreated *S. pyogenes* tonsillopharyngitis can result in complications such as acute rheumatic fever, glomerulonephritis, and rheumatic heart disease, an autoimmune mediated destruction of heart valves[39].

The two most common indications for tonsillectomy in children are sleep-disordered breathing and recurrent tonsillitis[38]. Children with sleep disordered breathing do not present with an overt infection. Instead, these children have impaired airway flow resulting in snoring or apneic episodes and reduced sleep quality[40]. It is a long-standing mystery why some children get recurrent *S. pyogenes* tonsillopharyngitis. Specific strains of *S. pyogenes* have been proposed as the cause[38, 41, 42], which may play a role in why some children get RT and others do not. However, there are no compelling data in the literature supporting that explanation.

In light of at least the above, there is a need in the art for novel diagnostic and treatment for tonsillitis and other conditions.

SUMMARY

This Summary is provided to introduce a selection of concepts in a simplified form that are further described below in the Detailed Description. This Summary is not intended to identify key aspects or essential aspects of the claimed subject matter.

In one broad aspect, the present disclosure relates to a method of treating or preventing a *Streptococcus pyogenes* infection in a subject, comprising eliciting, stimulating, inducing, promoting, increasing, or enhancing an immune response to Streptococcal pyrogenic exotoxin A (SpeA) in the subject.

In another broad aspect, the present disclosure relates to a vaccine composition comprising Streptococcal pyrogenic exotoxin A (SpeA), or a peptide, variant, homologue, derivative or subsequence thereof, and an adjuvant.

In another broad aspect, the present disclosure relates to a method of treating tonsillitis or strep throat in a subject, the method comprising administering an agent that modulates, reduces, inhibits, decreases or blocks Streptococcal pyrogenic exotoxin A (SpeA) in an amount sufficient to treat tonsillitis or strep throat in the subject. In one embodiment, the agent may include a peptide, protein, recombinant protein, recombinant peptides, antibody, small molecule, ligand mimetic, nucleic acid or pharmaceutical composition, which agent can modulate, reduce, inhibit, decrease or alleviate one or more symptoms associated with tonsillitis or strep throat.

In another broad aspect, the present disclosure relates to a method of determining whether a subject has, is at risk of having, or is need of treatment for tonsillitis or strep throat, the method comprising processing a biological sample from the subject for determining the Human Leukocyte Antigen (HLA) Class II alleles present in the sample. In one embodiment, determining the HLA Class II alleles includes determining whether the subject has one or more of HLA Class II alleles, HLA DBQ1*06:02, HLA DRB1*01:01 and HLA DRB1*07:01.

In another broad aspect, the present disclosure relates to a method for treatment of a subject for tonsillitis or strep throat, the method comprising processing a biological sample from a subject for determining the Human Leukocyte Antigen (HLA) Class II alleles present in the sample, wherein the presence of allele HLA DBQ1*06:02 is indicative that the subject should not receive treatment for tonsillitis or strep throat and presence of one or both of alleles HLA DRB1*01:01 and HLA DRB1*07:01 is indicative that the subject should receive treatment for tonsillitis or strep throat, and treating the subject based on the determining step.

In another broad aspect, the present disclosure relates to a method of determining whether a subject has, is at risk of having, or is need of treatment for tonsillitis or strep throat, comprising processing a biological sample from the subject, the sample being suspected of including germinal center T follicular helper cells, for measuring an amount of the germinal center T follicular helper cells which are specific for or responsive to Streptococcal pyrogenic exotoxin A (SpeA), and comparing the measured amount to a reference amount, wherein a lower measured amount compared to the reference amount is indicative that the subject has, is at risk of having, or is need of treatment for tonsillitis or strep throat.

In another broad aspect, the present disclosure relates to a method of determining whether a subject should receive treatment for tonsillitis or strep throat, comprising processing a biological sample from the subject, the sample being suspected of including germinal center T follicular helper cells, for measuring an amount of germinal center T follicular helper cells specific for or responsive to Streptococcal pyrogenic exotoxin A (SpeA), and comparing the measured amount to a reference amount, wherein a lower measured amount compared to the reference amount is indicative that the subject should receive treatment for tonsillitis or strep throat.

In another broad aspect, the present disclosure relates to a method of determining an efficacy of a treatment for tonsillitis or strep throat in a subject, the method comprising processing a biological sample from the subject, the sample being suspected of including germinal center T follicular helper cells, for measuring an amount of the germinal center T follicular helper cells specific for or responsive to Streptococcal pyrogenic exotoxin A (SpeA), and comparing the measured amount to a reference amount.

In another broad aspect, the present disclosure relates to a method for treating a subject for a disease or disorder associated with impaired germinal centers, the method comprising: processing a biological sample from the subject, the sample being suspected of including killer germinal center T follicular helper cells (killer GC Tfh cells), to determine a concentration level thereof, comparing the concentration level to a reference level, and treating said subject at least based on said comparison, the treating step including inhibiting activation, differentiation, proliferation, number or activity of killer GC Tfh cells so as to modulate the concentration of said killer GC Tfh cells in said subject.

In another broad aspect, the present disclosure relates to a method of determining an efficacy of a treatment for tonsillitis or strep throat in a subject, the method comprising processing a biological sample from the subject, the sample being suspected of including germinal center T follicular helper cells, for measuring an amount of the germinal center T follicular helper cells specific for or responsive to Streptococcal pyrogenic exotoxin A (SpeA), and comparing the measured amount to a reference amount.

In another broad aspect, the present disclosure relates to a method for treating a subject for a disease or disorder associated with impaired germinal centers, the method comprising processing a biological sample from the subject, the sample being suspected of including killer germinal center T follicular helper cells (killer GC Tfh cells), to determine a concentration level thereof, comparing the concentration level to a reference level, and treating said subject at least based on said comparison, the treating step including inhibiting activation, differentiation, proliferation, number or activity of killer GC Tfh cells so as to modulate the concentration of said killer GC Tfh cells in said subject.

In another broad aspect, the present disclosure relates to a method for treatment of a subject for a disease or disorder associated with impaired germinal centers, the method comprising modulating, reducing, inhibiting, decreasing or blocking activation, differentiation, proliferation, number or activity of killer germinal center T follicular helper cells (killer GC Tfh cells).

In another broad aspect, the present disclosure relates to a method for evaluating a condition status in a subject, the condition being a disease or disorder associated with impaired germinal centers, the method comprising providing a biological sample from said subject, the sample being suspected of including killer germinal center T follicular helper cells (killer GC Tfh cells); processing the sample to determine a concentration, activation, differentiation, proliferation or activity level of said killer GC Tfh cells in said sample; comparing the concentration, activation, differentiation, proliferation or activity level to a reference level; and evaluating the condition status based on at least the comparison step, the condition being associated with impaired germinal centers.

In another broad aspect, the present disclosure relates to a method for treatment of a subject for a disease or disorder associated with impaired germinal centers, the method comprising modulating, reducing, inhibiting, decreasing or blocking activation, differentiation, proliferation, number or activity of killer germinal center T follicular helper cells (killer GC Tfh cells).

In another broad aspect, the present disclosure relates to a method for evaluating a condition status in a subject, the condition being a disease or disorder associated with impaired germinal centers, the method comprising providing a biological sample from said subject, the sample being suspected of including killer germinal center T follicular helper cells (killer GC Tfh cells); processing the sample to determine a concentration, activation, differentiation, proliferation or activity level of said killer GC Tfh cells in said sample; comparing the concentration, activation, differentiation, proliferation or activity level to a reference level; and evaluating the condition status based on at least the comparison step in step (c), the condition being associated with impaired germinal centers.

In another broad aspect, the present disclosure relates to a method of determining response or resistance to treatment for a disease or disorder associated with impaired germinal centers in a subject undergoing treatment for a disease or disorder associated with impaired germinal centers, the method comprising providing a biological sample from said subject, the sample being suspected of including killer germinal center T follicular helper cells (killer GC Tfh cells); processing the sample to determine a concentration, activation, differentiation, proliferation or activity level of said killer GC Tfh cells in said sample; comparing the concentration, activation, differentiation, proliferation or activity level to a reference level; and evaluating the response or resistance to the treatment based on at least the comparison step.

In another broad aspect, the present disclosure relates to a method for treating a subject for an autoimmune disease, the method comprising: processing a biological sample from the subject, the sample being suspected of including killer germinal center T follicular helper cells (killer GC Tfh cells), to determine a concentration level thereof; comparing the concentration level to a reference level; and treating said subject at least based on said comparison, the treating step including stimulating activation, differentiation, proliferation, number or activity of killer GC Tfh cells so as to modulate the concentration of said killer GC Tfh cells in said subject.

In another broad aspect, the present disclosure relates to a method for treatment or prevention of an autoimmune disease in a subject, the method comprising modulating, increasing, enhancing, eliciting, stimulating or promoting activation, differentiation, proliferation, number or activity of killer germinal center T follicular helper cells (killer GC Tfh cells).

In another broad aspect, the present disclosure relates to a method of determining response or resistance to treatment for a disease or disorder associated with impaired germinal centers in a subject undergoing treatment for a disease or disorder associated with impaired germinal centers, the method comprising: providing a biological sample from said subject, the sample being suspected of including killer germinal center T follicular helper cells (killer GC Tfh cells); processing the sample to determine a concentration, activation, differentiation, proliferation or activity level of said killer GC Tfh cells in said sample; comparing the concentration, activation, differentiation, proliferation or activity level to a reference level; and evaluating the response or resistance to the treatment based on at least the comparison step.

In another broad aspect, the present disclosure relates to a method for treating a subject for an autoimmune disease, the method comprising: processing a biological sample from the subject, the sample being suspected of including killer germinal center T follicular helper cells (killer GC Tfh cells), to determine a concentration level thereof; comparing the concentration level to a reference level; and treating said subject at least based on said comparison, the treating step including stimulating activation, differentiation, proliferation, number or activity of killer GC Tfh cells so as to modulate the concentration of said killer GC Tfh cells in said subject.

In another broad aspect, the present disclosure relates to a method for treatment or prevention of an autoimmune disease in a subject, the method comprising modulating, increasing, enhancing, eliciting, stimulating or promoting activation, differentiation, proliferation, number or activity of killer germinal center T follicular helper cells (killer GC Tfh cells).

In another broad aspect, the present disclosure relates to a method for treatment or prevention of an autoimmune disease in a subject, the method comprising administrating to the subject an effective amount of a purified killer germinal center T follicular helper cell (killer GC Tfh cell) population.

In another broad aspect, the present disclosure relates to a pharmaceutical composition comprising isolated killer germinal center T follicular helper cells (killer GC Tfh cells) and a pharmaceutically acceptable carrier, wherein said killer GC Tfh cells are modified so as to have modified gene expression, modified cell function or to include a ribonucleic acid interference (RNAi)-causing molecule, or a conjugated therapeutic agent.

In another broad aspect, the present disclosure relates to a method of determining whether a subject has, is at risk of having, or is in need of treatment for tonsillitis or strep throat, the method comprising processing a biological sample from the subject, the sample being suspected of containing anti-Streptococcal pyrogenic exotoxin A (SpeA) antibodies, for measuring an amount of anti-SpeA antibodies in the biological sample, and comparing the measured amount of anti-SpeA antibodies to an amount of anti-SpeA antibodies in a control sample.

All features of embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific embodiments is provided herein below with reference to the accompanying drawings in which:

FIGS. 4A to 4C show HLA associations identified in RT patients in accordance with an embodiment of the present disclosure;

FIGS. 6A to 6I show that SpeA stimulation of Granzyme B+GC killer Tfh cells from RT tonsils induces granzyme B and perforin in accordance with an embodiment of the present disclosure;

FIGS. 9A and 9B shows RT and non-RT patient HLA types in accordance with an embodiment of the present disclosure;

FIGS. 11A and 11B show differences in gene expression of SpeA-responsive GC Tfh from RT and non-RT tonsils in accordance with an embodiment of the present disclosure;

FIGS. 12A to 12L show results of SpeA induced granzyme B production in accordance with an embodiment of the present disclosure;

FIG. 16A shows Granzyme B expression by unstimulated GC killer Tfh cells, and FIG. 16B shows SpeA-stimulated Granzyme B+GC killer Tfh cells. RT=11, non-RT=11. P-values were determined by Wilcoxon Rank test. Please replace paragraph [0050] with the following amended paragraph:

Figure 1A:
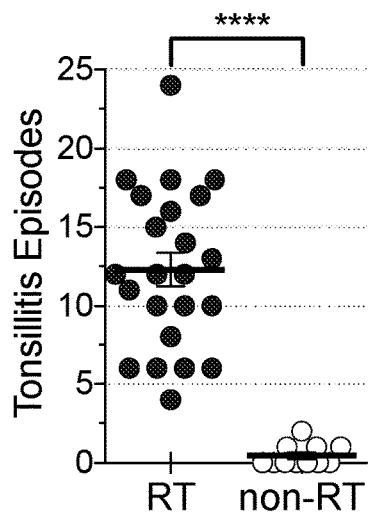
FIGS. 1A to 1J show non-limiting examples of RT tonsils having significantly more Granzyme B+GC killer Tfh and GC B cells in accordance with an embodiment of the present disclosure.

In the drawings, embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

Illustrative embodiments of the disclosure will now be more particularly described. While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the invention and do not delimit the scope of the invention. For the purpose of clarity, technical material that is known in the technical fields related to the invention has not been described in detail so that the invention is not unnecessarily obscured.

Tonsils are lymph node-like organs rich in germinal centers (GC) and are the nidus of infection for strep throat. Germinal centers consist primarily of T follicular helper (Tfh) cells, B cells, and follicular dendritic cells. Tfh cells are specialized CD4+ T cells whose function is to provide help to GC B cells. Tfh cells are critical for germinal center function, as they regulate most aspects of GC B cell biology, including signals for survival, proliferation, somatic hypermutation, antibody affinity maturation, class switch recombination, and differentiation into memory B and plasma cells. A pathogen-specific GC Tfh cell response is key for the generation of high affinity antibodies and B cells.

By integrating deep immune profiling and clinical data with transcriptomic and functional analyses, the present inventors have found that there is an immunological basis for recurrent streptococcal tonsillitis. Antibody responses are a central part of the immune system. T follicular helper CD4 T cells (Tfh cells) are required for germinal centers, and thus the majority of high affinity antibody responses. Tfh cells have important roles in protection from infectious diseases. Disclosed herein is a novel method for quantifying pathogen-specific Tfh cells, the activation immune marker (AIM) assay. With this technique the inventors have identified antigen-specific GC Tfh cells, and used them for functional studies and RNA-sequencing transcriptomic analysis. The inventors have identified a surprising new type of GC Tfh cell which can express granzyme B, and thus are "killer GC Tfh cells" with novel functions, including association with recurrent tonsillitis.

The present inventors have also discovered specific HLA alleles that are associated with 'at risk' and 'protective' outcomes, with the protective allele being associated with a different interaction with an *S. pyogenes* immune evasion protein. The present invention allows for earlier screening in children and decreased likelihood of developing adverse effects to *S. pyogenes*.

The present inventors have also discovered central roles for SpeA and anti-SpeA IgG in tonsillitis pathogenesis and protective immunity, respectively. Clarification of this novel immune evasion strategy may allow for rational design of countermeasures. For example, these findings indicate that an inactivated SpeA toxoid vaccine may be a simple and reasonable candidate for consideration as a means to eliminate hundreds of thousands of costly RT disease cases per year, and potentially significantly reduce childhood strep throat disease burden generally.

The present disclosure aims to provide novel methods and compounds for protecting, vaccinating against, or treating infection (e.g., strep, tonsillitis) or other conditions, diagnosing and identifying subjects at risk of said conditions, as well as at least detecting, identifying, characterizing, inhibiting, activating, isolating and/or administering killer GC Tfh cells.

The inventors have developed a cohort of 138 children who have undergone tonsillectomies for either RT or sleep disordered breathing, a non-RT indication. This is the largest cohort of tonsillitis samples in the world with live cells. Sleep disordered breathing serves as the comparator non-RT group for these reasons: (1) these cases are not associated with infection, (2) these tonsils are ethnically and geographically compatible to the RT group, as all these children were enrolled in the San Diego area, (3) these tonsils provide viable cells to perform functional assays, and (4) tonsils are not removed from otherwise healthy children. The inventors performed histologic and phenotypic analyses on this cohort. Surprisingly, flow cytometry revealed that RT tonsils have smaller germinal centers and significantly fewer GC Tfh and GC B cells. Genotypic analyses identified HLA Class II allele associations, with the identification of "At Risk" alleles in RT tonsils and a "Protective" allele in non-RT tonsils, previously associated with invasive *S. pyogenes* infection. Overall, the data indicates that RT children have a genetic immunosusceptibility to recurrent infection. Without being limited to any particular theory, children with RT may have a genetic immunosusceptibility to recurrent *S. pyogenes* infections due to differential SpeA superantigen molecular interactions, resulting in smaller germinal centers, significantly fewer GC Tfh and GC B cells and weakened overall ability to generate a protective anti-*S. pyogenes* adaptive immune response.

The inventors have developed a novel method for quantifying pathogen-specific Tfh cells, the activation immune marker (AIM) assay. With this technique, it is possible to identify antigen-specific GC Tfh cells and use them for functional studies and RNA-sequencing transcriptomic analysis. A surprising new type of GC Tfh cell which can express granzyme B has been identified. These GC Tfh cells express granzyme B upon stimulation with the *S. pyogenes* superantigen streptococcal pyrogenic exotoxin A (SpeA), present in strains causing strep throat. There is evidence that these cells have cytolytic activity, and thus these new cells have been dubbed "killer Tfh" cells. Flow cytometry of SpeA-responsive GC Tfh cells indicates that RT tonsils have more granzyme B+GC Tfh cells than non-RT tonsils. These killer Tfh cells develop aberrantly as a result of *S. pyogenes* immunomodulation of the tonsil, whereby children with repeated *S. pyogenes* infections develop inadequate *S. pyogenes* germinal center responses and reduced ability to produce protective *S. pyogenes* antibodies.

Compositions Comprising SpeA

The present disclosure provides compositions which can be useful, for example, for treating and/or preventing *Streptococcus pyogenes* infection in a subject, including for treating and/or preventing strep throat and tonsillitis (e.g. recurrent tonsillitis).

In certain embodiments, the composition comprises Streptococcal pyrogenic exotoxin A (SpeA), or a peptide, variant, homologue, derivative or subsequence thereof.

In certain embodiments, the composition may include a sufficient amount of SpeA, or a peptide, variant, homologue, derivative or subsequence thereof to produce an immunogenic response in a typical subject.

In certain embodiments, the composition may include one or more acceptable carrier selected from the acceptable carriers described herein. For example, an acceptable carrier may be selected from gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

Additionally or alternatively, the composition of the present disclosure may include one or more pharmaceutically acceptable salt selected from the pharmaceutically acceptable salts described herein. For example, a pharmaceutically acceptable salt may be selected from sodium chloride, potassium chloride, sodium sulfate, ammonium sulfate, or sodium citrate. The concentration of the pharmaceutically acceptable salt can be any suitable concentration known in the art, and may be selected from about 10 mM to about 200 mM.

Additionally or alternatively, the composition of the present disclosure may further include an acceptable adjuvant thereby forming a vaccine composition and may include a sufficient amount of the adjuvant to increase the composition's immunogenicity to a level high enough to effectively vaccinate a typical subject. For example, an adjuvant may be selected from aluminum hydroxide or mineral oil, and a stimulator of immune responses, such as Bordatella pertussis or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A. Suitable adjuvants also include, but are not limited to, toll-like receptor (TLR) agonists, particularly toll-like receptor type 4 (TLR-4) agonists (e.g., monophosphoryl lipid A (MPL), synthetic lipid A, lipid A mimetics or analogs), aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly (lactide-co-glycolides) (PLG) microparticles, poloxamer particles, microparticles, liposomes, oil-in-water emulsions, MF59, and squalene. In some embodiments, the adjuvants are not bacterially-derived exotoxins. In one embodiment, adjuvants may include adjuvants which stimulate a Th1 type response such as 3DMPL or QS21. Adjuvants may also include certain synthetic polymers such as poly amino acids and co-polymers of amino acids, saponin, paraffin oil, and muramyl dipeptide. Adjuvants also encompass genetic adjuvants such as immunomodulatory molecules encoded in a co-inoculated DNA, or as CpG oligonucleotides. The coinoculated DNA can be in the same plasmid construct as the plasmid immunogen or in a separate DNA vector. The reader can refer to Vaccines (Basel). 2015 June; 3(2): 320-343 for further examples of suitable adjuvant.

In certain embodiments, the vaccine composition has a changed functional property, in that the immunogenicity of the vaccine composition is different (higher) than the mere "sum" of the immunogenicity of the individual components. The vaccine composition's changed immunogenicity is a marked difference in functional characteristics as compared to the natural counterparts.

The following exemplification of carriers, modes of administration, dosage forms, etc., are listed as known possibilities from which the carriers, modes of administration, dosage forms, etc., may be selected for use with the present composition. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

The compositions of the present disclosure may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For instance, the composition of the present disclosure may be administered in the form of an injectable preparation, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. Suitable dosages will vary, depending upon factors such as the amount of each of the components in the composition, the desired effect (short or long term), the route of administration, the age and the weight of the subject to be treated. Any other methods well known in the art may be used for administering the composition of the present disclosure.

The composition of the present disclosure may be formulated as a dry powder (i.e., in lyophilized form). Freeze-drying (also named lyophilisation) is often used for preservation and storage of biologically active material because of the low temperature exposure during drying. Typically the liquid antigen is freeze dried in the presence of agents to protect the antigen during the lyophilization process and to yield a cake with desirable powder characteristics. Sugars such as sucrose, mannitol, trehalose, or lactose (present at an initial concentration of 10-200 mg/mL) are commonly used for cryoprotection of protein antigens and to yield lyophilized cake with desirable powder characteristics. Lyophilizing the composition theoretically results in a more stable composition.

In certain embodiments, the composition of the present disclosure may be formulated as a liquid (e.g. aqueous formulation), e.g., as syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Therapeutic Methods

The present disclosure provides methods for treating and/or preventing *Streptococcus pyogenes* infection in a subject, including for treating and/or preventing strep throat and tonsillitis (e.g. recurrent tonsillitis).

In certain embodiments, the method comprises eliciting, stimulating, inducing, promoting, increasing, or enhancing an immune response to Streptococcal pyrogenic exotoxin A (SpeA) or a peptide, variant, homologue, derivative or subsequence thereof, in a subject. Such immune response may be useful against *Streptococcus pyogenes*. For example, the present inventors have found that administering to a subject a SpeA, or a peptide, variant, homologue, derivative or subsequence thereof, can elicit or enhance an immune response against *Streptococcus pyogenes* thereby preventing and/or treating *Streptococcus pyogenes* infection in the subject.

In other certain embodiments, the method comprises vaccinating against *Streptococcus pyogenes* by administering SpeA, or a peptide, variant, homologue, derivative or subsequence thereof to a subject.

In yet other certain embodiments, the method comprises treating and/or preventing tonsillitis or strep throat in a subject by administering an agent that modulates SpeA expression or activity. Such agent may, for example, reduce, inhibit, decrease or block SpeA expression or activity in the subject. For example, but without being limited thereto, such agent may include an antibody having binding specificity to SpeA, which when administered to a subject will modulate SpeA expression or activity in the subject. In another example, such agent may include an RNAi-inducing molecule, such as an siRNA, which when administered to a subject will modulate SpeA expression or activity in the subject. In another example, such agent may include a peptide, protein, recombinant protein, recombinant peptides, antibody, small molecule, ligand mimetic, nucleic acid or pharmaceutical composition, which modulates SpeA expression or activity in the subject. The person of skill will readily foresee or be able to identify what agent may be suitable for this purpose without undue effort.

Diagnostic Methods

The present disclosure also provides diagnostic methods for determining whether a subject has or is it risk of having *Streptococcus pyogenes* infection and/or development of strep throat or tonsillitis (e.g. recurrent tonsillitis). Optionally, such methods may further include a treatment step when the subject is determined as having or being at risk of having *Streptococcus pyogenes* infection and/or development of strep throat or tonsillitis.

In certain embodiments, the method comprises detection of certain Human Leukocyte Antigen (HLA) alleles that the inventors have discovered to be associated with susceptibility or protection from *Streptococcus pyogenes* infection and/or development of strep throat or tonsillitis (e.g. recurrent tonsillitis). These HLA alleles are further described later in this text.

In other certain embodiments, the method comprises use of Tech_dev_2011 a novel activation induced marker assay for detection of antigen specific cells (e.g. germinal center T follicular helper cells) and this method can be used to detect SpeA specific or responsive immune cells (e.g. SpeA specific or responsive germinal center T follicular helper cells). The germinal center T follicular helper cells will be further described later in this text.

In yet other certain embodiments, the method comprises obtaining a plasma or serum sample from a subject and measuring in the sample the amount of anti-SpeA antibodies or the amount of SpeA specific or responsive immune cells. For example, such measuring may include contacting the sample with SpeA, or a peptide, variant, homologue, derivative or subsequence thereof, and detecting/quantifying binding between anti-SpeA antibodies in the sample and the SpeA, peptide, variant, homologue, derivative or subsequence thereof.

Alternatively or additionally, such measuring the number of cells in the sample which are SpeA specific or responsive immune cells may be performed using techniques such as, but without being limited thereto, ELISA assay, ELISPOT assay, an activation induced marker (AIM) assay, and the like. For example, when using the AIM assay, the method may include detecting at least CD25, Ox40, PD-L1, or a combination thereof. For example, the AIM may include detecting CD25, Ox40 and PD-L1.

Such method may further comprise comparing the amount of SpeA specific or responsive immune cells and/or anti-SpeA antibodies to amounts in control samples, which comparison generates an input from which the person of skill can determine useful information. For example, in cases when there is a lower measured amount compared to the reference amount, this may be indicative that the subject should receive treatment for tonsillitis or strep throat. In other instances, when there is a lower measured amount compared to the reference amount, this may be indicative that that the subject has, is at risk of having, or is need of treatment for tonsillitis or strep throat.

In certain embodiments, one or more of the above methods can also be applied to determine the efficacy of a therapeutic treatment as described herein.

Applications for Using the Tfh Population

The present disclosure also provides an enriched or purified preparation of novel killer germinal center T follicular helper cell population (killer GC Tfh cells), methods of making a preparation of such population, and methods of using same.

In certain embodiments, the killer GC Tfh cells of the present disclosure have at least the phenotype of increased Granzyme B$^+$.

Additionally or alternatively, the killer GC Tfh cells of the present disclosure have one or more of increased expression of PRDM1 (BLIMP1), decreased expression of BCL1, increased expression of ICOS, increased expression of GZMB, decreased expression of CD28, increased expression of CTLA4, increased expression of EOMES and increased expression of TBX21 (T-bet) when compared to unstimulated germinal center T follicular helper cells.

Additionally or alternatively, the killer GC Tfh cell population includes killer GC Tfh cells that are modified so as to have modified gene expression, modified cell function or to include a ribonucleic acid interference (RNAi)-causing molecule, or a conjugated therapeutic agent. The person of skill in the art will readily foresee how to obtain such modified cells using tehcniques available in the art.

The person of skill will appreciate that the killer GC Tfh cell population may be prepared in the form of a pharmaceutical composition, as discussed later in the text.

In certain embodiments, the methods of using the killer GC Tfh cell population provides a desired result, which may be for example, but without being limited thereto, therapeutic and/or prophylactic, or which may assist in evaluating the susceptibility of a subject to disease or which may assist in evaluating the effectiveness of a given treatment, and the like.

In certain embodiments, the methods of using the killer GC Tfh cell population is for treatment or prevention of a disease condition in a subject. The method includes administering to the subject an effective amount of a purified preparation of the killer GC Tfh cell population of the present disclosure. Such administration can be used in combination with other steps described herein, for example, to monitor the effectiveness of a treatment.

In certain embodiments, the method of using the killer GC Tfh cell population is for the treatment of an autoimmune disease.

In certain embodiments, the methods of using the killer GC Tfh cell population includes modulating activation, differentiation, proliferation, number or activity of killer GC Tfh cells. For example, methods for treating an autoimmune disease may include modulating, increasing, enhancing, eliciting, stimulating or promoting activation, differentiation, proliferation, number or activity of killer GC Tfh cells. In certain embodiments, the method is for treating a subject for a disease or disorder associated with impaired germinal centers (e.g. strep throat, tonsillitis). Such method comprises modulating, reducing, inhibiting, decreasing or blocking activation, differentiation, proliferation, number or activity of killer GC Tfh cells. Such method may be implemented ex vivo or in vivo. The person of skill having will readily understand how to modulate, inhibit, decrease or block activation, differentiation, proliferation, number or activity of killer GC Tfh cells without undue effort.

In yet other certain embodiments, the method is for evaluating a disease status in a subject or to determine responsiveness or resistance of the subject to a therapeutic treatment (e.g. treatment for strep throat, tonsillitis, or an autoimmune disease). Such method comprises obtaining a sample from the subject and processing the sample to measure an amount or activity of killer GC Tfh cells contained in the sample. The measurement can then be used to evaluate the disease status in the subject or to determine responsiveness or resistance of the subject to the therapeutic treatment.

Definitions

Unless otherwise defined, all technical and scientific terms used herein have the same meaning as commonly understood by a person of ordinary skill in the art to which the present invention pertains. As used herein, and unless stated otherwise or required otherwise by context, each of the following terms shall have the definition set forth below.

"Administering" an expression vector, nucleic acid molecule, or a delivery vehicle (such as a chitosan nanoparticle) to a cell comprises transducing, transfecting, electroporation, translocating, fusing, phagocytosing, shooting or ballistic methods, etc., i.e., any means by which a protein or nucleic acid can be transported across a cell membrane and preferably into the nucleus of a cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

As used herein, the terms "treatment", "treating", and the like, may include amelioration or elimination of a developed disease or condition once it has been established or alleviation of the characteristic symptoms of such disease or condition. As used herein, these terms may also encompass, depending on the condition of the subject, preventing the onset of a disease or condition or of symptoms associated with the disease or condition, including for example reducing the severity of the disease or condition or symptoms associated therewith prior to affliction with the disease or condition. Such prevention or reduction prior to affliction may refer to administration of a therapeutic compound to a subject that is not at the time of administration afflicted with the disease or condition. "Preventing" may also encompass preventing the recurrence or relapse of a previously existing disease or condition or of symptoms associated therewith, for instance after a period of improvement.

The subject or patient can be any mammal, including a human.

The disease or disorder associated with impaired germinal centers includes tonsillitis or strep throat. In certain embodiments, the tonsillitis is recurrent tonsillitis.

A "standard control" "control" or "control biological sample" refers to a sample, measurement, or value that serves as a reference, usually a known reference, for comparison to a subject biological sample, test sample, measurement, or value. For example, a test biological sample can be taken from a patient suspected of strep throat or tonsillitis and compared to samples from a known patient with strep throat or tonsillitis or a known normal individual without strep throat or tonsillitis. A standard control can also represent an average measurement or value gathered from a population of similar individuals that do not have a given disease or condition (i.e. standard control population), e.g., healthy individuals with a similar medical background, same age, weight, etc. that do not have strep throat or tonsillitis. A standard control value can also be obtained from the same individual, e.g., from an earlier-obtained sample, prior to disease or condition (e.g. strep throat or tonsillitis), or prior to treatment. One of skill will recognize that standard controls can be designed for assessment of any number of parameters (e.g. RNA levels, protein levels, individual, specific cell types, specific bodily fluids, specific tissues, T cells, B cells, etc.).

One of skill in the art will understand which standard controls are valuable in a given situation and be able to analyse data based on comparisons to standard control values. Standard controls are also valuable for determining the significance of data. For example, if values for a given parameter are widely variant in standard controls, variation in test samples will not be considered as significant.

As used herein, a "purified cell population" refers to a cell population which has been processed so as to separate the cell population from other cell populations with which it is normally associated in its naturally occurring state. The purified cell population can, thus, represent an enriched cell population in that the relative concentration of the cell population in a sample can be increased following such processing in comparison to its natural state. In one embodiment, the purified cell population can refer to a cell population which is enriched in a composition in a relative amount of at least 80%, or at least 90%, or at least 95% or 100% in comparison to its natural state. Such purified cell population may, thus, represent a cell preparation which can be further processed so as to obtain commercially viable preparations.

The cells may be processed so as to be part of a pharmaceutical composition. For example, in one embodiment, the cell preparation can be prepared for transportation or storage in a serum-based solution containing necessary additives (e.g., DMSO), which can then be stored or transported in a frozen form. In doing so, the person of skill will readily understand that the cell preparation is in a composition that includes a suitable carrier, which composition is significantly different from the natural occurring separate elements. For example, the serum-based preparation may comprise human serum or fetal bovine serum, which is a structural form that is markedly different from the form of the naturally occurring elements of the preparation. The resulting preparation includes cells that are in dormant state, for example, that may have slowed-down or stopped intracellular metabolic reactions and/or that may have structural modifications to their cellular membranes. The resulting preparation includes cells that can, thus, be packaged or shipped while minimizing cell loss which would otherwise occur with the naturally occurring cells. This property of minimizing cell loss of the resulting preparation/composition is markedly different from properties of the cells by themselves in nature. A person skilled in the art would be able to determine a suitable preparation without departing from the present disclosure.

As used herein, the term "carrier" refers to any carrier, diluent or excipient that is compatible with the herein described composition and/or killer GC Tfh cells and can be given to a subject without adverse effects. Suitable acceptable carriers known in the art include, but are not limited to, water, saline, glucose, dextrose, buffered solutions, and the like. Such a carrier is advantageously non-toxic to the killer GC Tfh cells and not harmful to the subject. It may also be biodegradable. The carrier may be a solid or liquid acceptable carrier. A suitable solid acceptable carrier is a non-toxic carrier. For instance, this solid acceptable carrier may be a common solid micronized injectable such as the component of a typical injectable composition for example, but without being limited to, kaolin, talc, calcium carbonate, chitosan, starch, lactose, and the like. A suitable liquid acceptable carrier may be, for example, water, saline, DMSO, culture medium such as DMEM, and the like. The person skilled in the art will be able to determine a suitable acceptable carrier for a specific application without departing from the present disclosure.

The terms "determining," "measuring," "evaluating," "assessing," and "assaying," as used herein, generally refer to any form of measurement, and include determining if an element is present or not in a biological sample. These terms include both quantitative and/or qualitative determinations, which both require sample processing and transformation steps of the biological sample. Assessing may be relative or absolute. The phrase "assessing the presence of" can include determining the amount of something present, as well as determining whether it is present or absent.

The expression "therapeutically effective amount" may include the amount necessary to allow the component or composition to which it refers to perform its immunological role without causing overly negative effects in the host to which the component or composition is administered. The exact amount of the components to be used or the composition to be administered will vary according to factors such as the type of condition being treated, the type and age of the subject to be treated, the mode of administration, as well as the other ingredients in the composition.

EXAMPLES

The following Examples describe some exemplary modes of making and practicing certain compositions that are described herein. It should be understood that these examples are for illustrative purposes only and are not meant to limit the scope of the compositions and methods described herein.

Materials and Methods

The following materials and methods were used in the context of performing the following Examples.

Human Subject Research.

Fresh tonsils were obtained from pediatric donors undergoing tonsillectomy at Rady Children's Hospital or the Naval Medical Center. Specimens were collected at the time of surgery, at least 6 weeks after the last episode of tonsillitis, with most cases substantially further from the last episode of tonsillitis and antibiotic treatment. Beginning with later donors enrolled, at the time of tonsillectomy a blood specimen was also acquired. Informed consent was obtained from all donors under protocols approved by the institutional review boards (IRBs) of the University of California, San Diego, the La Jolla Institute for Allergy and Immunology (LJI), and the Naval Medical Center. In this study, we recruited children from the same geographic area to control for circulating strains within the community.

A Note on Tissue Sample Acquisition:

Tonsils are never removed from healthy children. Partial tonsil biopsies are not possible because of the small risk of life-threatening oropharyngeal hemorrhage. Cadaveric tonsils are not acceptable for research purposes, due to the highly apoptotic nature of GC B cells. Pediatric whole body organ donors are extremely rare, and those with tonsils harvested are even rarer, and those donors are regularly treated with high dose steroids and intravenous antibiotics continuously up to the moment of organ harvest, which are expected to substantially modify tonsillar biology and immune cells and thus are unaccepted for immunological comparisons.

Fresh lymph nodes were acquired from patients undergoing staging sentinel lymph node biopsy for early-stage breast cancer at University Hospital Southampton, UK, in whom said staging demonstrated the absence of lymphatic metastasis. All patients had provided informed consent for tissue donation for the purpose of clinical research study (UKCRN ID: 11947) according to protocols approved by the National Research Ethics Service following regional ethics committee review (South Central England).

Cell Processing.

Tonsillar mononuclear cells were obtained by homogenizing the tissue using a wire mesh, passage through a cell strainer, and isolation via Ficoll density gradient using Histopaque 1077. Peripheral blood mononuclear cells (PBMCs) were isolated by density gradient centrifugation using Histopaque 1077 (Sigma). For PBMCs, plasma was saved after density gradient centrifugation. Cells were then washed and suspended in fetal bovine serum (FBS) containing 10% dimethyl sulfoxide, and cryopreserved in liquid nitrogen.

Single cell suspensions of lymph node-derived cells were obtained from freshly excised axillary nodes following enzymatic digest (0.15 Wünsch units/ml Liberase DL (Roche), 800 Kunitz units/ml DNAse 1 (Sigma)) over 1 hour at 37° C. followed by passage through a wire mesh and 70 μm cell strainer (BD Falcon). Cells were suspended in complete RPMI 1640 (Gibco+25 mM HEPES (Sigma), Penicillin/Streptomycin (Sigma), L-Glutamine (Sigma), sodium pyruvate (Gibco)—"cRPMI") and cryopreserved (50% decomplemented human Ab serum (Sigma), 10% Dimethyl Sulfoxide (Sigma)) in liquid nitrogen until use.

Antibodies and Flow Cytometry.

Cells were labeled with fixable viability dye eFluor 780 (Thermo Fisher Scientific). FACS staining buffer consisted of 0.5% Bovine serum albumin (BSA) in phosphate buffered saline (PBS). Primary stains for leukocyte phenotyping (FIG. 1A) was done using fresh cells. Anti-human antibodies for surface staining of fresh tonsils are listed here, by company, Thermo Fisher Scientific: CD19 e780 (clone HIB19), CD14 e780 (clone 61D3), CD16 e780 (clone eBioCB16), CD3 e780 (clone UCHT1), CD25 PE-Cyanine 7 (clone BC96), PD-1 PE (clone eBioJ105), CD38 PE-cyanine 7 (clone HIT2), ICOS PerCP-eFluor™ 710 (clone ISA-3), CD27 PerCP-eFluor 710 (clone O323), CD45RO FITC (clone UCHL1); Biolegend: CD20 BV570 (clone 2H7), CD19 AF700 (clone HIB19), CXCR5 BV421 (clone J252D4); BD Biosciences CD3 AF700 (clone UCHT1) and CD4 APC (clone RPA-T4). Total cell numbers are not available, since part of the tonsil is always retained by the Pathology Department as fixed tissue for diagnostic purposes.

Anti-human antibodies for AIM assay are listed here, by company, Thermo Fisher Scientific: CD19 e780 (clone HIB19), CD14 e780 (clone 61D3), CD16 e780 (clone eBioCB16), OX40 FITC (clone Ber-ACT35), CD25 PE-Cyanine 7 (clone BC96), CD4 PerCP-eFluor710 (clone SK3); Biolegend: CD45RA BV570 (clone HI100), CXCR5 BV421 (clone J252D4), PD-1 BV785 (clone EH12.2H7), PD-L1 PE (clone 29E.2A3), CCR7 APC (clone G043H7).

Anti-human antibodies for the proliferation assay using HLA class II cell lines are listed here, by company, Thermo Fisher Scientific: OX40 FITC (clone Ber-ACT35), CD25 PE-Cyanine 7 (clone BC96), CD4 PerCP-eFluor 710 (clone SK3); Biolegend: PD-1 BV785 (clone EH12.2H7), PD-L1 PE (clone 29E.2A3). Annexin V APC Apoptosis Detection kit was utilized (Thermofisher).

Anti-human antibodies for the granzyme B Assay are listed here, by company, Thermo Fisher Scientific: CD19 e780 (clone HIB19), CD14 e780 (clone 61D3), CD16 e780 (clone eBioCB16), OX40 PE (clone Ber-ACT35), CD25 PE-Cyanine 7 (clone BC96), CD4 PerCP-eFluor710 (clone SK3); Biolegend: CD45RA BV570 (clone HI100), CXCR5 BV421 (clone J252D4), PD-1 BV785 (clone EH12.2H7), Granzyme B Alexa Fluor™ 647 (clone GB11), and Alexa Fluor 647 Mouse IgG1, κ Isotype Control (clone MOPC-21). Cells were acquired on a BD Fortessa and analyzed using FlowJo™ Software, version 9.9.4.

Anti-human antibodies for sorting GC Tfh and B cells are listed here, by company, Thermo Fisher Scientific: CD19 e780 (clone HIB19), CD14 e780 (clone 61D3), CD16 e780 (clone eBioCB16), CD8 e780 (clone RPA-T8), CD4 PerCP-eFluor 710 (clone SK3), CD38 APC (clone HIT2); Biolegend: CD45RA BV570 (clone HI100), CXCR5 BV421 (clone J252D4), PD-1 BV785 (clone EH12.2H7), CCR7 BV650 (clone G043H7), CD20 BV570 (clone 2H7). Anti-human antibodies for staining after a 5 day in vitro culture are listed here by company, Thermo Fisher Scientific: CD4 PerCP-eFluor710 (clone SK3), OX40 PE (clone Ber-ACT35), CD25 PE-Cyanine 7 (clone BC96), Biolegend: CD45RA BV570 (clone HI100), CXCR5 BV421 (clone J252D4), PD-1 BV785 (clone EH12.2H7), CD20 BV570 (clone 2H7), Granzyme B Alexa Fluor 647 (clone GB11), Perforin FITC (clone B-D48). Cells were acquired on a BD Celesta and analyzed using FlowJo Software, version 9.9.4.

Anti-human antibodies for sorting for the cytotoxicity assay are listed here, by company, Thermo Fisher Scientific: CD14 e780 (clone 61D3), CD16 e780 (clone eBioCB16), CD4 PerCP-eFluor710 (clone SK3), CD8 PeCy7 (RPA-T8), PD-1 PE (clone eBioJ105), CD38 APC (clone HIT2), CD19 AF488 (HIB19); Biolegend: CCR7 BV650 (clone G043H7), CXCR5 APC (clone J252D4); BD Biosciences: CD45RA PE-CF594 (clone H100). Cells were sorted on the BD FACSAria™ III or BD FACSAria Fusion. Data was analyzed using FlowJo 9.9.4.

Histology.

A small section was taken from each tonsil, fixed in 10% zinc formalin fixative for 24 hours at room temperature and transferred to 70% ethanol. For each tonsil, the microscopy core prepared a paraffin embedded section and an H&E stain. Slides were viewed using a Nikon Eclipse 80i. Images of three different locations on the same slide were taken (10× objective) and averaged per tonsil. The number of GCs and GC area were determined using "Image J" (NIH). Immunohistochemistry was performed by HistoTox Labs, Inc. (Boulder, Colo.). Each tissue was sectioned, mounted on a slide, and stained separately for CD20, Ki67, CD4, and PD-1.

Immunofluorescence Microscopy.

A small section was taken from each tonsil, fixed in in 4% paraformaldehyde at 4° C. for 2 hours, washed in PBS×3 for 10 minutes, and placed in a 30% sucrose gradient for at least 18 hours at 4° C. until the tissue sinks. The tissue section was washed in PBS and embedded in OCT compound using methylbutane and liquid nitrogen. Embedded tissues samples were stored at −80° C. Tissue sections were prepared by the LJI Microscopy core. For staining, slides were dried on the grill of the tissue culture hood for 30 minutes, washed in PBS×2 for 10 minutes, and blocked with 10% FBS containing 0.5% Triton™ X-100 for 1 hour at room temperature. Antibodies were from Biolegend: CD4 Alexa Fluor™ 488 (clone RPA-T4) and Granzyme B Alexa Fluor 647 (clone GB11) and Isotype Control Alexa Fluor 647. Slides were stained overnight at 4° C. The next morning, slides were washed in PBS×2×10 minutes, counterstained with Hoechst 3342 for 10 minutes, and washed in PBS×2× 10 minutes. Slides were then mounted in Prolong™ Gold. Slides were visualized using Olympus FluoView FV10i Confocal.

HLA Typing.

Genomic DNA was isolated from frozen tonsillar mononuclear cells using standard techniques (REPLI-g™, Qiagen). Typing was performed at Murdoch University (Perth, Western Australia).

Superantigen Binding Assay.

Recombinant SpeA produced in *E. coli* (Toxin Technology) was biotinylated following manufacturer's protocol using an EZ-Link™ Sulfo-NHS Biotinylation kit (Thermofisher). Biotinylated recombinant SpeA was incubated for 30 minutes at 4° C. in FACS buffer using cell lines expressing different HLA receptors. DQB1*03:02 and DQB1*06:02 were expressed on the RM3 line. Cells were washed twice in FACS buffer. Streptavidin Alexa Fluor 647 (Biolegend) was used as a secondary stain. Cells were also labeled with fixable viability dye eFluor™ 780 (Thermo Fisher Scientific). Cells were fixed in 2% paraformaldehyde and acquired on BD™ FACS LSRII. Data was analyzed using FlowJo™ 9.9.4 and histograms generated using FlowJo 10.2.

Superantigen Stimulation Assay.

Antigen Presenting Cells (APCs): HLA Class II cell lines were cultured in R10 media containing RPMI, Penicillin/Streptomycin, L-Glutamax, 10% FBS, MEM Non-essential amino acids, and Sodium Pyruvate. For HLA DRB1 expressing L cell lines, the selection media included 200 µg/mL G418. Prior to use of the HLA DRB1 cell line, 100 µg/mL Butyric acid was added overnight to induce expression of the HLA DRB1 receptor. For HLA DQB1 expressing RM3 cell lines, the selection media included 12 µg/mL Blasticidin+700 µg/mL G418. The number of APCs was optimized, using 5,000 cells per well of DRB1 expressing cell lines and 25,000 cells per well of DQB1 expressing cell lines. APCs were irradiated in a 96 well flat bottom tissue culture plate. CD4+ T cells: Cryopreserved PBMCs containing the HLA receptor of interest were thawed and purified using the EasySep™ Human CD4+ T cell enrichment kit (Stemcell Technologies), according to manufacturer's protocol to 95 to 98% purity). CD4+ T cells were CellTrace™ Violet (CTV) labeled and cultured at 100,000 cells per well. rSpeA was added to the well at different concentrations. As a control, CD4+ T cells alone were incubated with rSpeA in media consisting of RPMI+10% Human AB sera (off the clot, Gemini)+penicillin/streptomycin+L-Glutamax. After 5 days, cells were analyzed for upregulation of activation marker OX40 and CTV.

Antigen-Specific CD4+ T Cell Assays.

Tonsillar mononuclear cells were cultured at $1×10^6$ cells/well in AIM-V™ media in a 96 well round bottom plate for 18 hours. For the GAS-specific CD4+ T cell assay, cells were left unstimulated or stimulated with 10 µg/mL heat-inactivated, antibiotic-killed GAS25. As a comparison, cells were also stimulated with 10 µg/mL antibiotic-killed GAS or 10 µg/mL antibiotic-killed GAS deficient in SpeA, all from the same strain. The Nizet laboratory provided GAS strain M1T1 5448, originally isolated from a patient with necrotizing fasciitis and toxic shock syndrome (Chatellier, S. et al. Genetic relatedness and superantigen expression in group A *streptococcus* serotype M1 isolates from patients with severe and nonsevere invasive diseases. *Infection and Immunity* 68, 3523-3534 (2000)). A nonpathogenic Streptococcaceae, *Lactococcus lactis* NZ900060, was used as a negative control. For the AIM assay, tonsillar cells were stimulated with 10 µg/mL antibiotic-killed *Lactococcus*. Bacteria were cultured in 100 mL Todd-Hewitt broth (Difco) statically at 37° C. to OD600 0.6. Tissue culture grade penicillin/streptomycin (Invitrogen) was added to 1% and incubated for 1 hour. Cells were pelleted by centrifugation for 10 min at 4000×g, washed once and suspended in PBS. Samples were plated on Todd-Hewitt agar to confirm bacterial killing. Total protein was quantified by bicinchonic acid assay (Pierce) for use as antigen. To inactivate superantigen, antibiotic-killed GAS was heat-treated at 65° C. for 20 min. For the SpeA AIM assay, 1 µg/mL of rSpeA was utilized as a stimulus.

Intracellular Cytokine Staining for Granzyme B Expression.

Tonsillar mononuclear cells were cultured at $1×10^6$ cells/well in AIM-V media in a 96 well round bottom plate for 24 hours. Cells were either left unstimulated or stimulated with 1 µg/mL SpeA (Toxin Technology). At 20 hours, BD GolgiPlug™ was added prior to harvesting the cells at 24 hours for analysis, according to manufacturer's protocol (BD Biosciences). Cells were permeabilized using the BD Cytofix/Cytoperm™ kit for intracellular cytokines.

Intranuclear Staining.

Tonsillar mononuclear cells were cultured at $1×10^6$ cells/well in AIM-V media in a 96 well round bottom plate for 24 hours. Cells were permeabilized using the eBioscience™ Transcription buffer staining set (Thermofisher). FoxP3 PE (clone 236A/E7, Thermofisher) and Helios PE Dazzle (clone 22F6, Biolegend) were used.

RNA Sequencing.

Tonsillar mononuclear cells were cultured at $1×10^6$ cells/well in AIM-V media in a 96 well round bottom plate for 18 hours. Cells were stained using antibodies listed above with the exception of CCR7 and PD-L1. Cells were sorted on the BD FACSAria III or BD FACSAria Fusion for CD25+ OX40+GC Tfh cells. From 10 donors, cell numbers obtained ranged from $10^4$ to $10^5$ cells.

As described previously, total RNA was purified using a miRNAeasy micro kit (Qiagen) and quantified, as described previously (Seumois, G. et al. Epigenomic analysis of primary human T cells reveals enhancers associated with TH2 memory cell differentiation and asthma susceptibility. *Nature Publishing Group* 15, 777-788 (2014)). Standard quality control steps were included to determine total RNA quality using Agilent Bioanalyzer (RNA integrity number (RIN) >8.5; Agilent RNA 6000 Pico Kit). Purified total RNA (0.25 to 5 ng) was amplified following the Smart-Seq2 protocol. cDNA was purified using AMPure™ XP beads (1:1 ratio; Beckman Coulter). From this step, 1 ng cDNA was used to prepare a standard Nextera XT sequencing library (Nextera XT DNA sample preparation kit and index kit; Illumina). Samples were sequenced using a HiSeq2500 (Illumina) to obtain 50-bp single-end reads. Both whole-transcriptome amplification and sequencing library preparations were performed in a 96-well format to reduce assay-to-assay variability. Quality control steps were included to determine total RNA quality and quantity, the optimal number of PCR preamplification cycles (15 cycles), and fragment size selection. Samples that failed quality control were eliminated from further downstream steps. Barcoded Illumina sequencing libraries (Nextera; Illumina) were generated utilizing the automated platform (Biomek™ FXp). Libraries were sequenced on the HiSeq2500 Illumina platform to obtain 50-bp single-end reads (TruSeq™ Rapid Kit; Illumina), generating a median of about 13.6 million mapped 50 bp reads per sample.

RNA-Seq Analysis.

The single-end reads that passed Illumina filters were filtered for reads aligning to tRNA, rRNA, adapter sequences, and spike-in controls. The reads were then aligned to UCSC hg19 reference genome using TopHat (v 1.4.1). DUST scores were calculated with PRINSEQ Lite (v 0.20.3) and low-complexity reads (DUST>4) were removed from the BAM files. The alignment results were parsed via the SAMtools to generate SAM files. Read counts to each genomic feature were obtained with the htseq-count program (v 0.6.0) using the "union" option. After removing absent features (zero counts in all samples), the raw counts were converted to RPKM values and filtered by setting a cutoff value of 1. Multiplot Studio in the GenePattern suite was employed to generate the volcano plot with RPKM values. The raw counts were then imported to R/Bioconductor package DESeq2 to identify differentially expressed genes among conditions. DESeq2 normalizes counts by dividing each column of the count table (samples) by the size factor of this column. The size factor is calculated by dividing the samples by geometric means of the genes. This brings the count values to a common scale suitable for comparison. P-values for differential expression are calculated using Wald test that estimates the significance of coefficients in a fitted negative binomial generalized linear model (GLM). These p-values are then adjusted for multiple test correction using Benjamini Hochberg algorithm to control the false discovery rate. Cluster analyses including principal component analysis (PCA) and hierarchical clustering were performed using standard algorithms and metrics. Hierarchical clustering was performed using complete linkage with Euclidean metric.

Sorting GC Tfh and Non-GC B Cells for Granzyme B Expression.

Tonsillar mononuclear cells were sorted using the antibodies listed previously for GC Tfh (CXCR5hiPD-1hi of CD45RA-CD4+) and non-GC B cells (CD20+CD38−) to serve as APCs. Cells were plated at 75,000 GC Tfh and GC B cells 96 well round bottom plates in media containing 10% human sera (RPMI+penicillin/streptomycin+L-glutamax)+IL-7 (Final concentration 4 ng/mL). Cells were either left unstimulated or stimulated with 1 µg/mL SpeA. After a 5 day in vitro culture, cells were harvested and stained for granzyme B (antibodies listed previously).

Cytotoxicity Assay.

Tonsillar mononuclear cells were sorted (antibodies listed previously) for GC Tfh (CXCR5hiPD-1hi of CD45RA-CD4+), mTfh (CXCR5+PD-1+ of CD45RA-CD4+), non-Tfh (CXCR5− of CD45RA-CD4+), naïve CD4+(CCR7+CD45RA+), and CD8+ T cells as effector cells. Tonsillar mononuclear cells were also sorted for autologous non GC B and plasma cells (CD19+CD38−) to serve as target cells. B cells were labeled with CTV and cultured at a 2:1 ratio of effector cells to 1 target cell in media containing 5% human sera (RPMI+penicillin/streptomycin+L-glutamax). Cells were plated at 50,000 target cells to 100,000 effector cells in 96 well round bottom plates. Cells were either left unstimulated or stimulated with 1 µg/mL SpeA. As a control, B cells were also left unstimulated or stimulated with 1 µg/mL SpeA. After 40 hours of incubation, cells were harvested and the number of CTV+ cells was quantified by flow cytometry. Cells were plated at least in triplicate, depending on how many GC Tfh cells were sorted from each tonsil. Killing capacity for GC Tfh cells was determined by averaging the absolute counts of CTV-labeled B cells co-cultured with unstimulated GC Tfh or naïve CD4+ T cells=B. The absolute cell count of CTV-labeled B cells co-cultured with SpeA-stimulated effector cells was then determined for each well=A.

$$\% \text{ Killing Capacity} = [1-(A/B)]*100 \qquad \text{Equation:}$$

In some experiments, a blocking antibody to Fas Ab (EMD Millipore) and FasL Ab (R&D) were co-cultured during the cytotoxicity assay.

ImageStream.

Images were acquired on a 2-camera ImageStream™ MkII imaging flow cytometer (Amnis, Seattle) with 60× objective and Inspire™ software version 200.1. The cytometer passed all ASSIST performance checks prior to image acquisition. FITC (Ch02, 480-560 nm), PE (Ch03, 560-595 nm) PE-CF594 (Ch04, 595-642 nm), PerCP-eFluor 710 (Ch05, 648-745 nm) and PE-Cy7 (Ch06, 745-780 nm) were excited at 488 nm (200 mW). BV421 (Ch07, 435-505 nm) and BV510 (Ch08, 505-570 nm) were excited at 405 nm (120 mW). APC (Ch11, 640-745 nm) and APC-eFluor 780 (Ch12, 745-780 nm) were excited at 642 nm (150 mW). 10,000 single, in-focus, dump-negative, CD3-positive events were acquired per sample. Data were compensated and analyzed with IDEAS™ software version 6.2 using the default masks and feature set.

ELISA.

Plasma from RT and non-RT children was tested for IgG, Streptolysin O (SLO) IgG and SpeA IgG. To determine IgG titer, human IgG antibody was coated (1:5000 dilution in PBS) overnight. To determine SLO IgG titer, recombinant Streptolysin O (Abcam) produced in *E. coli* was coated at 1 µg/mL. To determine SpeA IgG titer, recombinant SpeA (Toxin Technologies) was coated at 1 µg/mL. Plates were coated overnight at 4° C. PBS+0.05% Tween™ was used for all washes. Plates were blocked with PBS containing 0.2% Tween and 1% BSA at room temperature for 90 minutes. For IgG, human IgG was utilized as a standard. For SpeA and SLO, pooled plasma from normal healthy human donors was utilized as a standard to establish "relative units" of SpeA and SLO IgG in RT and non-RT plasma. As a secondary, a monoclonal mouse anti-human IgG antibody conjugated to HRP (Hybridoma Reagents Laboratory) was used.

Statistical Analysis.

All statistical analyses were performed using two-tailed Mann Whitney test using a nonparametric distribution in GraphPad™ 7.0, unless otherwise specified. Two-tailed Fisher exact test was determined using either GraphPad software or R software version 3.3.1.

Example 1

In this example, the inventors show that Tfh cells and GC B cells are significantly reduced in RT.

Figure 1B:
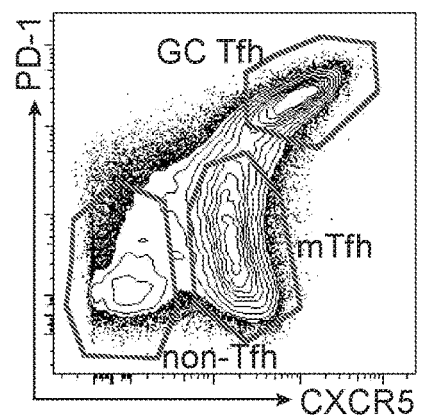
Figure 1C:
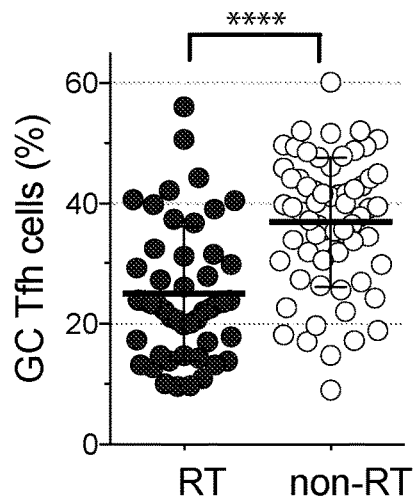
Figure 1D:
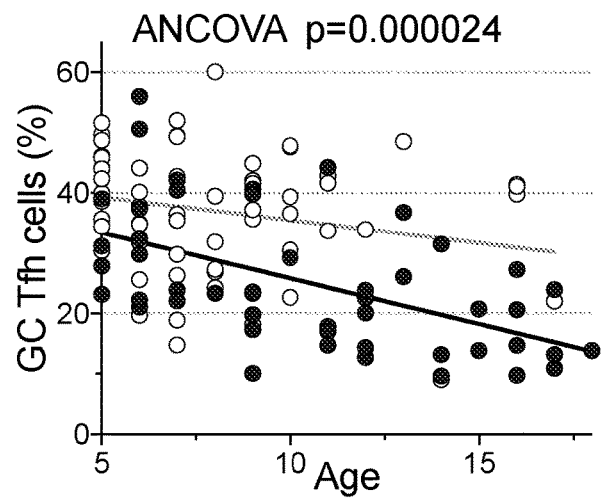
Figure 1E:
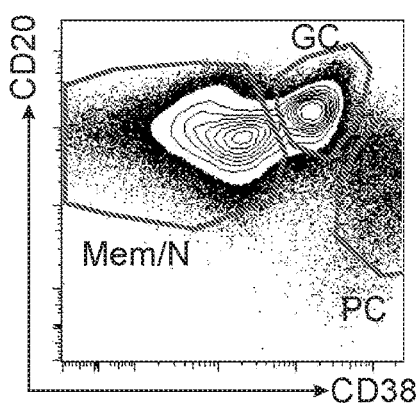
Figure 1F:
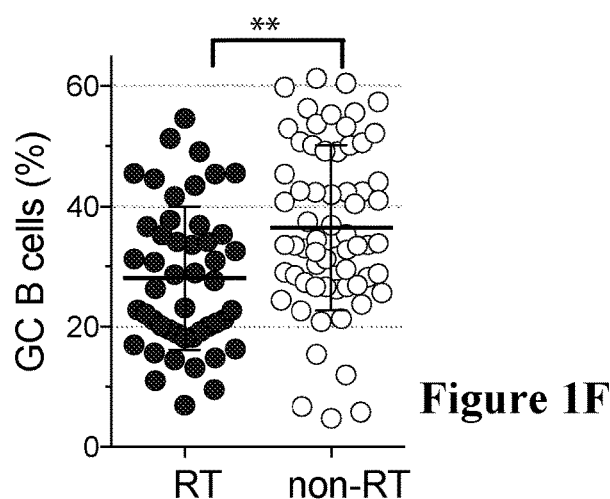
Figure 1G:
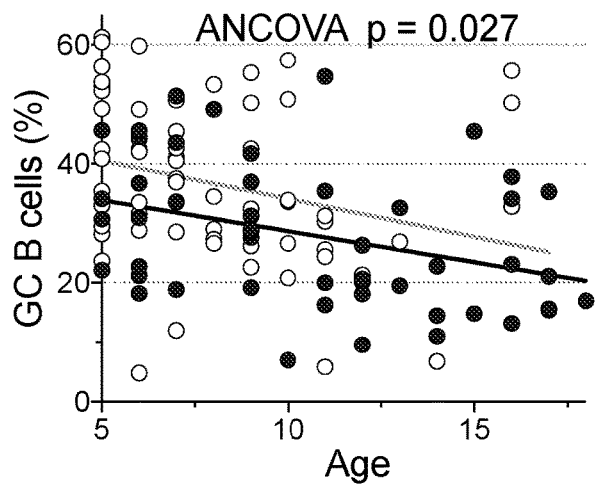
Figure 1H:
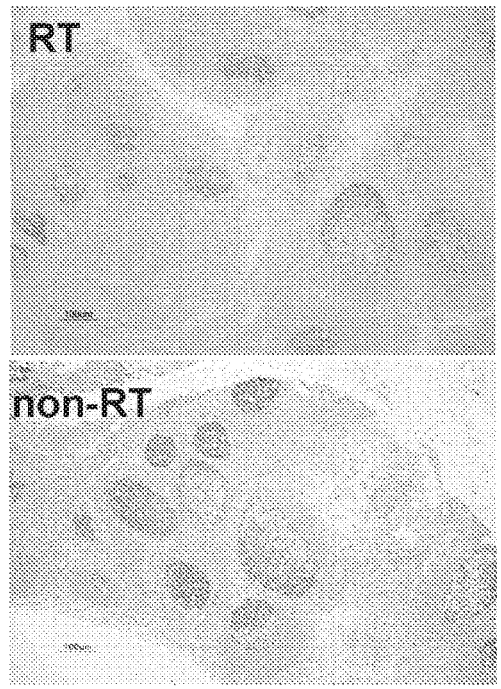
Figure 1I:
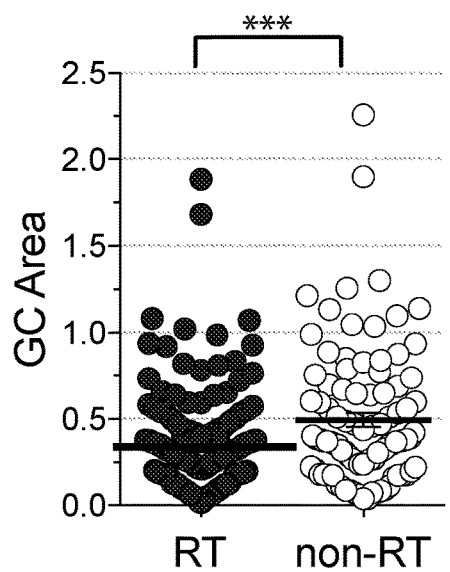
Figure 1J:
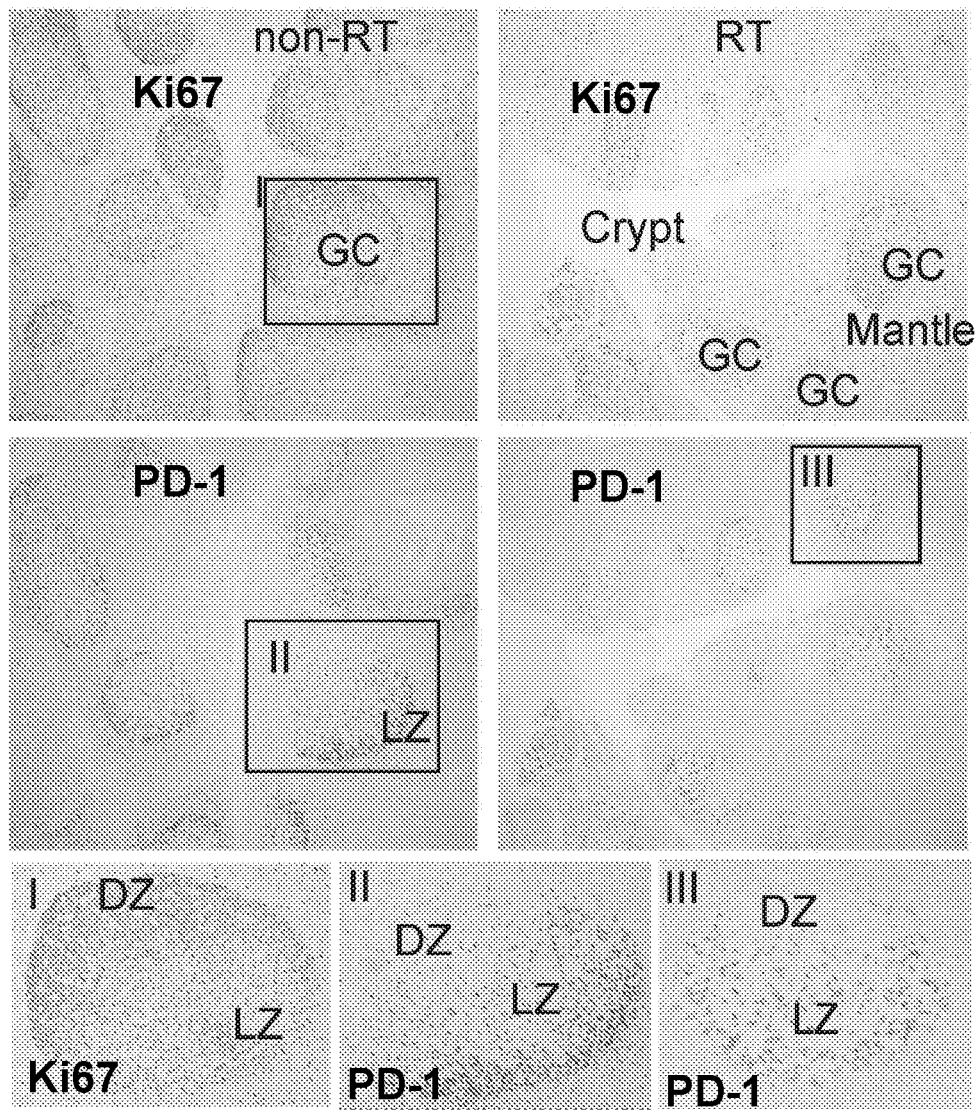

The following results are with respect to FIG. 1A to FIG. 1J. FIG. 1A shows the number of recurrent tonsillitis episodes. Flow cytometry results of GC Tfh (CXCR5$^{hi}$PD-1$^{hi}$CD45RO$^+$CD4$^+$), mTfh (CXCR5$^+$PD-1$^+$CD45RO$^+$CD4$^+$), and non-Tfh (CXCR5$^-$CD45RO$^+$CD4$^+$) cells are shown in FIG. 1B. RT tonsils (n=48) have significantly fewer GC Tfh cells than non-RT tonsils (n=64) (FIG. 1C). GC Tfh cells are quantified as % of total CD4$^+$ T cells. FIG. 1D shows GC Tfh cells by age. Flow cytometry results of GC B cells (CD38$^+$CD20$^+$CD19$^+$), plasma cells (CD38$^{hi}$CD20$^+$CD19$^+$), and memory (CD27$^{hi}$CD20$^+$CD19$^+$)/naive (CD27$^-$CD20$^+$CD19$^+$) B cells are shown in FIG. 1E. RT tonsils have significantly fewer GC B cells than non-RT tonsils. GC B cells are quantified as % of total B cells (FIG. 1F). FIG. 1G shows GC B cells by age. FIG. 1H shows representative Ki67 stained sections from RT and non-RT tonsils. FIG. 1I shows quantitation of GC areas (μm$^2$) in RT tonsils (n=21) and non-RT tonsils (n=16). Each data point represents an individual GC. FIG. 1J shows Staining of GC B cells (Ki67) and GC Tfh cells (PD-1). **=P<0.0001, *=P<0.001, **=P<0.01. Statistical significance determined by Mann-Whitney tests (a-c, e-f, i) and multivariate ANCOVA (FIGS. 1D and 1G).

Figure 7A:
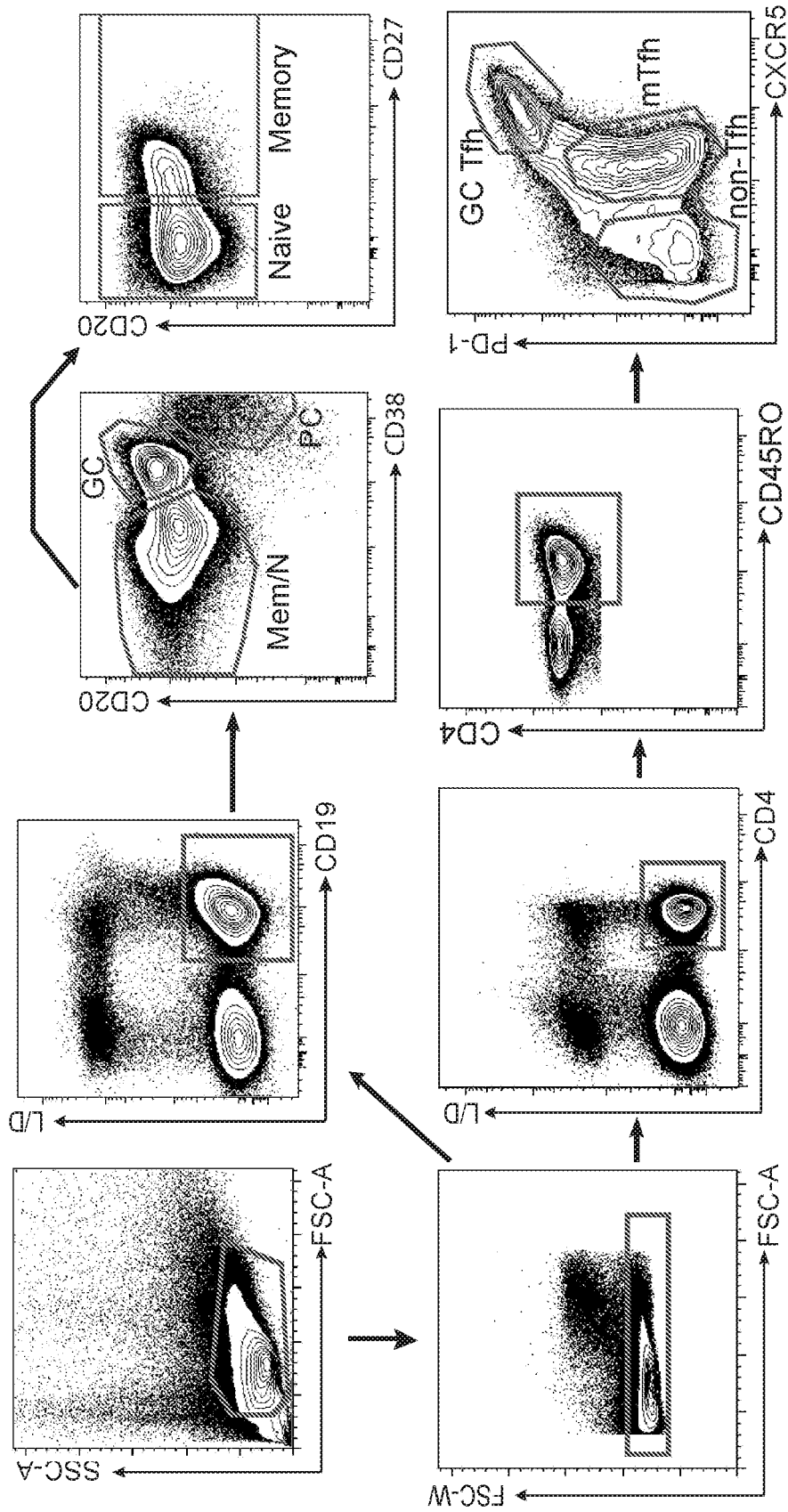
FIGS. 7A to 7H show immunophenotyping RT and non-RT tonsils in accordance with an embodiment of the present disclosure.
Figure 7B:
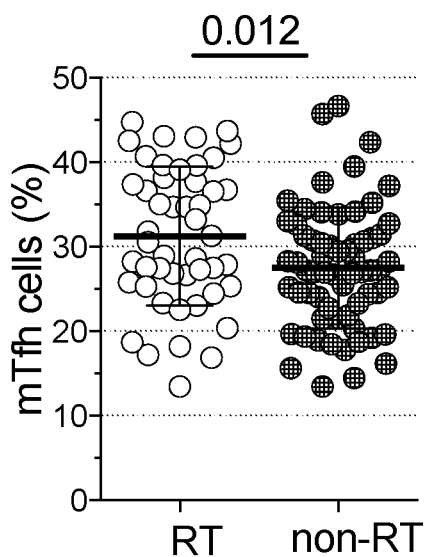
Figure 7C:
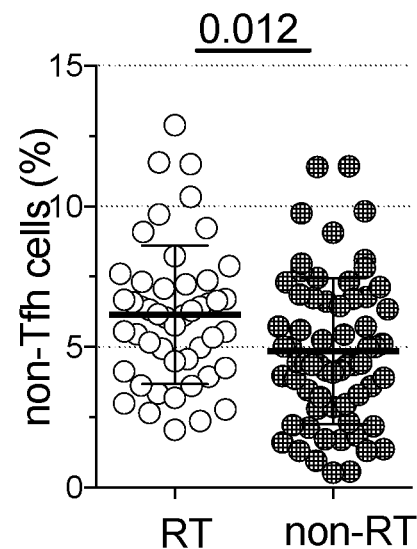
Figure 7D:
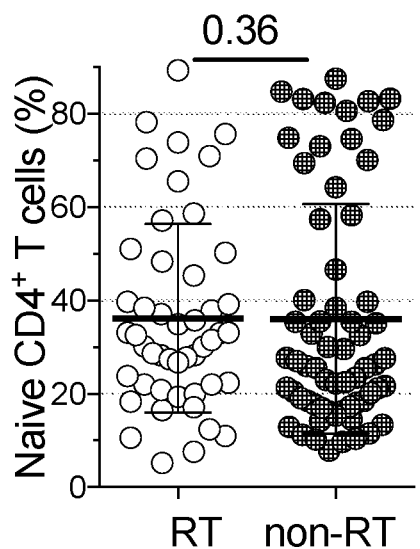
Figure 7E:
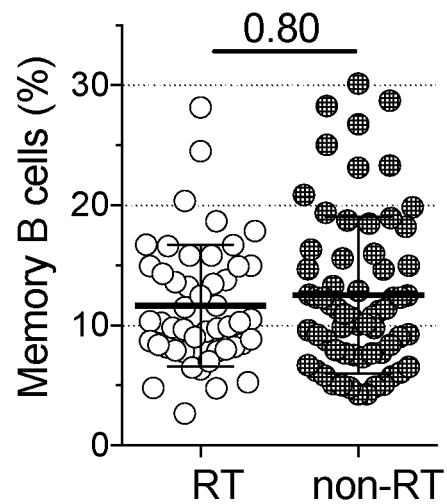
Figure 7F:
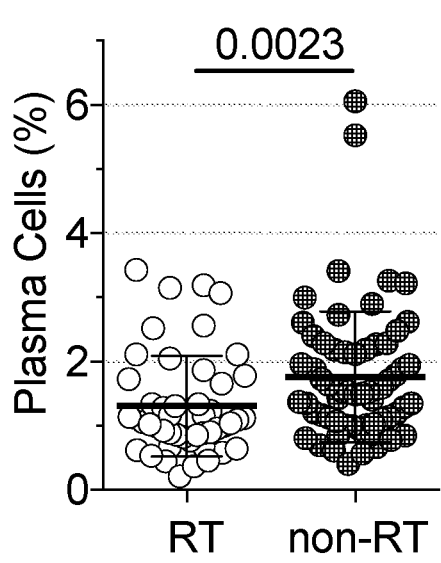
Figure 7G:
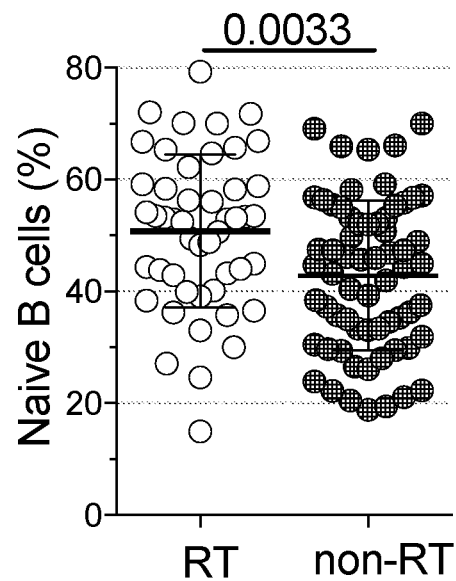
Figure 7H:
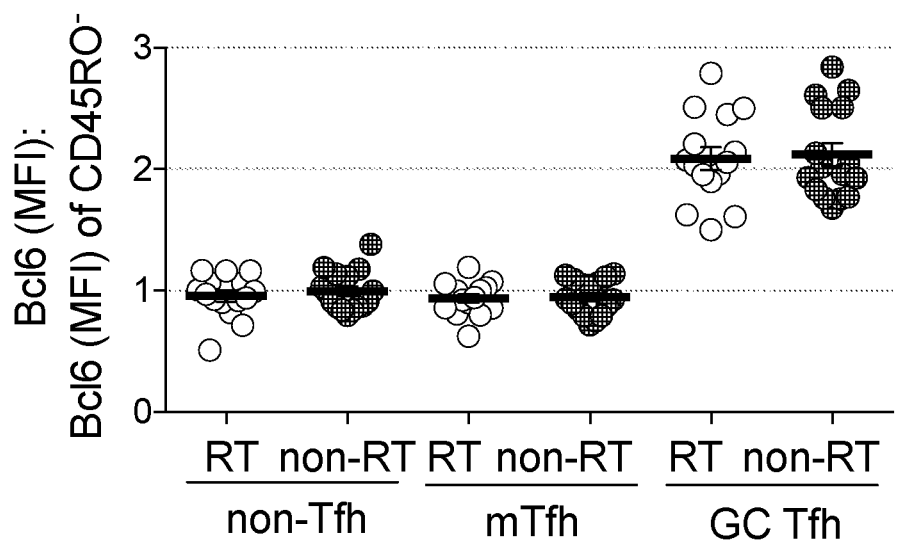

The following results are also with respect to FIG. 7A to FIG. 7H. FIG. 7A shows a gating strategy for tonsillar CD4$^+$ T cells and B cells. FIG. 7B shows that RT tonsils (n=48) have significantly more mTfh CD4$^+$ T cells (CXCR5$^+$PD-1$^+$ of CD45RO$^+$CD4$^+$) and FIG. 7C shows that non-Tfh CD4$^+$ T cells (CXCR5$^-$ of CD45RO$^+$CD4$^+$) than non-RT tonsils (n=64). mTfh and non-Tfh cells were gated on antigen-experienced (CD45RA$^-$CD4$^+$) T cells and normalized to CD4$^+$ T cells. FIG. 7D shows that there is no difference in frequency of naive (CD45RO$^-$) CD4$^+$ T cells. FIG. 7E shows that there is no difference in memory B cells (CD27$^+$ CD20$^{hi}$ of CD19$^+$). FIG. 7F shows that RT tonsils have significantly fewer plasma cells (CD38$^{hi}$CD20$^{hi}$ of CD19$^+$) than non-RT tonsils. FIG. 7G shows that there are significantly more naive B cells (CD27$^-$CD20$^+$ of CD19$^+$) in RT tonsils than non-RT tonsils. Statistical significance determined by Mann Whitney test. FIG. 7H shows that there is no difference in BCL6 expression by GC Tfh cells from RT (n=15) and non-RT tonsils (n=16), P=0.98. BCL6 MFI was quantified for GC Tfh, mTfh, non-Tfh, and CD45RO$^-$ (naïve) CD4$^+$ T cells. The MFI of BCL6 for GC Tfh, mTfh, and non-Tfh was then normalized to the MFI of BCL6 in CD45RO$^-$ CD4$^+$ T cells. Statistical significance determined by Mann-Whitney test (FIGS. 7B-7H).

RT can be a severe disease, resulting in substantial morbidity and school absences in hundreds of thousands of kids per year. By clinical history, the present inventors observed a mean of 12 tonsillitis episodes among RT children compared to 0.4 episodes among non-RT children (P=0.0001, FIG. 1A). RT and non-RT children have similar asymptomatic GAS carriage rates, ranging from 18-30%[9,14,15], suggesting that RT is not due to differences in GAS exposure. The present inventors systematically examined tonsillar leukocytes from RT and non-RT children. Forty-eight RT specimens and 64 non-RT specimens from children ages 5-18 were analyzed (Table 1).

TABLE 1

| Study participant demographics | | |
|---|---|---|
| | RT | Non-RT |
| Gender (%) | | |
| Female | 66% | 47% |
| Male | 34% | 53% |
| Age (mean years) | 10.02 | 8.54 |
| Tonsillitis Episodes (mean, Range) | 12.3 (4-24) | 0.45 (0-2) |
| Ethnicity (%) | | |
| Hispanic | 68% | 59% |
| Non-Hispanic | 32% | 41% |

Tonsils contain germinal centers, comprised of germinal center T follicular helper cells (GC Tfh), follicular dendritic cells (FDCs), and germinal center B (GC B) cells[16]. Tfh cells are the distinct type of CD4$^+$ T cell that provide help to B cells[17,18]. Tfh cells are required for germinal centers and thus almost all affinity matured antibody responses to pathogens[19]. Frequencies of GC Tfh cells (CD4$^+$CD45RO$^+$CXCR5$^{hi}$PD-1$^{int}$) were significantly reduced in tonsils from RT patients compared to non-RT patients (P<0.0001) (FIGS. 1B-1C and FIG. 7A). Non-Tfh (CXCR5$^{neg}$) and mantle Tfh (mTfh, CXCR5$^{int}$PD-1$^{int}$) cell frequencies were proportionally increased (P=0.012) (FIGS. 7B-7C), with no difference in naive CD4$^+$ T cells (FIG. 7D). BCL6 expression by GC Tfh cells was equivalent between the groups (FIG. 7H). Multivariate analysis demonstrated that the GC Tfh cell difference in RT patients was highly significant with or without age as a covariate (P=0.000024) (FIG. 1D).

GC Tfh cells instruct the survival, proliferation, and somatic hypermutation of GC B cells. Paralleling the significant reduction in GC Tfh cells, GC B cell frequencies were significantly lower in RT tonsils compared to non-RT tonsils (P=0.011, FIGS. 1E-1F; P=0.027, FIG. 1G and FIG. 7A), as were plasma cells (P=0.023) (FIG. 7F); memory B cell frequencies were unchanged (FIGS. 7A and 7E), while a higher frequency of naive B cells was present, commensurate with the reduced GC B cell frequency (P=0.0033) (FIGS. 7A and 7G).

Histological examination of tonsillar tissue revealed significantly smaller germinal centers in RT tonsils compared to non-RT tonsils (P<0.002, FIGS. 7H and 7I). Germinal center light and dark zones were well defined (FIG. 1J). Smaller germinal centers-consistent with the flow cytometry data-suggested a potential RT CD4$^+$ T cell defect. However, differences in GC Tfh cells and germinal centers could not be directly ascribed as RT-associated or non-RT-associated without additional information (see Methods, human subjects section); thus, the present inventors explored additional parameters that could establish whether the germinal center differences were RT disease-associated.

Example 2

Figure 2A:
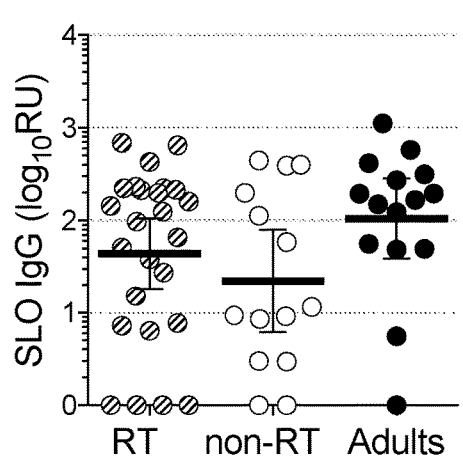
FIGS. 2A and 2B show that children with RT have significantly lower titers of circulating anti-SpeA IgG in accordance with an embodiment of the present disclosure.
Figure 2B:
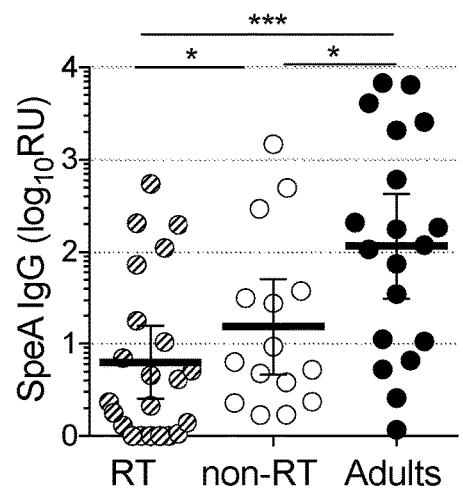

In this example, the inventors show that RT disease is associated with failure to develop anti-SpeA antibodies The following results are with respect to FIG. 2A and FIG. 2B. FIG. 2A shows that children with RT (n=25) have comparable anti-SLO IgG titers in circulation compared to children with non-RT (n=14) and normal healthy adults (n=15). Lines indicate GMTs. FIG. 2B shows that children with RT (n=22) have significantly reduced anti-SpeA IgG compared to children with non-RT (n=15) and normal healthy adults (n=19). Line indicates GMT, and GMTs are shown above each group. * P<0.05, *** P<0.001. Statistical significance determined by Mann-Whitney test.

Diminished germinal center activity could potentially result in impaired antibody responses to GAS. Examining plasma antibodies was necessary to test this possibility; however, blood samples are not normally taken during tonsillectomies. Thus, a new cohort of patients was recruited. Plasma antibody titers were examined against two GAS proteins: streptolysin O (SLO), the common GAS serodiagnostic antibody target, and streptococcal pyrogenic exotoxin A (SpeA), a crucial GAS virulence factor. RT patients might be expected to have higher plasma concentrations of GAS-specific antibodies than non-RT patients, since the former group experienced a tonsillitis episode within a few months prior to surgery, and have had a median of 12 bouts of tonsillitis (FIG. 1A). However, anti-SLO IgG titers were not elevated (P=0.38) (FIG. 2A). Even more strikingly, RT patients had significantly reduced anti-SpeA IgG titers, both when compared to non-RT patients (P=0.01) and healthy adult volunteers (P=0.0004) (FIG. 2B). Average anti-SpeA IgG titers in RT patients were only 5% that of healthy adult volunteers. A full 24% of RT patients had undetectable anti-SpeA IgG (FIG. 2B). Thus, these data indicate that impaired SpeA antibody responses are likely an attribute of RT disease, consistent with reduced germinal centers and GC Tfh deficits. SpeA antibodies have been implicated epidemiologically in protective immunity against severe systemic GAS infections[20-23], and SpeA antibodies can be protective in a mouse GAS infection model[24]. Impaired production of circulating anti-SpeA IgG in RT children suggests that these children have a GAS- and SpeA-specific germinal center defect, and that defect may be associated with RT patients' lack of protective immunity against recurrent GAS infections.

Example 3

In this example, the inventors show that RT patients have a deficit of GAS-specific GC Tfh cells.

Figure 3A:
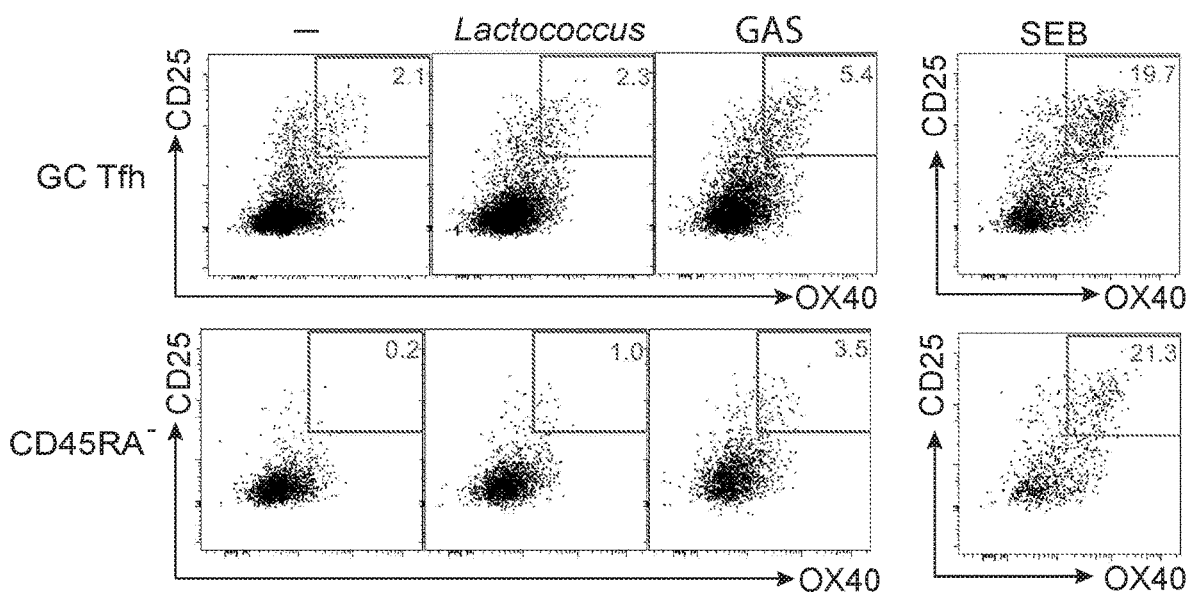
FIGS. 3A to 3D show that RT tonsils have increased GAS-specific Granzyme B+GC killer Tfh cells in accordance with an embodiment of the present disclosure.
Figure 3B:
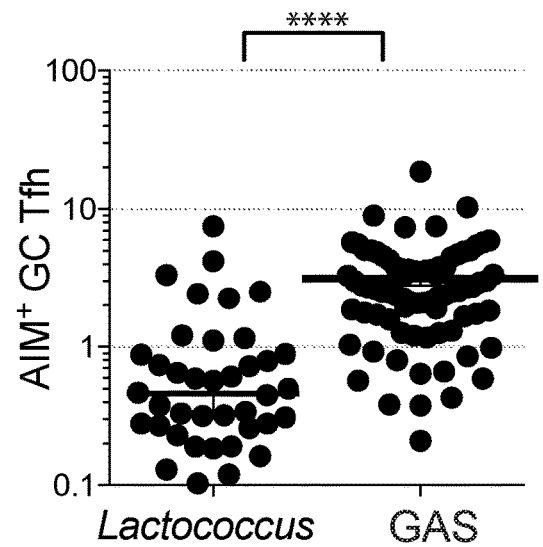
Figure 3C:
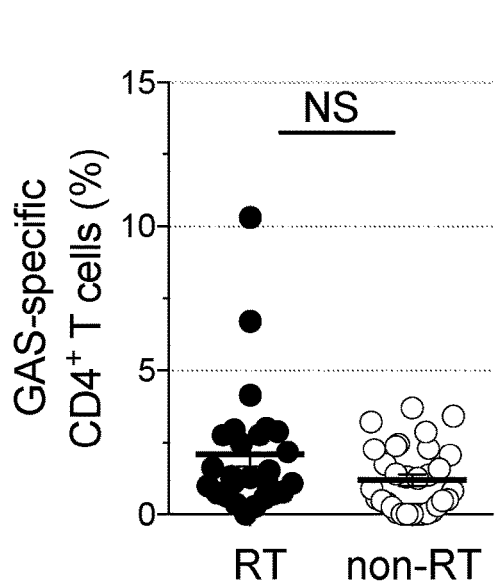
Figure 3D:
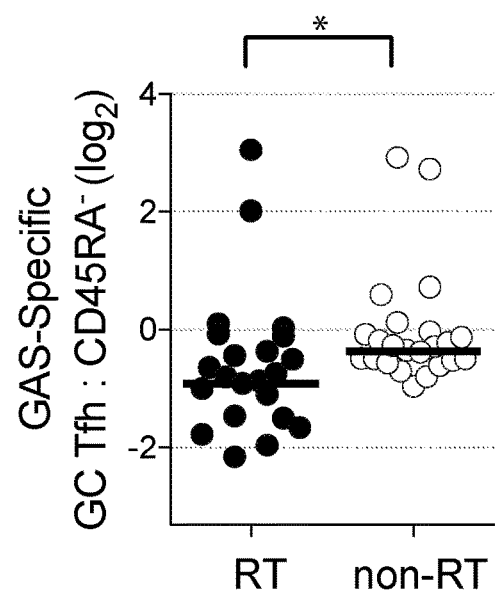

The following results are with respect to FIG. 3A to FIG. 3D. FIG. 3A shows flow cytometry identification of GAS-specific CD4+ T cells (CD45RA−) and GAS-specific GC Tfh cells (CD45RA−CXCR5$^{high}$PD-1$^{high}$) using an antigen-specific TCR-dependent activation induced marker (AIM) assay (OX40+CD25+). Tonsil cells were left unstimulated or stimulated with 10 µg/mL antibiotic-killed *Lactococcus lactis* (i.e., a non-pathogenic Gram positive bacteria which served as a negative control), 10 µg/mL heat-inactivated antibiotic-killed GAS, or 1 µg/mL staphylococcal enterotoxin B (SEB, positive control) for 18 hours. FIG. 3B shows that significantly more GAS-specific GC Tfh cells are detected by AIM (CD25+OX40+) compared to a negative control antigen. Cells were stimulated with heat-inactivated, antibiotic-killed GAS ('GAS') or antibiotic-killed *L. lactis* ('*Lactococcus*'). FIG. 3C shows that GAS-specific CD4+ T cell frequencies in RT and non-RT tonsils. FIG. 3D shows that RT tonsils have a significantly lower ratio of GAS-specific GC Tfh: total GAS-specific (CD45RA−) CD4+ T cells. **** P<0.0001, * P<0.05. Statistical significance determined by paired t-test (FIG. 3B) and Mann-Whitney tests (FIG. 3C-3D).

Figure 8A:
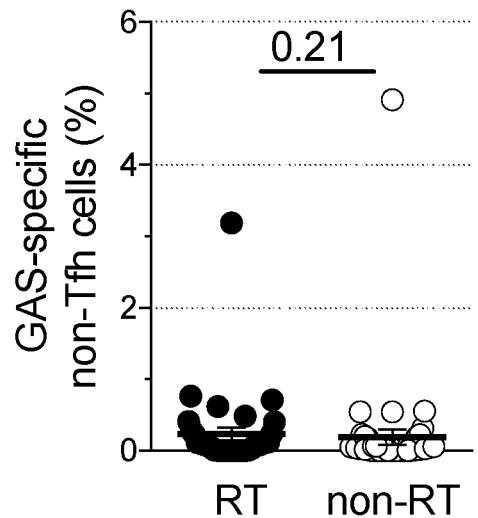
FIGS. 8A and 8B show GAS-specific $CD4^+$ T cells in RT and non-RT tonsils in accordance with an embodiment of the present disclosure.
Figure 8B:
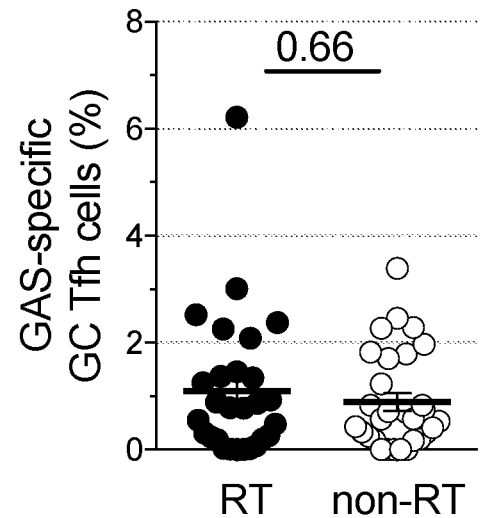

The following results are also with respect to FIGS. 8A and 8B. FIG. 8A shows that RT tonsils and non-RT tonsils contained comparable frequencies of GAS-specific non-Tfh cells. GAS-specific non-Tfh cells are quantified as % of total CD4+ T cells. FIG. 8B shows that RT tonsils and non-RT tonsils contained comparable frequencies of GAS-specific GC Tfh cells. GAS-specific GC Tfh cells are quantified as % of total CD4+ T cells. Statistical significance determined by Mann-Whitney test (FIGS. 8A-8B).

Phenotypic and histologic analyses of RT tonsils suggested a generalized impairment of CD4+ T cell help to B cells in RT disease. Without being bound by any particular theory, the present inventors reasoned that GAS disruption of GAS-specific GC Tfh cells could impact the development of antibodies against the pathogen, impairing protective immunity and predisposing to recurrent GAS infections. The present inventors, therefore, tested whether GAS-specific CD4+ T cell responses was affected in RT. Antigen-specific GC Tfh cells are difficult to identify due to their modest secretion of cytokines, as their major function is to provide help to adjacent GC B cells during cognate interactions. The present inventors, developed a cytokine-independent approach to identify antigen-specific GC Tfh cells using TCR-dependent activation-induced markers (AIM) expressed by CD4+ T cells upon recognition of antigen[25,26], and applied this AIM technique to quantify human GAS-specific CD4+ T cells (FIG. 3A). The non-pathogenic Gram-positive bacterium *Lactococcus lactis* was used as a negative control (FIGS. 3A-3B). With RT patients experiencing 12 times more tonsillitis episodes than non-RT patients (FIG. 1A), and the most recent tonsillitis episode for each RT patient being only a few months prior to tonsillectomy, a simple expectation was that RT tonsils would have significantly more GAS-specific CD4+ T cells than non-RT tonsils. However, experiments revealed that frequencies of GAS-specific CD4+ T cells were not elevated in RT cases compared to non-RT cases (FIG. 3C, FIGS. 8A-8B). In fact, GAS-specific CD4+ T cells from RT patients were skewed away from GC Tfh differentiation (P=0.025) (FIG. 3D). Taken together, these data suggested that GAS-specific GC Tfh cell responses were disrupted in RT disease.

Example 4

In this example, the inventors show that RT disease is associated with HLA Class II alleles.

The following results are with respect to FIG. 4A to FIG. 4C. FIG. 4A shows the family history of tonsillectomy. A significantly greater proportion of RT children have a family history of tonsillectomy than non-RT children. RT=71, non-RT=63. FIG. 4B shows that HLA DQB1*06:02 alleles were present at a higher frequency in non-RT patients (checkered bar, n=192) compared to RT patients (white bar, n=138). HLA DQB1*06:02 alleles were present at a significantly higher frequency in the general population (black bar, n=242) and non-RT patients+general population (striped bar, n=434) compared to RT patients. FIG. 4C shows that RT patients with the lowest quartile of germinal center activity, defined as lowest combined frequencies of GC Tfh and GC B cells (left panel. Dots with vertical dashes, n=15. GC$^{lo}$), have a significantly higher frequency of HLA DRB1*01:01 and HLA DRB1*07:01 alleles compared to non-RT tonsils (n=190), general population (n=246), and general population+ non-RT tonsils (n=436). RT patients HLA allele counts (white bar, n=30). *** P<0.001, * P<0.05. Statistical significance determined by Fisher Exact test (FIGS. 4A-4C).

Figure 9A:
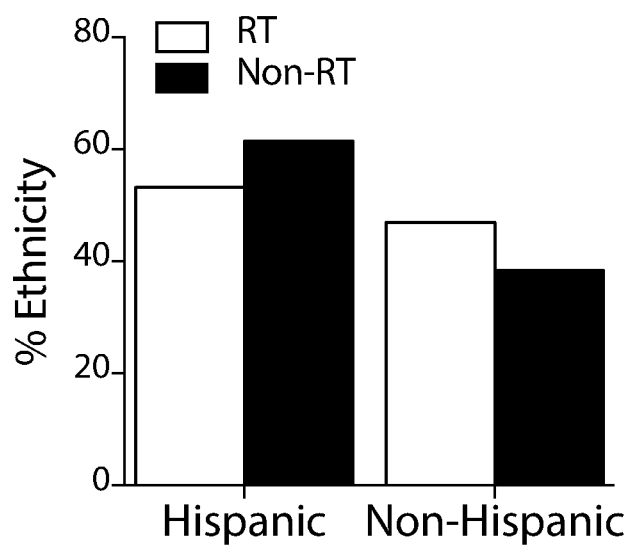

The following results are also with respect to FIG. 9A and FIG. 9B. FIG. 9A shows the percentage of Hispanic and non-Hispanics among children with RT and non-RT. FIG. 9B shows the allelic frequencies in RT, non-RT, GP, and GP+ non-RT individuals for HLA class II alleles of interest. P values represent comparison between RT and non-RT, RT and GP, and RT and GP+ non-RT.

Essentially all children are infected with GAS during childhood[27]. Analysis of this clinical cohort demonstrated a significant family history of tonsillectomy for children with RT (P=0.0004) (FIG. 4A). This was suggestive of a genetic predisposition for RT. A robust germinal center response depends on HLA Class II antigen presentation by B cells to GC Tfh cells. The present inventors, thus, performed HLA typing of the cohort. HLA DQB1*06:02 was significantly less frequent in RT patients than ethnically matched healthy adults from the San Diego general population (P=0.042) and combined controls (P=0.048) (FIG. 4B, and FIGS. 9A-9B). No allelic frequency difference was noted between non-RT patients and general population controls (P=0.89) (FIG. 4B, FIG. 9B). These data were consistent with the HLA association being specific for RT. Susceptibility to toxic shock syndrome and invasive forms of GAS infection have been inversely associated with HLA class II DQB1*06:02[28], and protection from the development of rheumatic heart disease[29,30]. Overall, these data indicate that HLA allele DQB1*0602 is a putative 'protective' allele for RT disease.

HLA alleles DRB1*01:01[30,31] and DRB1*07:01[29,32-34] have been previously linked to risk of autoimmune rheumatic heart disease, the most severe sequela of long-term untreated RT and the leading cause of heart failure in children worldwide[1,35]. No significant DRB1*01:01 and DRB1*07:01 allelic associations were observed for the full RT cohort (FIG. 9B). However, the present inventors also considered that genetic association with susceptibility may be strongest in patients with the most severely impaired germinal center responses. Therefore, HLA allelic frequencies were examined among the RT patients with the lowest quartile of germinal center responses (FIG. 4C, FIG. 9B, $GC^{lo}$). These patients had significantly higher frequencies of HLA DRB1*01:01 compared to non-RT children (P=0.049), the general population (P=0.034), and the combined control groups (P=0.031) (FIG. 4C, FIG. 9B). Patients with the most severely impaired germinal center responses also had significantly higher frequencies of HLA DRB1*07:01 compared to non-RT children (P=0.029) and the combined control groups (P=0.034) (FIG. 4C, FIG. 9B). In contrast, no differences were identified between the non-RT and general population cohort for HLA DRB1*01:01 (P=0.85) or HLA DRB1*07:01 (P=0.74) (FIG. 4C, FIG. 9B). These data indicate that HLA DRB1*01:01 and DRB1*07:01 are 'at risk' alleles for RT. Furthermore, the combination of immunophenotyping, clinical data, GAS serum antibody titers, and HLA typing revealed significant relationships between RT disease, reduced antibody responses, fewer GC Tfh cells, smaller germinal centers, and GAS.

Example 5

In this example, the inventors show that RT-associated HLA alleles differentially impact CD4+ T cell responses to GAS and the GAS superantigen SpeA.

Figure 5A:
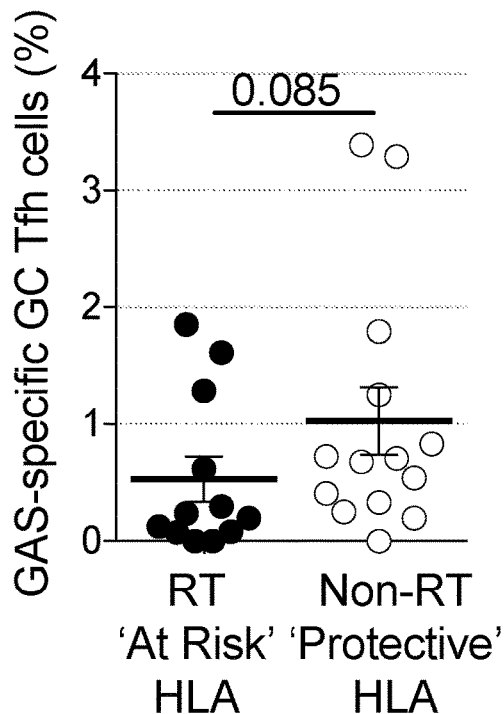
FIGS. 5A to 5E show HLA associations identified in RT and non-RT patients segregate based on preferential GAS superantigen SpeA binding in accordance with an embodiment of the present disclosure.
Figure 5B:
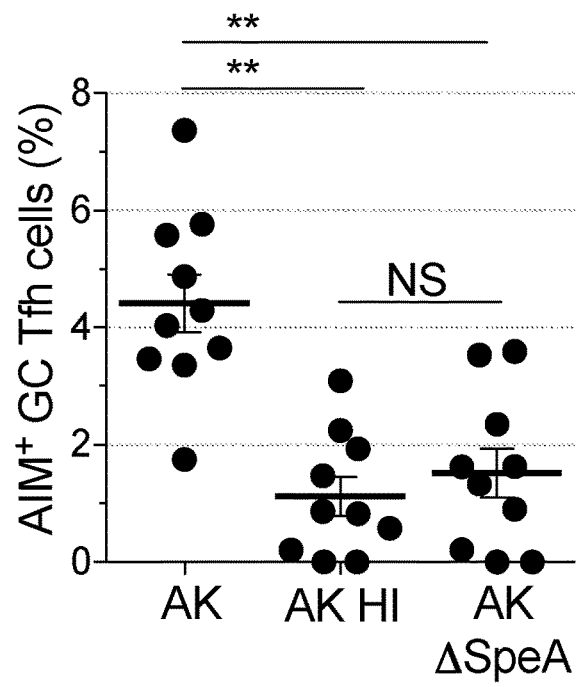
Figure 5C:
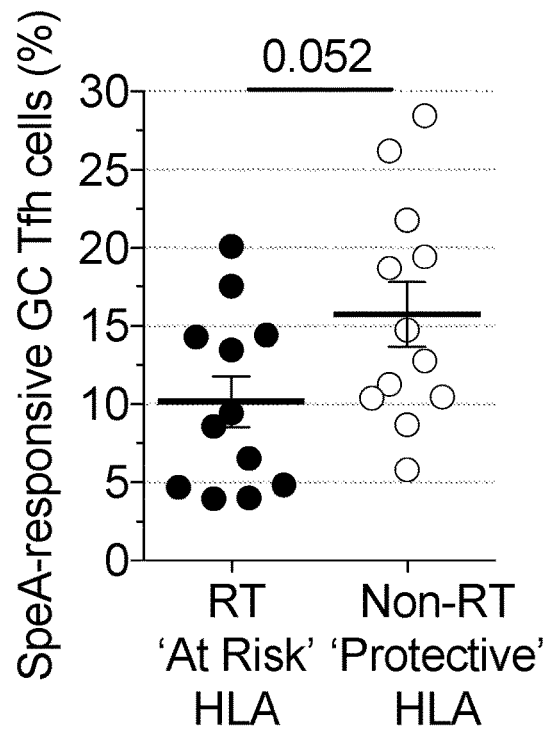
Figure 5D:
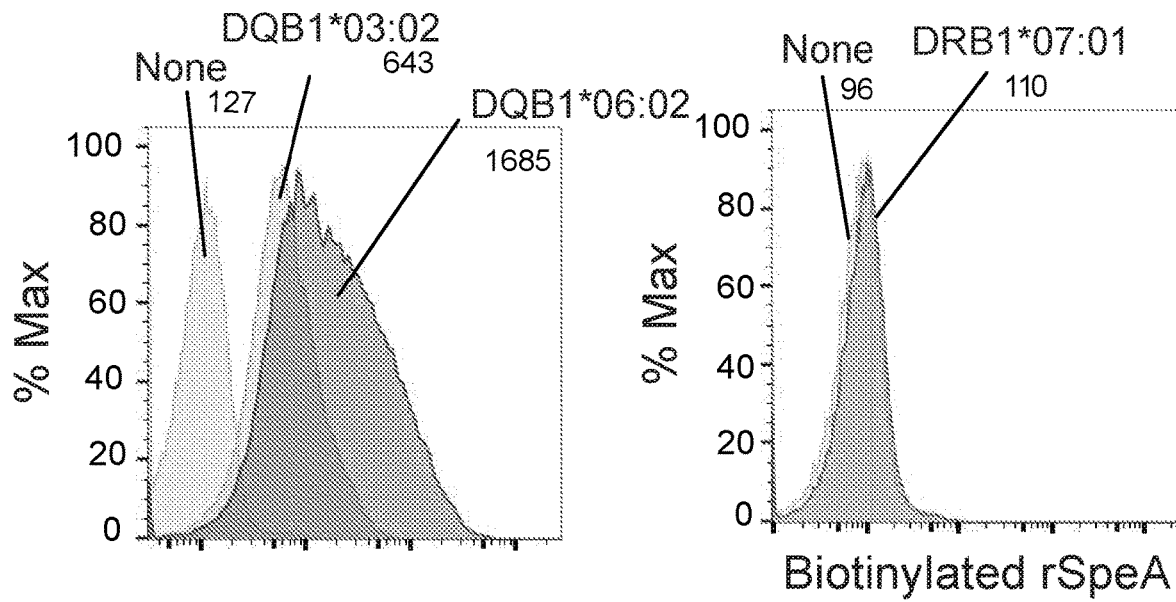
Figure 5E:
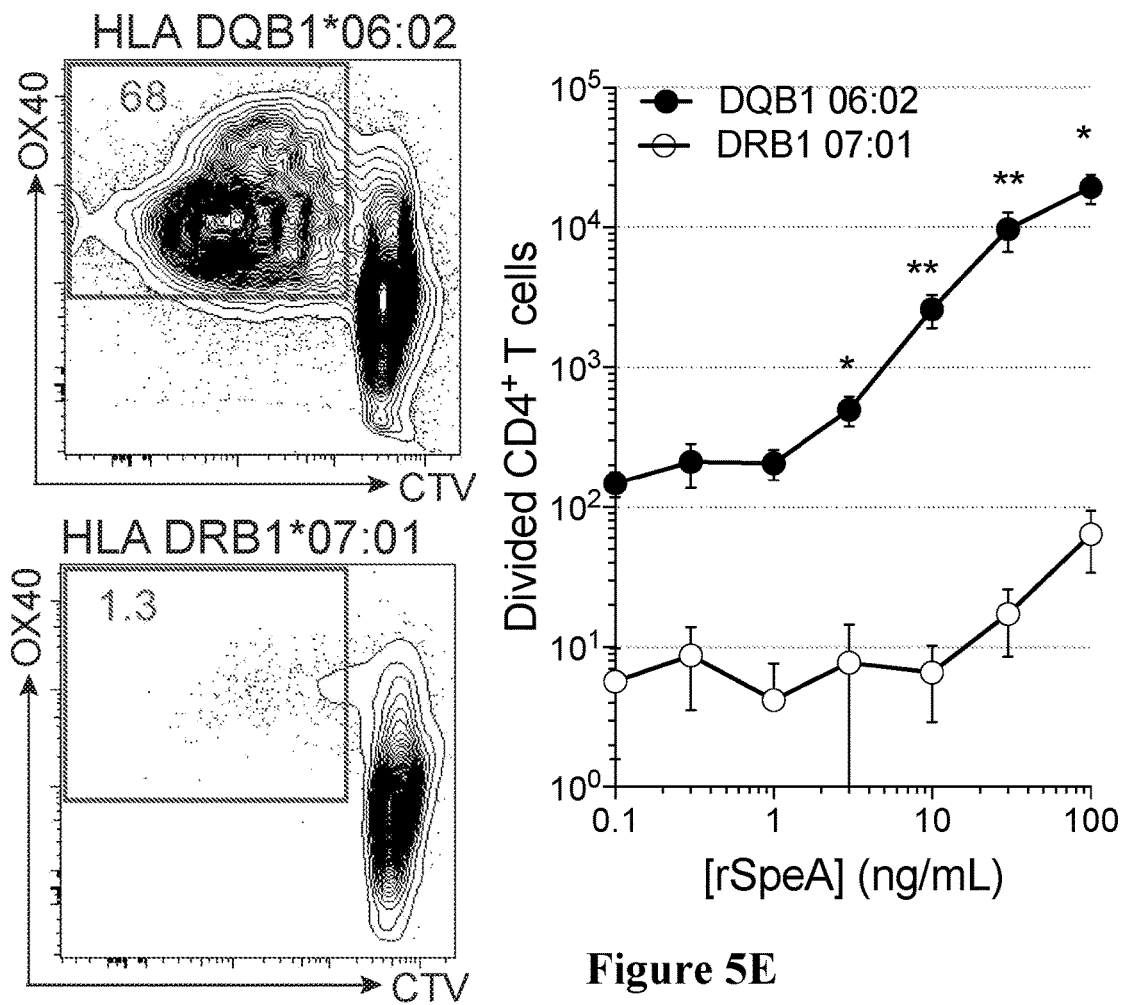

The following results are with respect to FIG. 5A to FIG. 5E. FIG. 5A shows that RT patients with either HLA DRB1*01:01 or HLA DRB1*07:01 (n=12) have fewer GAS-specific GC Tfh cells compared to non-RT patients with HLA DQB1*06:02 (n=14), though not statistically significant, p=0.084. Each percentage was background subtracted from unstimulated GC Tfh cells. FIG. 5B shows a comparison of activated (AIM+) GC Tfh cells following stimulation with either 10 µg/mL antibiotic-killed GAS (AK), 10 µg/mL antibiotic-killed, heat-inactivated GAS (AK HI), or 10 µg/mL antibiotic-killed SpeA deficient GAS (AK ΔSpeA), n=10. FIG. 5C shows that RT patients with the 'At Risk' HLA (n=12) have fewer SpeA-responsive GC Tfh cells compared to non-RT patients with the 'Protective' HLA (n=12), P=0.052. Tonsils cells were stimulated with 1 g/mL SpeA for 18 hours and background subtracted from unstimulated cells. FIG. 5D shows a histogram flow cytometric quantitation of SpeA binding. Biotinylated SpeA binds preferentially to HLA DQB1*06:02>DQB1*03:02>DRB1*07:01, N=3 experiments. FIG. 5E shows that magnetically sorted total CD4+ T cells from PBMCs of HLA DQB1*06:02+ donors, co-cultured with SpeA and a cell line expressing HLA DQB1*06:02 proliferated significantly more compared to CD4+ T cells from PBMCs of HLA DRB1*07:01+ donors, co-cultured with SpeA (recombinant SpeA, rSpeA) and a cell line expressing HLA DRB1*07:01. N=4 experiments. ** P<0.01, * P<0.05 (FIG. 5E). Statistical significance determined by Mann Whitney test.

Figure 10A:
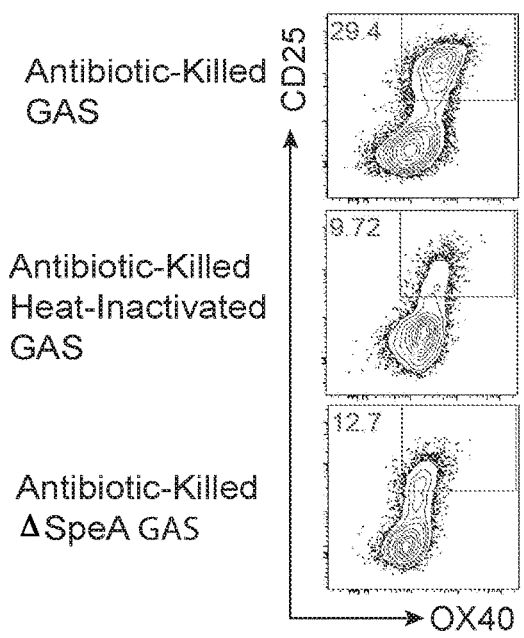
FIGS. 10A to 10E show results with respect to SpeA-responsive Granzyme B+GC killer Tfh cells in accordance with an embodiment of the present disclosure.
Figure 10B:
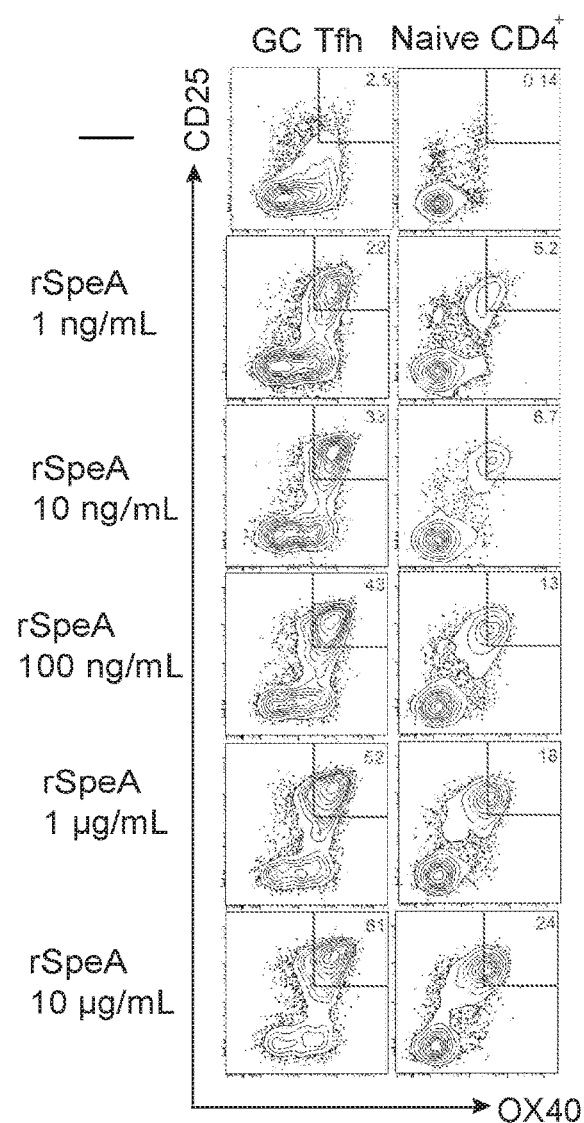
Figure 10C:
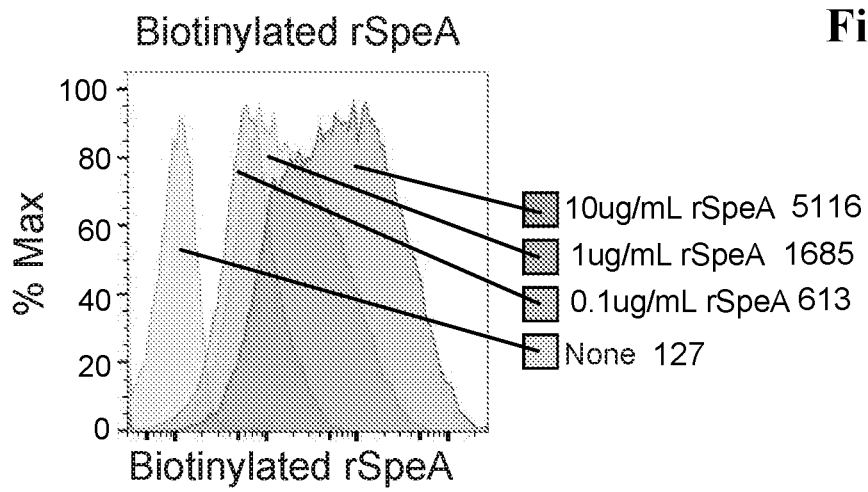
Figure 10D:
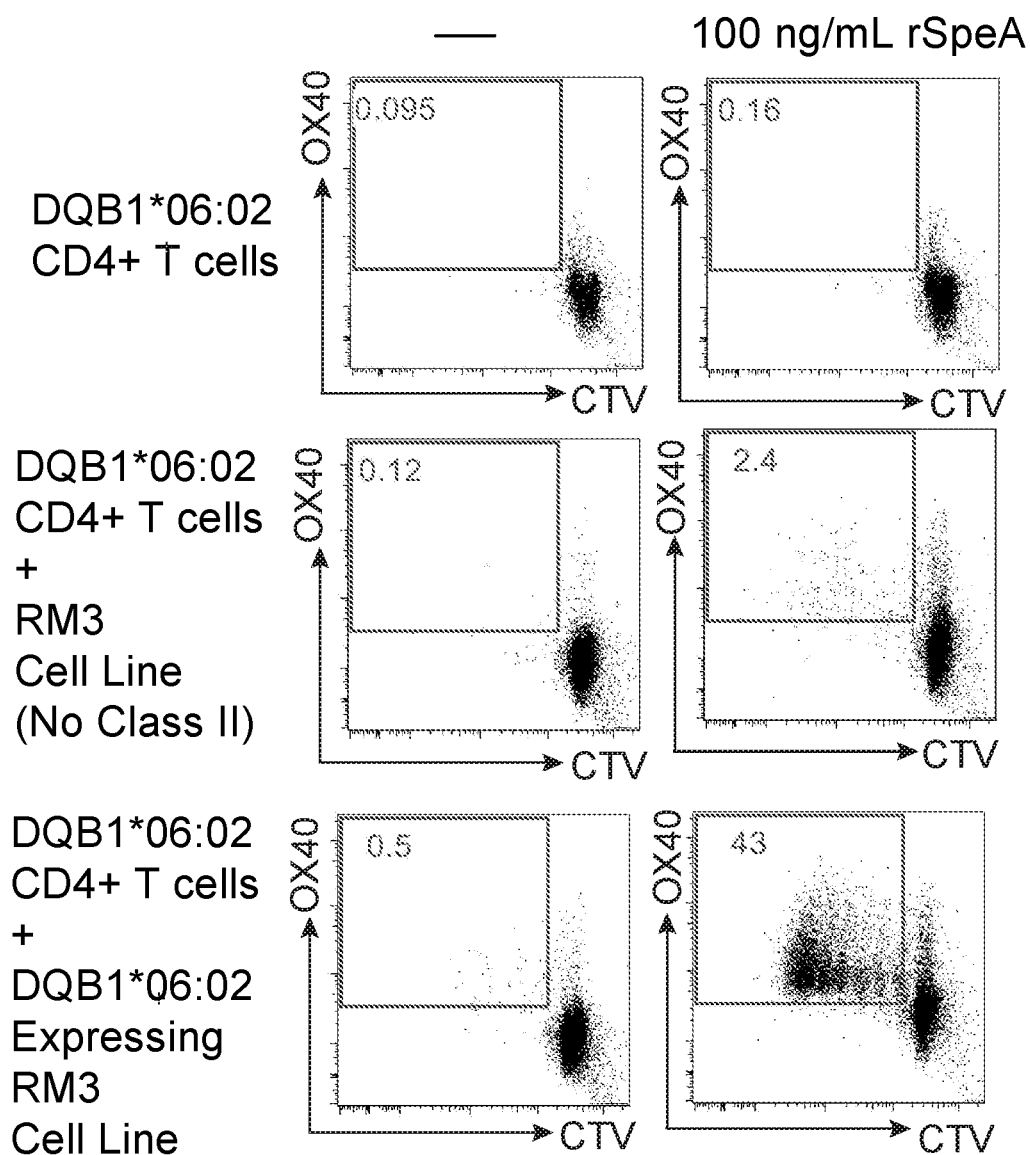
Figure 10E:
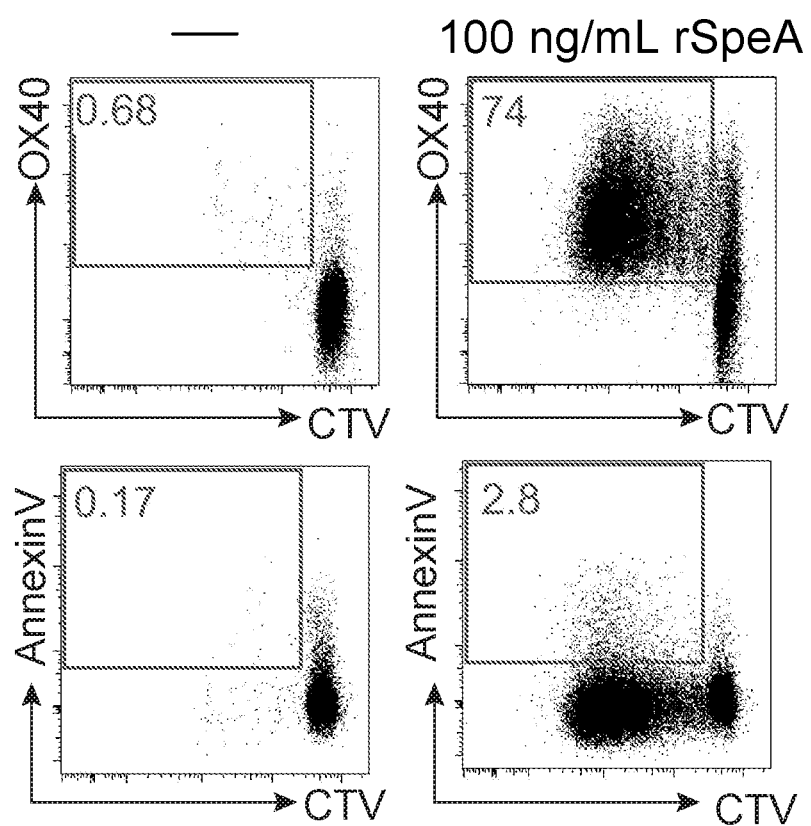

The following results are also with respect to FIG. 10A to FIG. 10E. FIG. 10A shows that flow cytometry gating of activated (AIM+) GC Tfh cells following stimulation with antibiotic-killed GAS, heat-inactivated antibiotic-killed GAS and antibiotic-killed GAS lacking SpeA. FIG. 10B shows a dose response of GC Tfh cells and naive CD4+ T cells to SpeA. FIG. 10C shows a dose-dependent binding of biotinylated SpeA (recombinant SpeA, rSpeA) to an RM3 cell line expressing HLA DQB1*06:02. FIG. 10D shows flow cytometry plots of unstimulated and SpeA-stimulated HLA DQB1*06:02 CD4+ T cells alone (top panel), HLA DQB1*06:02 CD4+ T cells co-cultured with the RM3 cell line, and HLA DQB1*06:02 CD4+ T cells co-cultured with the RM3 cell line expressing DQB1*06:02. FIG. 10E shows flow cytometry plots of unstimulated and SpeA-stimulated DQB1*06:02 CD4+ T cells co-cultured with an RM3 cell line expressing HLA DQB1*06:02 and subsequently stained with Annexin V. There is minimal Annexin V expression by SpeA-responsive CD4+ T cells. ** P<0.01. Statistical significance determined by Mann-Whitney test.

The present inventors next evaluated CD4+ T cell responses to GAS in 'at risk' RT tonsils by AIM. RT tonsils possessing 'at risk' HLA class II alleles had reduced GAS-specific GC Tfh cells compared to non-RT tonsils possessing the protective HLA DQ B1*06:02 allele (P=0.085) (FIG. 5A). SpeA superantigen is an important GAS virulence factor. Comparison of CD4+ T cell reactivity using an antibiotic-killed wild-type (WT) GAS strain with or without heat inactivation, or an antibiotic-killed isogenic SpeA-deficient mutant GAS strain (ΔrpeA), demonstrated that SpeA superantigen-mediated stimulation of CD4+ T cells constituted a major fraction of CD4+ T cell reactivity to GAS (P=0.002) (FIG. 5B, FIG. 10A). SpeA has provided GAS with an evolutionary advantage[24,36,37], allowing for the global persistence and dominance of the SpeA+ M1 serotype among throat cultures, with the M1 serotype detected in ~92% of throat cultures[38-41]. Given the HLA class II associations the present inventors identified between RT and GAS-specific GC Tfh cells, the present inventors tested whether SpeA may differentially influence tonsillar CD4+ T cells. GC Tfh cells from RT tonsils with an 'at risk' HLA allele were less responsive to SpeA stimulation than non-RT tonsils with the 'protective' HLA allele (P=0.052) (FIG. 5C, FIG. 10B). Mechanistic relationships between HLA class II alleles and GAS disease manifestations are unclear[35], but a potential role has been suggested for SpeA[28,42,43]. The present inventors, therefore, directly tested binding of SpeA to 19 well-defined single-allele HLA class II expressing cell lines. The highest affinity interaction occurred between SpeA and HLA DQB1*06:02 (FIG. 5D, FIG. 10C). Next, the present inventors examined the effects of SpeA on CD4+ T cells. Rapid and robust proliferation of HLA DQB1*06:02+ CD4+ T cells was observed in the presence of the superantigen (P=0.0079) (FIG. 5E, FIGS. 10D-10E). In contrast, minimal proliferation was observed for HLA DQB1*06:02 CD4+ T cells, including HLA DRB1*01:01+ or DRB1*07:01+ cells (FIG. 5E and data not shown). Thus, this data shows that a very high affinity interaction of GAS SpeA with HLA DQB1*06:02 (FIGS. 5D-5E) is associated with a lower risk of DQB1*06:02+ individuals for RT (FIG. 4B).

Example 6

In this example, the inventors show that Granzyme B+ GC Tfh cells are found in RT disease.

The following results are with respect to FIG. 6A to FIG. 6I. FIG. 6A shows a volcano plot showing fold change of genes in SpeA-stimulated GC Tfh cells from RT tonsils (n=5) compared to SpeA-stimulated GC Tfh cells from non-RT tonsils (n=5). 76 genes exhibited a <2-fold change and P<0.1, and 75 genes with >2-fold change and P<0.1. FIG. 6B (top) shows the intracellular granzyme B expression (%) by GC Tfh cells by flow cytometry. Tonsil cells were stimulated with 1 g/mL SpeA for 24 hours. FIG. 6B (bottom) shows backgating of the granzyme B+ GC Tfh cells among total CD45RA− CD4+ T cells. FIG. 6C shows that SpeA stimulation revealed significantly more granzyme B+ GC Tfh cells in RT tonsils (n=20) compared to non-RT tonsils (n=17). FIG. 6D shows that SpeA stimulated GC Tfh cells co-expressed granzyme B and perforin. FACS sorted GC Tfh cells and autologous B cells were cultured+/− SpeA for 5 days and stained for granzyme B and perforin expression. N=3 donors. FIG. 6E shows ImageStream cytometry plot of granzyme B+ GC Tfh cells following SpeA stimulation. GC Tfh cells were gated as CXCR5$^{hi}$PD-1$^{hi}$ of live CD45RA−CD4+ T cells. FIG. 6F shows ImageStream imaging of GC Tfh cells following SpeA stimulation, showing representative granzyme B− and granzyme B+ cells. FIG. 6G shows confocal microscopy of a granzyme B+ CD4+ T cell in a germinal center in an RT tonsil (*). A granzyme B+ CD8+ T cell is also shown for reference (<). FIG. 6H shows that SpeA-stimulated GC Tfh cells are able to kill B cells. GC Tfh cells (CXCR5$^{hi}$PD-1$^{hi}$CD45RA−CD4+) were co-cultured with autologous CTV-labeled B cells (CD19+ CD38−). Killing was quantified as outlined in the Methods, with controls shown in FIGS. 12G-12K. N=15 RT and 11 non-RT donors. FIG. 6I shows Granzyme B expression (%) by GC Tfh cells from healthy lymph nodes and RT and non-RT tonsils. SpeA-stimulated GC Tfh cells from RT tonsils (N=11) expressed more granzyme B compared to SpeA-stimulated GC Tfh cells from non-RT tonsils (n=11) or healthy lymph nodes (n=4). ** P<0.01, * P<0.05. Statistical significance determined by Mann-Whitney test (FIGS. 6C, 6H and 6I).

Figure 11A:
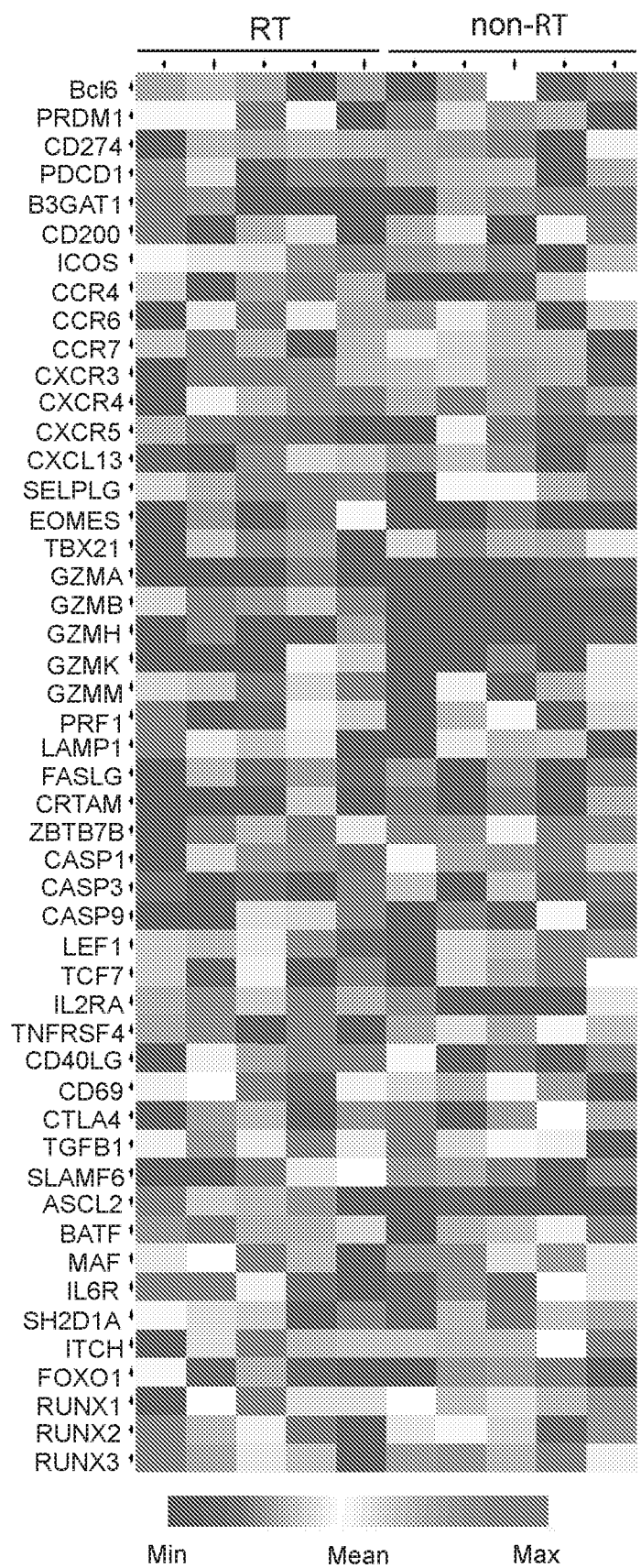

The following results are also with respect to FIG. 11A and FIG. 11B. FIG. 11A shows a heat map of gene expression changes of signature CD4+ T cell differentiation and function associated genes by GC Tfh cells upon stimulation with SpeA (AIM+ cells). (n=5 RT, n=5 non-RT). FIG. 11B shows the comparison of granzyme B RNA-seq counts by CD4+ T cells from normal lymph nodes and blood, unstimulated GC Tfh cells, GAS-specific GC Tfh cells (AIM+), and SpeA-responsive GC Tfh cells (AIM+) by RT tonsils and non-RT tonsils. SpeA-responsive GC Tfh cells from RT tonsils expressed significantly more granzyme B RNA than non-RT tonsils. ** P<0.01. Statistical significance determined by Mann-Whitney test.

Figure 12D:
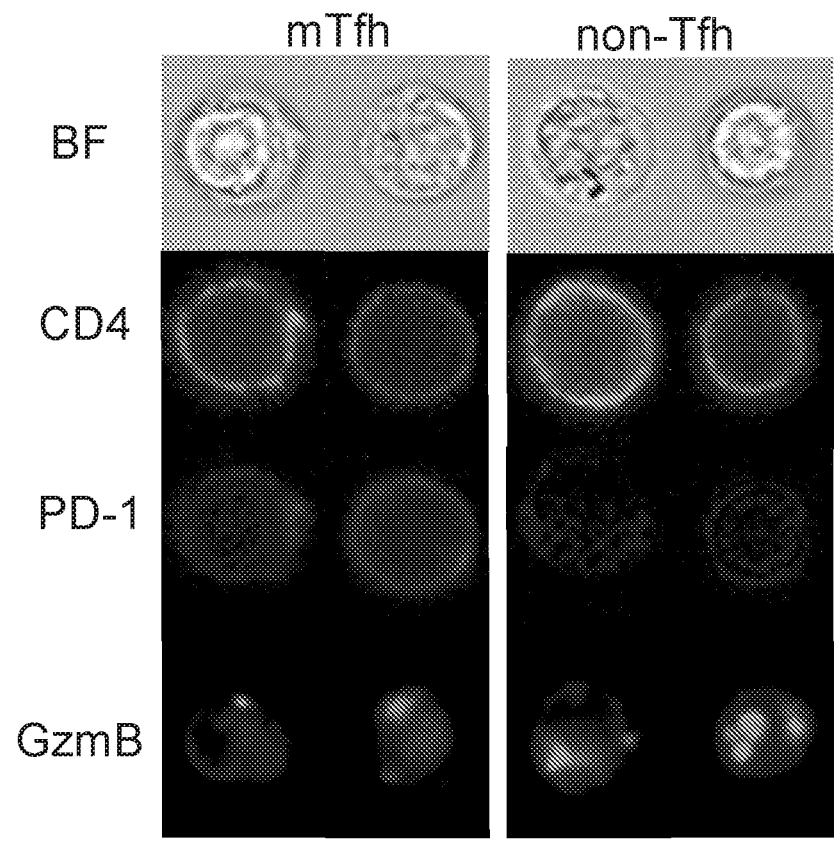
Figure 12E:
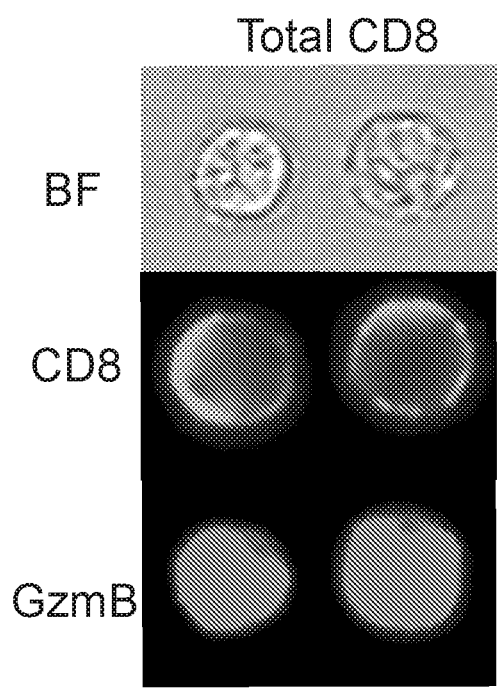
Figure 12F:
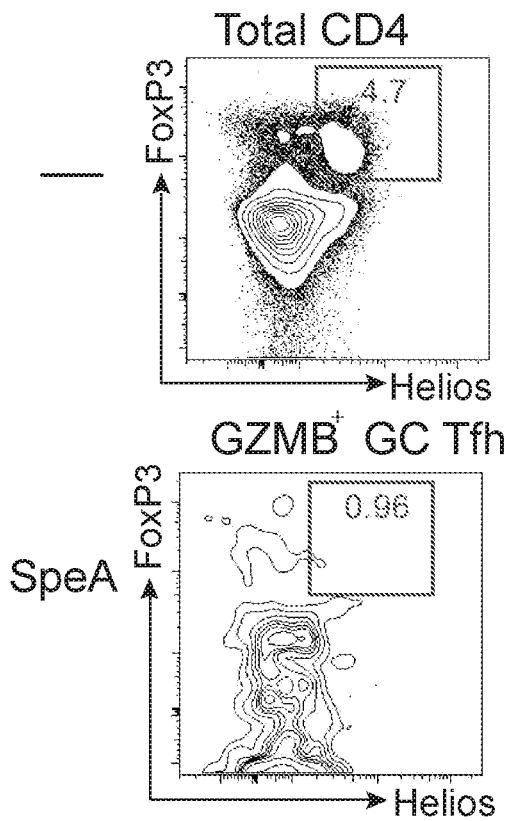
Figure 12G:
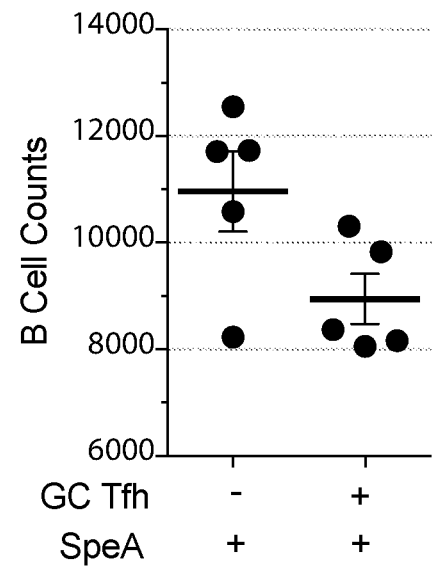
Figure 12H:
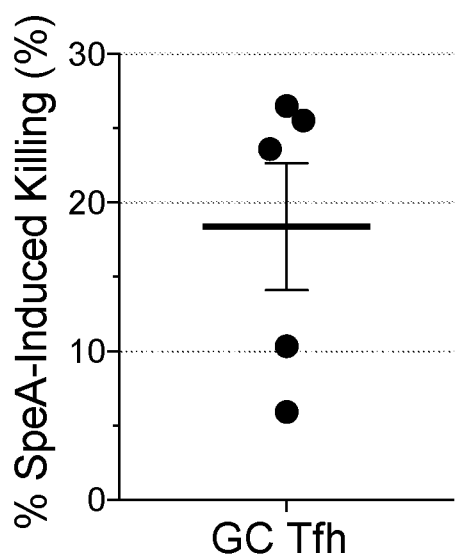
Figure 12I:
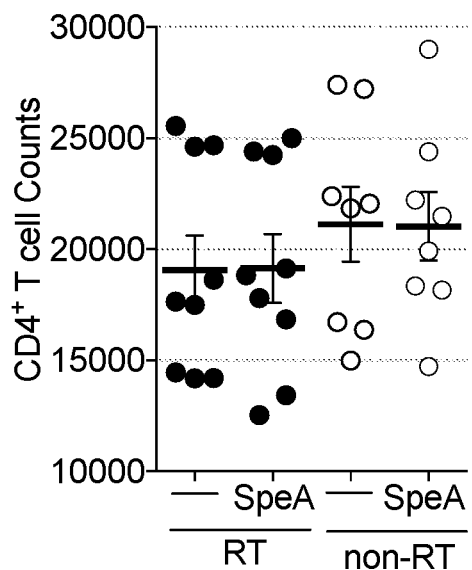
Figure 12J:
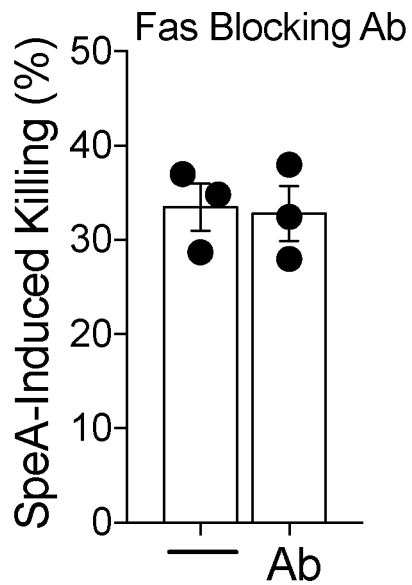
Figure 12K:
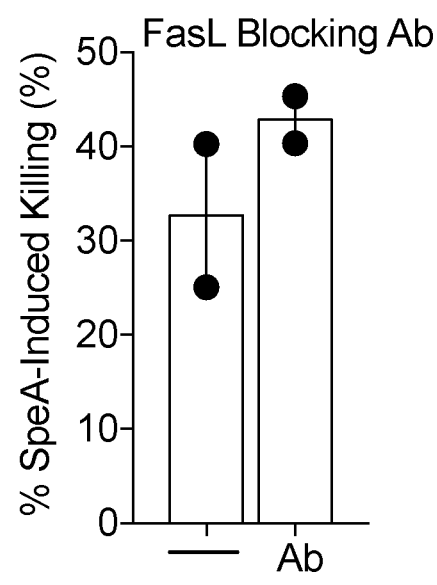
Figure 12L:
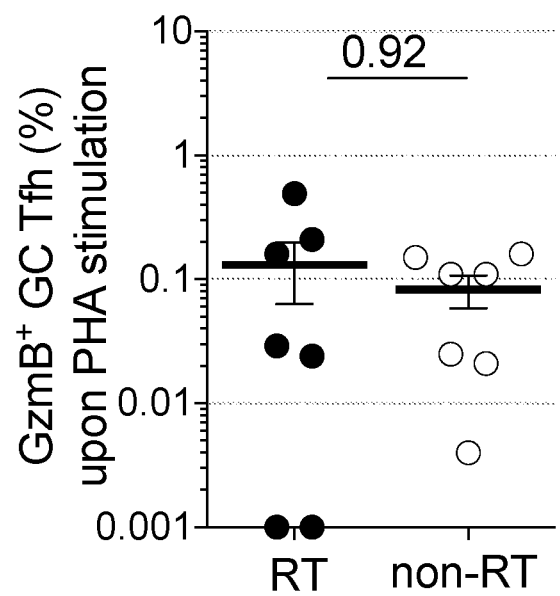

The following results are also with respect to FIG. 12A to FIG. 12L. Granzyme B expression by (FIG. 12A) mTfh cells, (FIG. 12B) non-Tfh cells, and (FIG. 12C) CD8+ T cells from RT tonsils and non-RT tonsils following SpeA stimulation, as measured by flow cytometry. FIG. 12D shows ImageStream examples of granzyme B expression by SpeA-responsive mTfh cells, non-Tfh cells, and FIG. 12E of CD8+ T cells from an RT tonsil. FIG. 12F shows the percentage of T follicular regulatory (Tfr) cells (FoxP3+ Helios+) from unstimulated total CD4+ T cells, SpeA-stimulated total CD4+ T cells, and granzyme B+GC Tfh cells. FIG. 12G shows the B cell counts following 40 h co-culture with GC Tfh cells, unstimulated or stimulated with SpeA. B cell death was not observed in the absence of SpeA stimulation. A representative donor is shown. FIG. 12H shows SpeA-induced cytotoxicity by GC Tfh (CXCR5hiPD-1hiCD45RA-CD4+) from the same donor as in FIG. 12G of autologous non-GC B cells (CD19+CD38−). FIG. 12I shows the cell counts of remaining GC Tfh cells following co-culture with B cells, left unstimulated or stimulated with SpeA. GC Tfh cells from 8 RT and 8 non-RT are shown. GC Tfh cell fratricide was not observed. FIGS. 12J and 12K, respectively, show that monoclonal antibodies blocking Fas or FasL did not inhibit the SpeA-induced GC Tfh cell killing of B cells. FIG. 12L shows minimal granzyme B+GC Tfh cells observed following stimulation with PHA. RT and non-RT. Statistical significance determined by Mann-Whitney test.

To identify CD4+ T cell factors that may cause RT germinal center abnormalities via a SpeA superantigen-dependent mechanism, the present inventors performed RNA sequencing (RNA-seq) transcriptomic analysis of SpeA-stimulated GC Tfh cells, using GC Tfh cells purified from RT and non-RT tonsils following SpeA stimulation No RT-associated mRNA changes were observed for signature GC Tfh cell genes before or after stimulation (FIG. 11A). Strikingly, GZMB mRNA, encoding the cytotoxic effector protein granzyme B, was dramatically upregulated in RT GC Tfh cells (P<0.0079) (FIG. 6A, FIG. 5B). Granzyme B is a secreted protein highly expressed by cytotoxic CD8+ T cells and is a major effector molecule of CD8+ T cell killing of target cells. Expression of granzyme B by GC Tfh cells in RT patients is contrary to the B cell help function of GC Tfh cells. Aberrant granzyme B expression by GC Tfh cells in RT tonsils may result in reprogramming of a GC Tfh cell from one that helps GC B cells to one that kills GC B cells, potentially explaining how GAS may divert the immune response in RT to cause smaller germinal centers.

RNA-seq analysis performed of gene expression by SpeA stimulated GC Tfh cells from RT tonsils compared to non-RT tonsils is presented in Table 2 and Table 3 below as reads per kilobase of transcript per million mapped reads (RPKM). Gene expression by SpeA stimulated GC Tfh cells is plotted against P values (RT over non-RT tonsils) relative to fold change in (RT over non-RT tonsils).

TABLE 2

| Gene | Fold Change | P-value |
| --- | --- | --- |
| GZMB | 7.641012092 | 4.59E−05 |
| LOC284385 | 2.317810397 | 0.002559366 |
| PPOX | 2.218139609 | 0.002785651 |
| SNTB1 | 2.296645977 | 0.003729742 |
| DCLRE1B | 2.150753657 | 0.005042583 |
| CDT1 | 2.480776303 | 0.009692611 |
| LOC100128420 | 3.079868872 | 0.010444279 |
| WEE1 | 3.335473996 | 0.011568611 |
| NUF2 | 2.994568266 | 0.012846426 |
| DECR2 | 2.316402308 | 0.013369701 |
| PKIA | 2.224832426 | 0.014374529 |
| LGALS1 | 2.184116223 | 0.017846288 |
| SLC35E3 | 2.040700451 | 0.020975003 |
| UBOX5 | 2.068927748 | 0.021686391 |
| IL22 | 3.055735984 | 0.023171022 |
| C4orf34 | 2.071640813 | 0.02426651 |
| MZB1 | 2.476828678 | 0.025647493 |
| KLF3 | 2.080842079 | 0.025762039 |
| SCGB3A1 | 2.994882237 | 0.026494406 |
| RPPH1 | 2.467434663 | 0.030118042 |
| ATF7IP2 | 2.054984595 | 0.03198134 |
| CENPW | 4.133223197 | 0.032880987 |
| PAGE5 | 2.67613822 | 0.033396207 |
| UBE2C | 2.224833707 | 0.036300563 |
| IMPA2 | 2.417129555 | 0.038225742 |
| MAD2L1 | 2.828229429 | 0.038561592 |
| TPX2 | 2.498344606 | 0.040002708 |
| GRAP2 | 2.963261168 | 0.040914453 |
| AURKA | 2.520344445 | 0.041535268 |
| BUB1 | 2.020926143 | 0.042653122 |
| CENPK | 2.522201984 | 0.044391545 |
| DEPDC1B | 2.280002346 | 0.046123652 |
| CDC20 | 2.203022094 | 0.046429125 |
| NAPSB | 2.047931039 | 0.05148833 |
| ZNF155 | 2.564138295 | 0.057275938 |
| POLR3G | 2.024205673 | 0.063231312 |
| BIRC5 | 2.060498011 | 0.065009278 |
| ZNF367 | 2.33910587 | 0.068694987 |
| ZADH2 | 2.188883403 | 0.069122086 |
| PANK3 | 2.219992474 | 0.071876863 |
| HES4 | 2.025890893 | 0.083303056 |
| CCL28 | 2.951966957 | 0.084301037 |
| SLA2 | 2.232905509 | 0.08607985 |
| KIAA0101 | 2.697930082 | 0.086727426 |
| TIMP1 | 2.12029238 | 0.089767548 |
| MS4A1 | 2.050547847 | 0.092444783 |
| PTPN22 | 2.492185037 | 0.093908842 |
| PYCARD | 2.09885381 | 0.095960315 |
| ERAP2 | 2.327480291 | 0.09698552 |
| PDIA5 | 2.17676995 | 0.098763327 |

TABLE 3

| Gene | Fold Change | P-value |
| --- | --- | --- |
| SNORA20 | 0.219296741 | 6.86E−04 |
| LZTFL1 | 0.407304672 | 0.001213133 |
| SNORA29 | 0.24175469 | 0.00164243 |
| SERTAD3 | 0.317708017 | 0.004597311 |
| SNORD50A | 0.285222272 | 0.005097441 |
| ZNF468 | 0.443980171 | 0.008219553 |
| CCDC64 | 0.466200146 | 0.009384882 |
| SNORD56 | 0.316767722 | 0.010037785 |
| LOC100507217 | 0.477196454 | 0.010294377 |
| SNORA24 | 0.17610984 | 0.010422507 |
| PABPC1L | 0.421650144 | 0.010641913 |
| ZNF616 | 0.450959584 | 0.010884979 |
| TSPAN12 | 0.365231965 | 0.011161333 |
| ZNF79 | 0.376680402 | 0.013191762 |
| TAC1 | 0.296441433 | 0.01440709 |
| PON3 | 0.450586281 | 0.014425667 |
| CAV1 | 0.386177054 | 0.014875716 |
| STK39 | 0.400496892 | 0.020831134 |
| ZNF582 | 0.349598263 | 0.021525763 |
| SNORD59B | 0.24883353 | 0.024130146 |
| C11orf96 | 0.45170587 | 0.025603799 |
| HLA-DRB5 | 0.319043215 | 0.0305416 |
| ZCCHC11 | 0.44333271 | 0.031315628 |
| FGL2 | 0.488200331 | 0.032907045 |
| TRIM24 | 0.479570725 | 0.035403023 |
| SGCE | 0.428370999 | 0.035905141 |
| ZNF600 | 0.375312948 | 0.036229017 |
| BEX5 | 0.438532397 | 0.040577234 |
| MIR1322 | 0.486818912 | 0.043176712 |
| TP53BP1 | 0.498082342 | 0.04757955 |
| ZNF193 | 0.469979672 | 0.048261952 |
| MYO6 | 0.468293495 | 0.051242255 |
| SPRYD7 | 0.438181147 | 0.057517773 |
| HACE1 | 0.468504172 | 0.057639005 |
| MIR1204 | 0.30467294 | 0.060005741 |
| LINC00467 | 0.450750221 | 0.060299993 |
| LOC100506713 | 0.499940492 | 0.06359757 |
| UTS2 | 0.244531668 | 0.063861328 |
| MIR3128 | 0.391822063 | 0.064393945 |
| ECHDC2 | 0.486166254 | 0.067159481 |
| MIR4434 | 0.338995038 | 0.067435871 |
| SNORA64 | 0.335854109 | 0.06784237 |
| LRCH3 | 0.483478566 | 0.068098779 |
| ZCCHC4 | 0.483444356 | 0.071369221 |
| IFITM3 | 0.254985075 | 0.07588393 |
| LOC100506668 | 0.479312519 | 0.07763664 |
| FAAH | 0.49772865 | 0.078759892 |
| NNAT | 0.363155402 | 0.085979177 |
| RWDD3 | 0.434290161 | 0.087550555 |
| C7orf25 | 0.41965916 | 0.099025109 |

To determine if RT GC Tfh cells are capable of granzyme B protein expression, four independent approaches were used: (1) flow cytometry of intracellular stained stimulated GC Tfh cells, (2) ImageStream imaging cytometry of stimulated GC Tfh cells, (3) immunofluorescence microscopy of human tonsillar tissue, and (4) killing of target cells. GC Tfh cell intracellular protein staining confirmed granzyme B expression specifically induced by GAS SpeA stimulation (P=0.009) (FIGS. 6B-6D). Perforin expression was also induced by SpeA stimulation (FIG. 6D). Consistent with these findings, punctate cytoplasmic granzyme B was observed by ImageStream imaging cytometry in GC Tfh cells of RT patients stimulated with SpeA (FIGS. 6E and 6F). These changes were specific to GC Tfh cells, as there were no differences in the frequencies of granzyme B+ mTfh, non-Tfh, or CD8+ T cells between RT and non-RT donors (FIGS. 12A-12E). The granzyme B+ GC Tfh cells were not Tregs (FIG. 12F). Granzyme B was observed histologically in putative CD8+ T cells (CD4) and in rare GC Tfh cells (FIG. 6G).

Three additional experimental analyses were done of the granzyme B+ GC Tfh cells. The present inventors first assessed whether SpeA-stimulated GC Tfh cells were capable of killing B cells. Killing of B cells by GC Tfh cells was observed in the presence of SpeA (FIG. 6H, FIGS. 12G and 12H). This killing was significantly higher in RT tonsils compared to non-RT tonsils. Bystander cell death was not observed (FIG. 12I). These findings were consistent with the granzyme B+ GC Tfh cells acting as cytolytic GC Tfh cells instead of helper cells. The B cell killing was independent of Fas and FasL (FIGS. 12J and 12K), and was associated with perforin expression (FIG. 6D).

The present inventors then assessed the selectivity of GAS SpeA for induction of granzyme B expression by GC Tfh cells. The present inventors observed no difference in granzyme B expression between GC Tfh from RT and non-RT patients after stimulation with the strong mitogenic agent PHA (FIG. 12L). These data indicate that SpeA was important for aberrant development of granzyme B$^+$ GC Tfh cells.

Lastly, the present inventors assessed whether granzyme B$^+$ GC Tfh cells were unique to RT. Healthy lymph nodes (LN) from patients undergoing a staging LN biopsy were utilized as comparators to RT and non-RT tonsils. Granzyme B$^+$ GC Tfh cells were sporadically detected in healthy LNs, demonstrating these cells are not unique to RT. Nevertheless, significantly more granzyme B$^+$ GC Tfh cells were observed in the context of RT disease than healthy LN GC Tfh cells, specifically upon SpeA stimulation (P=0.025), while GC Tfh cells from non-RT tonsils and healthy LNs were indistinguishable (FIG. 6I). Collectively these data demonstrate that SpeA is capable of deviating GC Tfh cells into granzyme B$^+$ killer Tfh cells in RT disease, and granzyme B$^+$ killer Tfh cells are a distinctive pathological feature of RT disease.

Example 7

Figure 13:
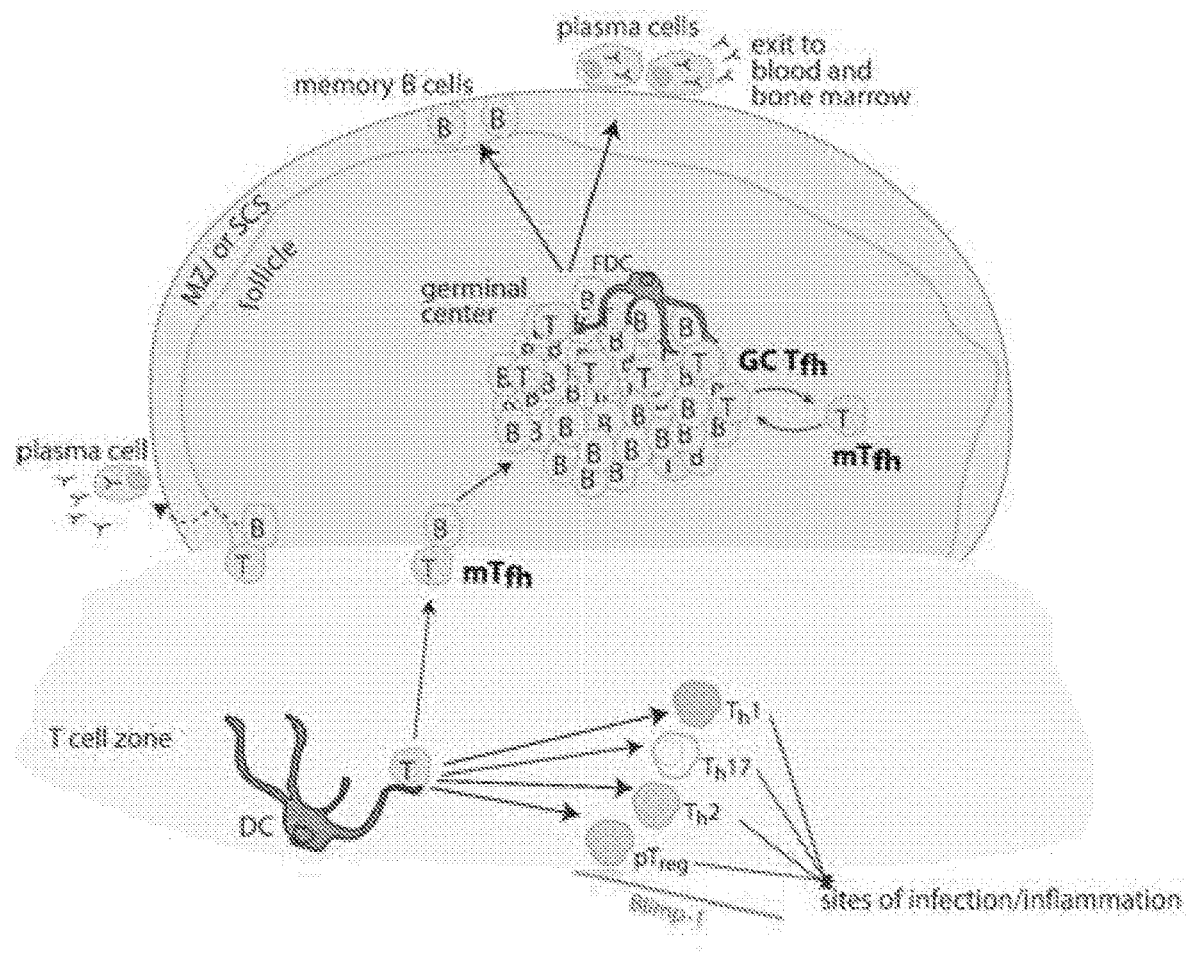
FIG. 13 shows a non-limiting illustration of a germinal center biology model, where DCs prime $CD4^+$T cells and induce differentiation. $CD4^+$T cells that become killer Tfh cells from cognate interaction with B cells at the T:B border. Tfh further differentiate into Granzyme B+GC killer Tfh, which instruct GC B cells to proliferate, mutate, and differentiate into memory B cells and plasma cells.

This example relates to FIG. 13.

Germinal centers contain T follicular helper (Tfh) cells, specialized CD4$^+$ T cells whose function is to aid GC B cells (FIG. 13). After the discovery of the Tfh master transcriptional regulator Bcl6, much work has been undertaken to understand Tfh cells. Tfh cells are critical for germinal centers. The help they provide to B cells is critical to the ability of germinal centers to generate and select for B cells with the highest affinity for pathogen-specific antigens. A Tfh cell can migrate in a B cell follicle between the mantle and germinal center (FIG. 13). Tfh cells in the mantle zone are denoted as mantle Tfh (mTfh) cell. A Tfh cell in a germinal center is a GC Tfh cell. Antigen-experienced (CD45RA$^-$) CD4$^+$ T cells can thus be divided into non-Tfh (CXCR5$^-$ effector cells), mantle Tfh (CXCR5$^{int}$PD-1$^{int}$), and GC Tfh (CXCR5$^{hi}$PD-1$^{hi}$) cells (FIG. 13). In germinal centers, B cells circulate through two regions: the light zone and the dark zone. In the light zone, GC B cells bind to antigen and present peptide in Class II complexes to Tfh cells (FIG. 13). The GC Tfh cells, in turn, provide help signals essential for survival, mutation, and proliferation to GC B cells. GC B cells that successfully compete for help from GC Tfh cells are then directed to the dark zone, where they undergo proliferation and somatic hypermutation. These mutated GC B cells cycle back to the light zone, where B cells with the highest affinity B cell receptors are selected by Tfh cells for another round of proliferation and mutation. Tfh cells are crucial components of the germinal center response, as antigen-specific GC Tfh cells help the GC B cells to generate memory B cells and high affinity antibodies (FIG. 13).

Example 8

Figure 14:
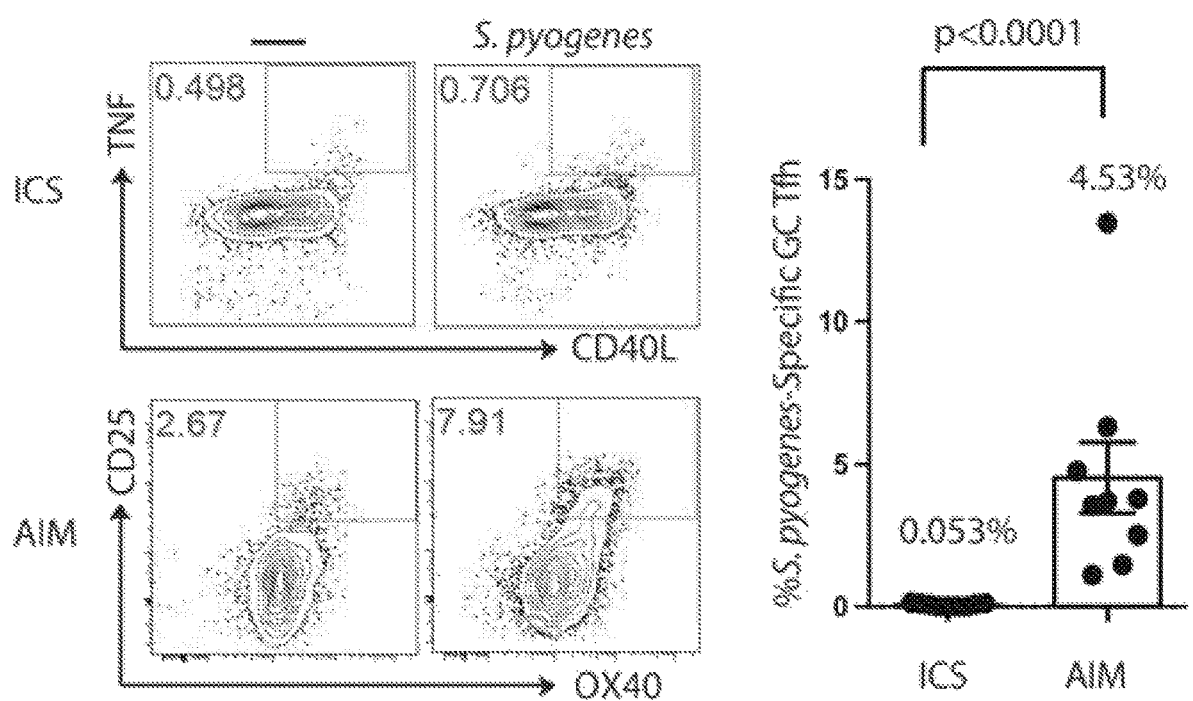
FIG. 14 shows a non-limiting example of Activation Induced Marker Assay (AIM), where 85-fold more *S. pyogenes*-specific Granzyme B+GC killer Tfh cells than traditional Intracellular cytokine staining (ICS) are identified. Dan et al., Journal of Immunology, 2016. P-value determined by Wilcoxon rank test.

This example relates to FIG. 14.

To understand S. pyogenes-specific CD4+ T cells, it is necessary to be able to quantify and phenotype S. pyogenes-specific CD4+ T cells. The inventors developed novel methodology to assess antigen specific GC Tfh cells. This methodology relies on the upregulation of activation markers CD25, OX40 and PD-L1 instead of traditional intracellular cytokine staining (ICS). GC Tfh cells communicate with nearby B cells and thus only need to produce infinitesimal quantities of cytokines. The activation induced marker (AIM) assay has allowed the inventors to reveal that traditional ICS only detects ~1% of S. pyogenes-specific GC Tfh cells (FIG. 14). AIM is also more sensitive than ICS for detecting antigenic-specific GC Tfh cells for other pathogens or vaccines Phenotypic and histologic analyses revealed significantly more GC Tfh and GC B cells with larger germinal center areas in non-RT tonsils compared to RT tonsils. This demonstrates that either (1) RT tonsils have a reduced capacity to mount an S. pyogenes immune response or that (2) S. pyogenes affects RT tonsils differently than non-RT tonsils resulting in these phenotypic and histologic observations. To address this, the inventors developed the activation induced marker (AIM) assay to quantify antigen-specific GC Tfh cells (FIG. 14). One would anticipate that RT tonsils should have more S. pyogenes-specific GC Tfh cells, as they have had more S. pyogenes infections. Instead, the inventors observed no difference in the frequency of S. pyogenes-specific GC Tfh cells between RT and non-RT patients (FIG. 8B). However, importantly, the inventors observed a significant skew in the proportion of S. pyogenes-specific GC Tfh cells among S. pyogenes-specific CD4+ T cells (p=0.025, FIG. 3D). Without being limited to any particular theory, this may indicate that RT tonsils have a defect in their S. pyogenes-specific GC Tfh cell response.

Example 9

Figure 15:
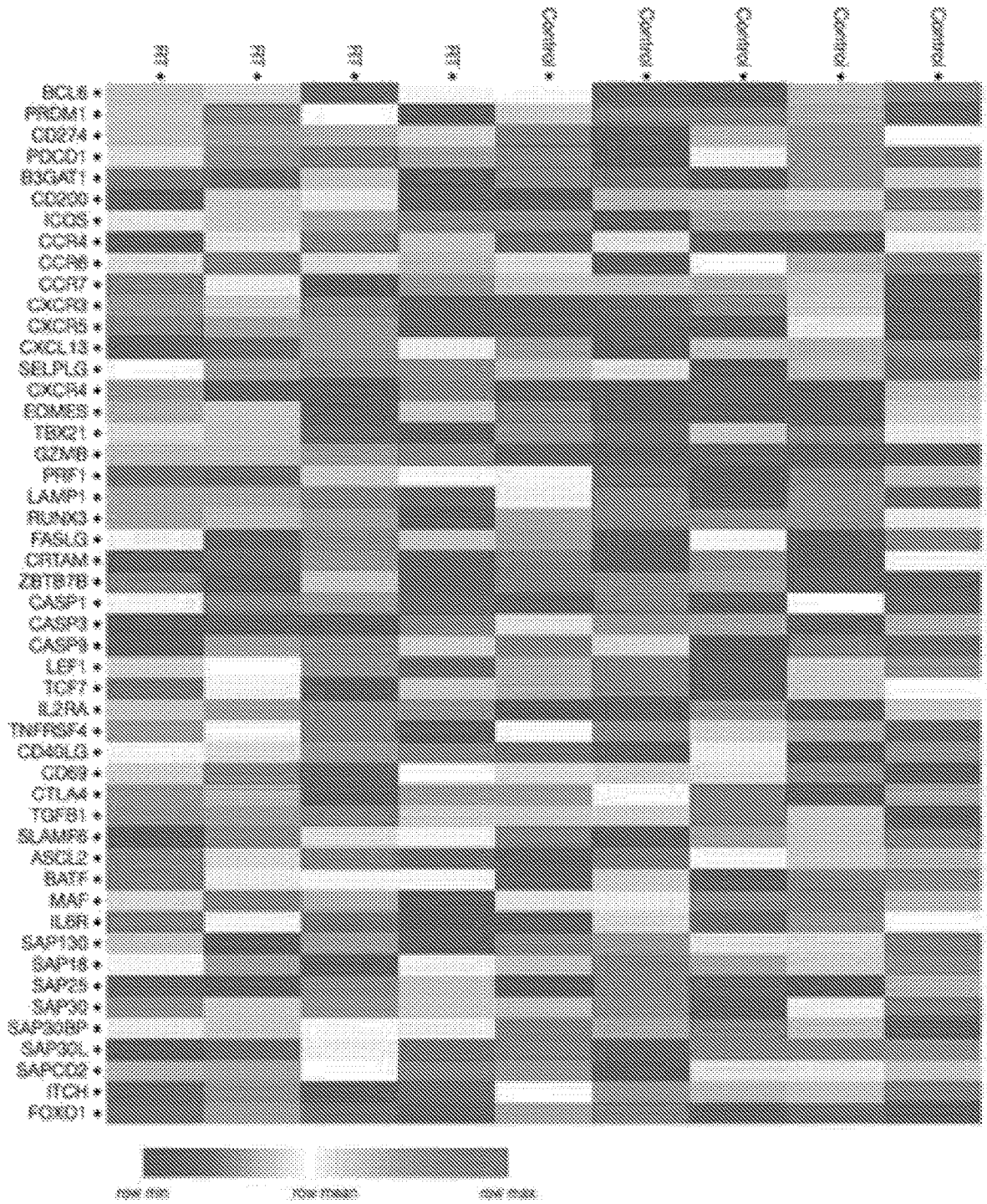
FIG. 15 shows a non-limiting example of an RNA-sequencing heat map and volcano plot of SpeA-responsive Granzyme B+GC killer Tfh cells from RT and non-RT tonsils. Heat map of Tfh associated genes (top). Volcano plot of all genes demonstrates that RT tonsils have significantly more GZMB expression than non-RT tonsils.

This example relates to FIG. 15.

The streptococcal pyrogenic exotoxin A (SpeA) superantigen has provided S. pyogenes with an evolutionary advantage. Acquisition of the prophage-encoded SpeA allowed for the global persistence and dominance of the M1 serotype as the etiologic agent of strep throat. Since AIM is a live cell assay, the inventors were able to FACS sort S. pyogenes-specific GC Tfh cells and SpeA-responsive GC Tfh cells. RNA-sequencing of SpeA-responsive GC Tfh cells revealed that GZMB was the #1 most significantly upregulated gene in RT tonsils compared to non-RT tonsils (p=0.016, FIG. 15). This was a striking difference compared to all other gene expression changes. This demonstrates that SpeA affects RT tonsils differently than non-RT tonsils. Without being limited to a particular theory, granzyme B expression may explain how S. pyogenes modulates the adaptive immune response in RT tonsils. Thus, aberrant granzyme B expression by GC Tfh cells in RT tonsils may result in reprogramming of the GC Tfh cell from one that helps GC B cells to one that kills.

Cytotoxic CD4+T cells (not Tfh) have been described as a distinct type of effector CD4+T cell in human diseases, including dengue, parvovirus, CMV, and HIV infections. These human CD4+cytotoxic lymphocytes (CTL) are known to express cytotoxicity effector proteins, including granzyme B+, and be able to kill target cells, but are completely unrelated to Tfh cells. Murine models have suggested potential transcriptional regulators of CD4+CTL differentiation including Tbet (the Th1 master transcription regulator), Eomes, and Runx proteins. All of those are transcription factors active in CD8+CTLs. Thus, granzyme B+GC Tfh cells in RT tonsils likely represent an extreme immune response in children with recurrent S. pyogenes tonsillitis, potentially actively directed by S. pyogenes SpeA immunomodulation, with the resulting consequence being an impaired immune response with smaller germinal centers and significantly fewer GC Tfh and GC B cells. Granzyme B+GC Tfh cells are a surprising finding, as these GC Tfh cells might no longer provide help to GC B cells (FIG. 13), but instead kill them.

Example 10

Figure 16A:
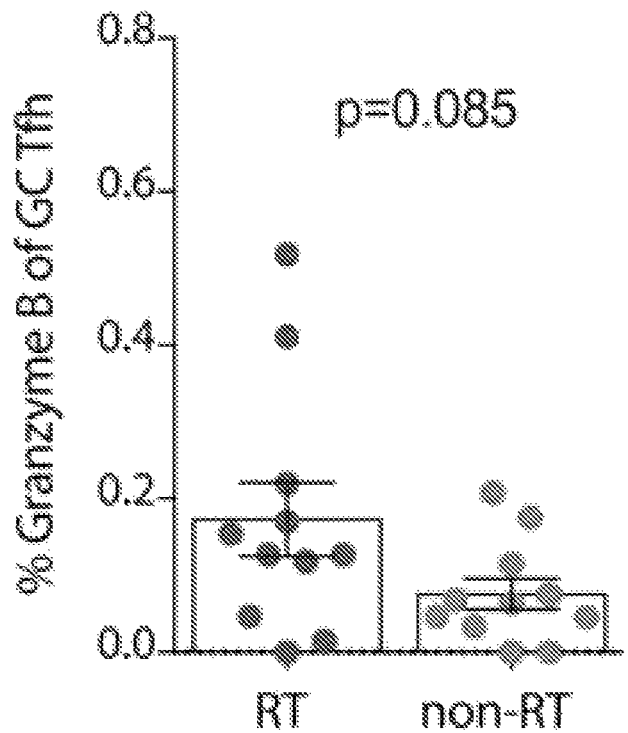
FIGS. 16A and 16B show a non-limiting example of Granzyme B+GC killer Tfh cells in RT and non-RT tonsils.
Figure 16B:
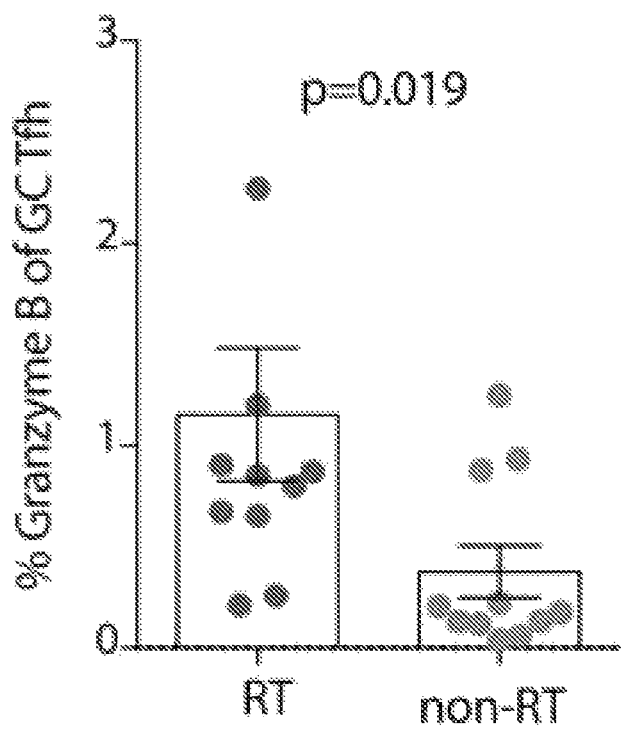

This example relates to FIGS. 16A and 16B.

RNA sequencing of SpeA responsive GC Tfh cells from RT tonsils demonstrate higher granzyme B RNA expression than non-RT tonsils. The inventors verified capacity for granzyme B protein expression by GC Tfh cells following stimulation with SpeA by flow cytometry (FIGS. 16A-16B) and ImageStream technology, which combines flow cytometry with microscopy, allowing visualization of granzyme B containing vesicles within GC Tfh cells expressing CD4, CXCR5 and PD-1 (FIG. 6F).

To determine whether granzyme B+GC Tfh cells are preferentially associated with RT and its associated germinal center pathology, the inventors assessed granzyme B+GC Tfh cells in two contexts: (i) RT versus non-RT tonsils and (ii) RT tonsil versus lymph nodes and spleen. (i) As RT tonsils have significantly fewer GC Tfh and GC B cells (FIGS. 1A to 1J) and smaller germinal centers (FIG. 1I), RT tonsils have more granzyme B+GC Tfh cells than non-RT tonsils. Repeated infections in RT tonsils are akin to a chronic infectious state, in which cytotoxic CD4+ T cells have been described. Using multiparameter flow cytometry, the inventors observed more granzyme B+GC Tfh cells in RT tonsils than non-RT tonsils directly ex vivo (p=0.085, FIG. 16A). After SpeA stimulation, the inventors observed a significant increase in granzyme B+GC Tfh cells in RT tonsils compared to non-RT tonsils (p=0.019, FIG. 16B). Additional RT and non-RT donors were tested for granzyme B protein expression both directly ex vivo and after stimulation.

Example 11

Figure 17:
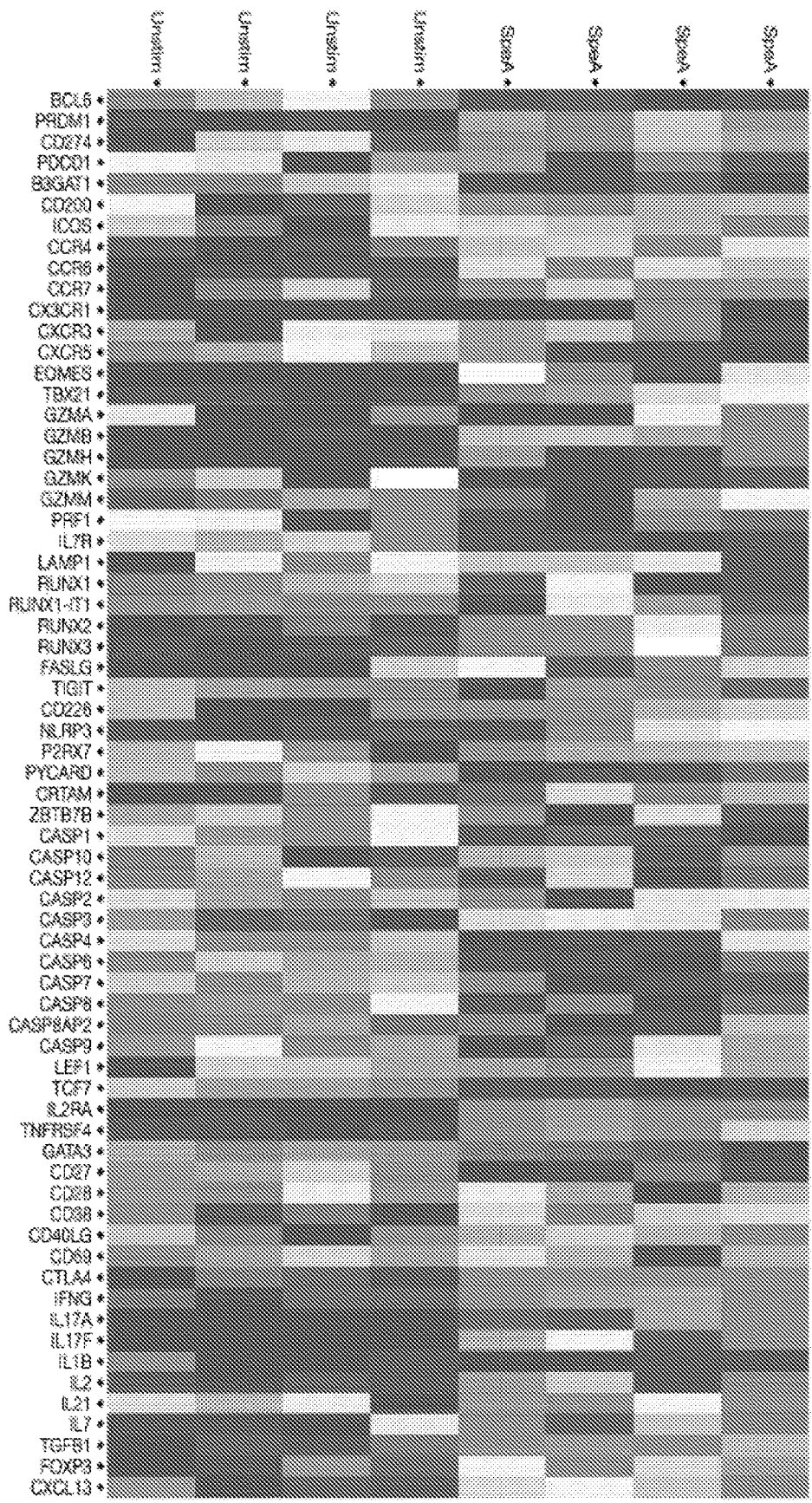
FIG. 17 shows a non-limiting example of an RNA-sequencing heat map of unstimulated and SpeA-responsive Granzyme B+GC killer Tfh cells from RT tonsils. Heat map of Tfh associated genes and potential upstream and downstream regulators of granzyme B expression. Data from 4 independent samples.

This example relates to FIG. 17.

Comparison of the RNA-sequencing profile of unstimulated GC Tfh cells (CD25-OX40-) with SpeA responsive GC Tfh cells (CD25+OX40+) reveals (1) increased PRDM1 (BLIMP1), (2) decreased BCL6, (3) increased ICOS, (4) increased GZMB, (5) decreased CD28 and increased CTLA4, and (6) increased EOMES and TBX21 (T-bet) (FIG. 17). In certain embodiments, these are transcription factors which re-program a GC Tfh cell.

From murine CD8+ T cells studies, transcription factors Blimp1, Eomes, T-bet, and the Runx proteins can induce granzyme B expression. The inventors have shown that Bcl6 and Blimp-1 are reciprocally antagonistic transcription factors. Blimp1 represses Bcl6, the Tfh lineage defining transcription factor, and Bcl6 repressed PRDM1. Tfh and Th1 are known to be distinct and antagonistic differentiation pathways, with T-bet and Blimp1 being central regulators of Th1 cells. Repression of BCL6 by BLIMP1 can allow for transcription of TBX21 and RUNX genes, both of which have BCL6 bound loci. In human GC Tfh cells, BCL6 antagonizes T-BET, the Th1 transcriptional factor encoded by TBX21. BCL6 can also inhibit RUNX proteins. Without being limited to any particular theory, cytolytic activity in GC Tfh cells may occur through inappropriate expression of T-BET, EOMES, or RUNX1, RUNX2, or RUNX3 due to impaired BCL6 expression or other mechanisms.

Example 12

Figure 18:
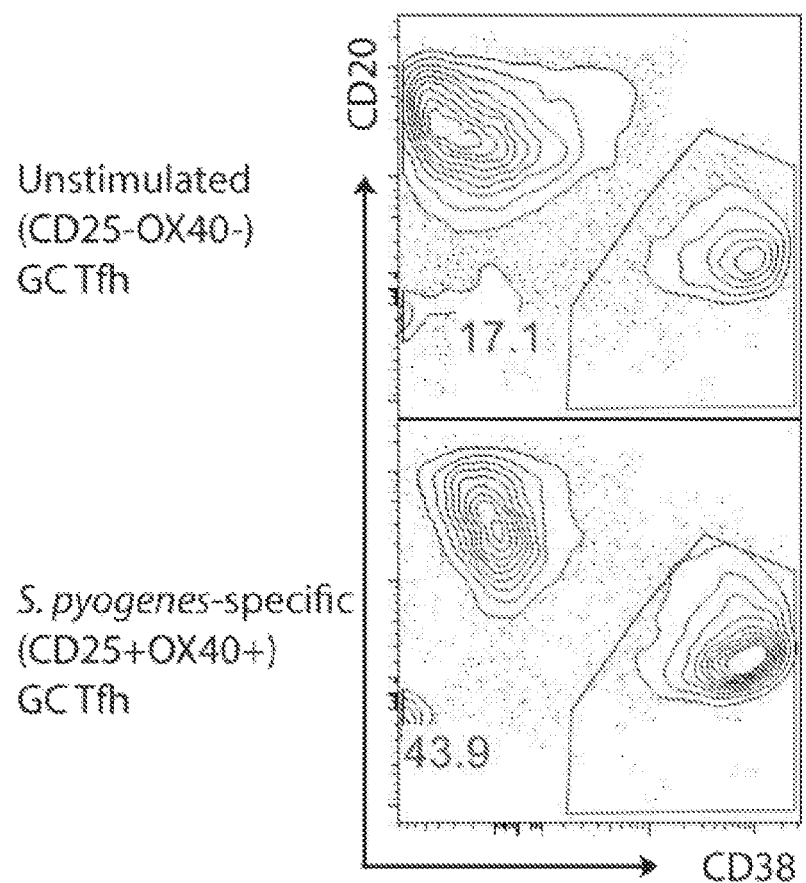
FIG. 18 shows a non-limiting example of T:B co-culture using *S. pyogenes*-specific Granzyme B+GC killer Tfh cells and autologous memory B cells. Tonsillar cells were stimulated with 10 ug/mL heat-inactivated, antibiotic-killed *S. pyogenes*. AIM+Granzyme B+GC killer Tfh cells were FACS sorted. As a control, CD25−OX40−unstimulated Granzyme B+GC killer Tfh cells were FACS sorted. Granzyme B+GC killer Tfh (30,000) were co-cultured with autologous memory B cells (CD27+IgD−-CD20+) at a 1:1 ratio for 7 days in media containing FBS and 100 ng/mL SEB to bring GC killer Tfh cells in close proximity to B cells. FACS plots show % plasmablasts.
Figure 19:
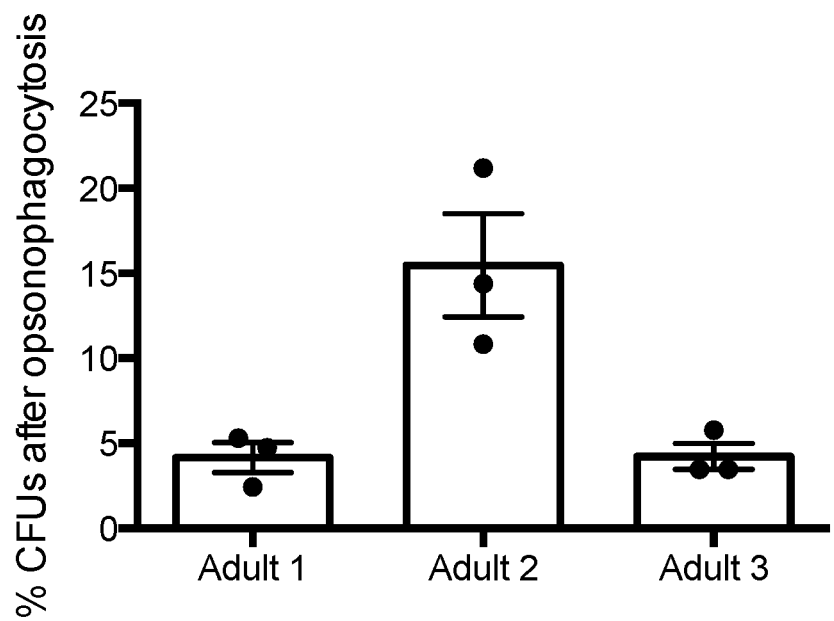
FIG. 19 shows a non-limiting example of a *S. pyogenes* Killing Assay. *S. pyogenes* is incubated in plasma for 30 minutes, treated with neutrophils for 30 minutes, and then plated out to determine % *S. pyogenes* killing, following normalization of growth to opsonized *S. pyogenes* without neutrophil mediated killing. Growth is reported as colony forming units (CFUs).
Figure 20:
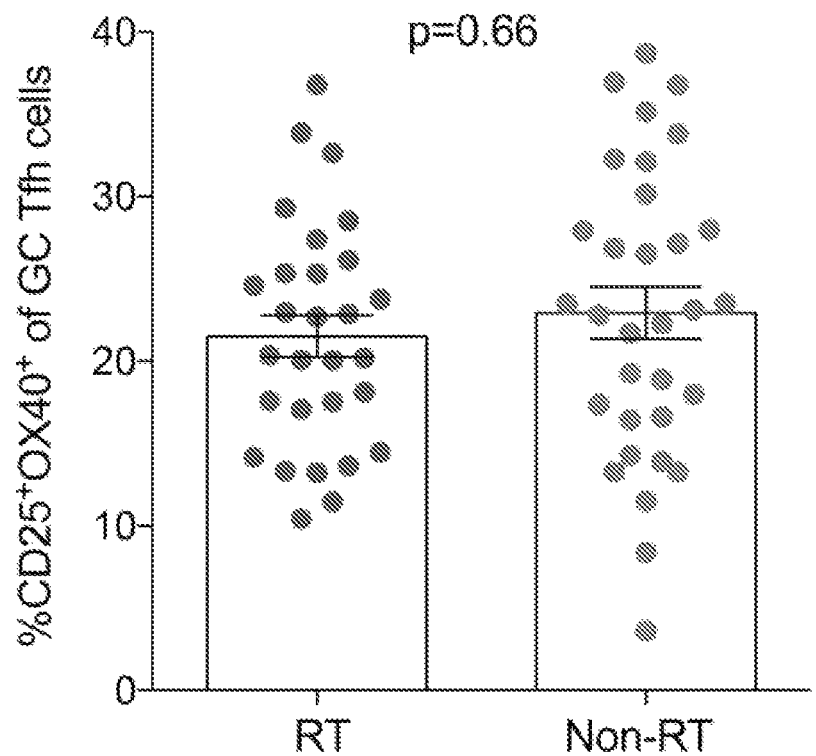
FIG. 20 shows a non-limiting example of RT and Non-RT tonsils not being "exhausted". Tonsil cells were cultured for 18 hours with 1 ug/mL SEB. RT=29, non-RT=32. There was no difference in SEB-responsive Granzyme B+GC killer Tfh cells. P-value determined by Wilcoxon rank test.

This example relates to FIGS. 18, 19 and 20.

As providing help to B cells is the primary function of Tfh cells, it is tested whether DQB1*06:02 is associated with an improved quality of GC Tfh help to GC B cells, using T:B co-culture assays. To determine if the GC Tfh cells from DQB1*06:02+ non-RT tonsils have improved ability to instruct autologous B cells to proliferate and produce immunoglobulin, previously developed techniques were used. Specifically, following 18 hours of tonsillar T cell culture with S. pyogenes (heat inactivated, antibiotic killed, unless specified otherwise), the cells are sorted for AIM+ S. pyogenes-specific GC Tfh and T:B co-cultures are set up using autologous memory B cells (FIG. 18). GC Tfh help is measured by (1) absolute plasmablast production; (2) total IgG, IgM, and IgA production; and (3) S. pyogenes-specific IgG, IgM, and IgA production after 7 days of culture. 10 DQB1*06:02+ non-RT tonsils are compared to 10 non-RT tonsils expressing other DQB1 alleles. Additionally, the functionality of the anti-S. pyogenes antibody in the culture supernatant and produced by B cells is tested in an opsonization dependent killing assay (FIG. 19). Of note, CD4+ T cells from RT tonsils are not exhausted as comparable levels of SEB-responsive GC Tfh cells are observed in both groups (FIG. 20).

Example 13

Figure 21:
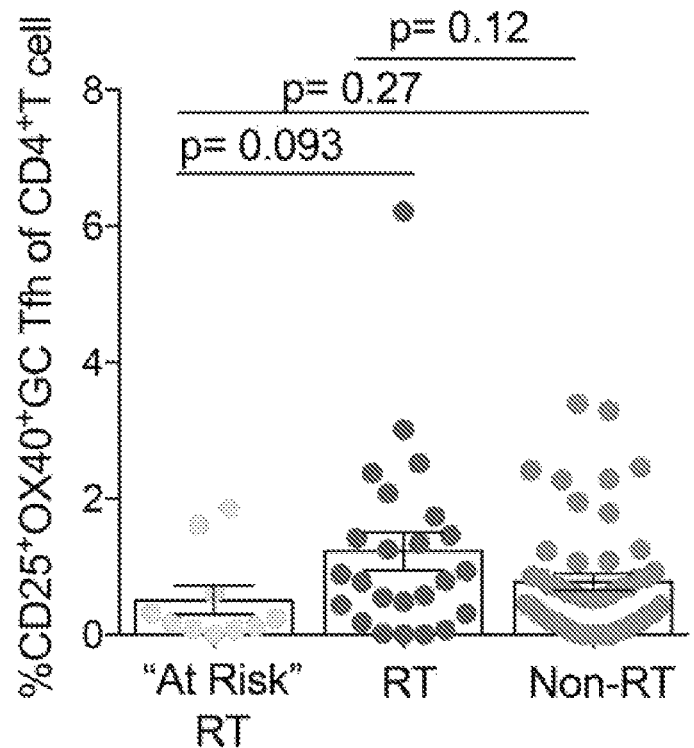
FIG. 21 shows a non-limiting example of there being fewer *S. pyogenes*-specific CD4+T cells from RT children with "At Risk" alleles compared to RT children and non-RT children. Tonsil cells were cultured for 18 hours with 10 ug/mL *S. pyogenes*. AIM (CD25+OX40+) Granzyme B+GC killer Tfh cells were quantified. RT=24, "At Risk" RT=10, non-RT=50. P-value determined by Wilcoxon rank test.
Figure 22:
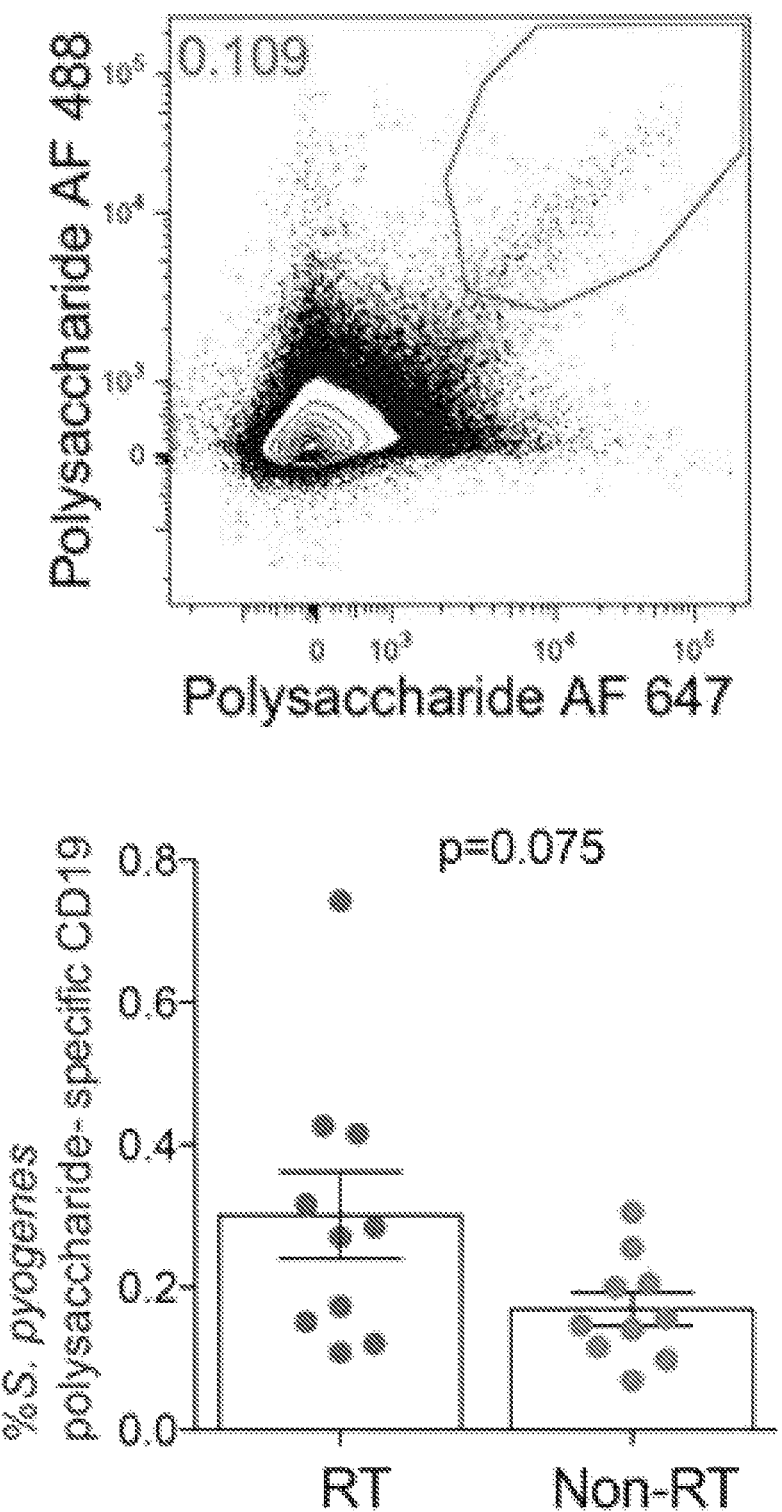
FIG. 22 shows a non-limiting example of detection of *S. pyogenes* Polysaccharide-specific tonsillar B cells. Tonsils cells were incubated with *S. pyogenes* polysaccharide labeled with Alexa Fluor 488 and Alexa Fluor 647. Double positive CD19+ B cells were identified as *S. pyogenes* polysaccharide specific. *S. pyogenes* polysaccharide specific B cells were detected at a higher frequency in RT tonsils than non-RT tonsils. RT=10, non-RT=10. P-value determined by Wilcoxon rank test.

This example relates to FIGS. 21 and 22.

To determine if HLA DRB1*01:01 and DRB1*07:01 are risk alleles for recurrent tonsillitis, the frequency of these risk alleles was evaluated by two different methods, one looking specifically at patients with weak germinal center responses, and the other examining all RT patients.

To demonstrate that the RT individuals with the lowest GC responses (lowest GC Tfh and GC B cells) have a higher frequency of "GC-response At Risk" alleles HLA DRB1*01:01 and/or HLA DRB1*07:01, 138 pediatric patients were recruited with an approximate equal distribution of RT and non-RT patients. The GC Tfh and GC B cells in the RT group were rank ordered and the allelic frequencies of the lowest quartile of RT patients were compared with the lowest GC Tfh and GC B cell frequencies to non-RT children. The association between DRB1*01:01 as a risk allele for recurrent tonsillitis in the overall RT group in comparison to the general population (GP) was similarly tested.

RT patients have significantly fewer GC Tfh cells (FIG. 1), suggesting that these children have an immune deficit in making a S. pyogenes-specific GC Tfh response. The inventors have observed a decreased ratio of S. pyogenes-specific GC Tfh cells to overall S. pyogenes-specific CD4+ T cells (FIG. 2). Fewer S. pyogenes-specific GC Tfh cells will result in reduced instruction to GC B cells, and thus reduced memory and plasmablast differentiation and reduced production of S. pyogenes-specific antibodies. Using the AIM assay and whole S. pyogenes lysate, the inventors have quantified S. pyogenes-specific GC Tfh cells among RT tonsils with the risk alleles, RT tonsils without risk alleles, and non-RT tonsils. RT tonsils from donors with risk alleles have reduced S. pyogenes-specific GC Tfh cells compared to RT tonsils with other DRB1 alleles, p=0.093, FIG. 21). This demonstrates that harboring a risk allele impacts the S. pyogenes-specific immune response. This is consistent with DRB1*01:01 and DRB1*07:01 being specifically associated with poor T cell responses to S. pyogenes. As a comparison, the inventors observed more *S. pyogenes*-specific GC Tfh cells in RT tonsils without risk alleles compared to non-RT tonsils (FIG. 21). The difference between tonsils with and without risk alleles demonstrates that DRB1*01:01 and DRB1*07:01 impact *S. pyogenes*-specific GC Tfh responses.

To determine whether RT individuals with HLA DRB1*01:01 and HLA DRB1*07:01 have reduced *S. pyogenes*-specific germinal center CD4+ T cell responses, *S. pyogenes*-specific GC Tfh cells from individuals with risk alleles were quantified and compared to the *S. pyogenes*-specific GC Tfh cells from RT individuals with other DR alleles. *S. pyogenes*-specific GC Tfh cells from non-RT tonsils bearing the DRB1*01:01 or DRB1*07:01 risk alleles were also quantified.

The TCR Vβ repertoire of all GC Tfh cells in RT tonsils from donors with DRB1*01:01 or DRB1*07:01 alleles and RT tonsils with other DRB1 alleles were assessed to examine whether GC Tfh cells from donors negative for risk alleles have more diverse *S. pyogenes*-specific TCR Vβ clonotypic repertoires than GC Tfh cells from donors with risk alleles. This is suggested by the reduced *S. pyogenes*-specific GC Tfh cell frequencies in RT donors with risk alleles (FIG. 21).

*S. pyogenes*-specific GC Tfh cell to autologous B cells were quantified in a T:B co-culture assay for RT children with risk alleles compared against RT children without risk alleles (10 donors per group).

Given the difference in *S. pyogenes* GC Tfh cell frequency between RT tonsils with and without risk alleles, expression of BCL6, the master transcription factor regulator of GC Tfh cells was evaluated. BLIMP1 antagonizes BCL6. Therefore, in certain cases, and without being limited to any particular theory, RT patients with risk alleles may have reduced GC Tfh cells due to reduced induction of BCL6, or overexpression of the inhibitor BLIMP1. This can be determined by quantitative PCR for BCL6 and PRDM1 (which encode BLIMP1) using GC Tfh cell RNA from RT patients with and without risk alleles.

Example 14

This example relates to FIGS. 21 and 22.

Rheumatic heart disease (RHD) is the most common lethal cause of acquired heart disease among children with an estimated 233,000 deaths/year worldwide. RHD is considered a downstream sequellae of *S. pyogenes* tonsillophrayngitis infection. Given the RT HLA associations are alleles also associated with RHD, it is interrogated whether the genetic immunosusceptibility of these children to recurrent tonsillitis is paired to the development of cardiac cross-reactive CD4+ T cells and antibodies. As such, these potentially cross-reactive immune responses likely first develop in the tonsils. Molecular mimicry to *S. pyogenes* M protein and *S. pyogenes* polysaccharide has been implicated in RHD. Evidence for this includes: (1) the isolation of cross-reactive CD4+ T cells from cardiac tissue of RHD patients, (2) higher titers of circulating IgG against *S. pyogenes* polysaccharide, cardiac myosin, and collagen, (3) ability of the dominant *S. pyogenes* polysaccharide epitope to induce T cell dependent response against cardiac myosin in mice, and (4) repeated exposure to *S. pyogenes* M protein induces cardiac damage in a rat model.

To determine if the development of cross-reactive M1-specific CD4+ T cells is associated with RT patients possessing DRB1*01:01 or DRB1*07:01 risk alleles, M1-specific GC Tfh cells were quantified. Using recombinant M1 protein, quantify M1-protein specific GC Tfh cells were quantified from RT donors with and without risk alleles and non-RT donors using the high sensitivity AIM assay. In certain instances, RT tonsils from donors with DRB1*01:01 or DRB1*07:01 risk alleles had a higher frequency of M1-specific GC Tfh cells amidst all *S. pyogenes*-specific GC Tfh cells (FIG. 21) compared to RT tonsils without DRB1*01:01 and DRB1*07:01 and non-RT tonsils.

As a by-product of *S. pyogenes* infection, children may develop autoreactive CD4+ T cells, including autoreactive GC Tfh cells. Without being limited to any particular theory, such autoreactive GC Tfh cells may be more adept at instructing B cells to generate antibodies which bind to cardiac myosin and cause the development of RHD. Given the association between RT risk alleles and the development of RHD, it was assessed whether RT patients with risk alleles generate autoreactive CD4+ T cells. A prolonged culture was needed for sensitivity. Total tonsil cells from 10 risk allele RT donors were stimulated with M1 protein for 14 days to allow for expansion of M1-specific CD4+ T cells. After 14 days, restimulation with either M1 protein or cardiac proteins such as cardiac myosin was done to evaluate for autoreactive CD4+ T cells by TNF ELISPOT (among cytokines, TNF is one of the most commonly expressed by GC Tfh that can be detected by ELISPOT). As a control experiment, total tonsil cells were stimulated with tetanus antigen for 14 days, followed by restimulation with either tetanus antigen or cardiac myosin. In the control experiment, it was expected that there would be TNF production only with tetanus restimulation and not with cardiac myosin.

It was evaluated whether RT children possessing HLA risk alleles have circulating anti-cardiac myosin antibodies. Plasma from 10 RT children with HLA risk alleles was compared to 10 RT children without risk alleles, 10 non-RT children, and 10 healthy adults from the GP. As an alternative, another potentially cross-reactive component of *S. pyogenes* was its polysaccharide, specifically the N-acetyl glucosamine component, which has been implicated in RHD. Analysis of *S. pyogenes*-specific B cells indicated that RT tonsils may have a higher frequency of *S. pyogenes*-specific B cells than non-RT tonsils (FIG. 22), likely resulting from more recent *S. pyogenes* infection in RT children. However, it may also reflect an autoreactive potential in these B cells, as these RT children with a higher frequency of *S. pyogenes*-specific B cells were unable to prevent recurrent infections (FIGS. 1A to 1J). Whether *S. pyogenes*-specific B cells from RT children with these HLA risk alleles produce autoreactive antibodies with cardiac proteins is assessed using memory B cell cultures.

Other examples of implementations will become apparent to the reader in view of the teachings of the present description and as such, will not be further described here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

With respect to ranges of values, the invention encompasses the upper and lower limits and each intervening value between the upper and lower limits of the range to at least a tenth of the upper and lower limit's unit, unless the context clearly indicates otherwise. Further, the invention encompasses any other stated intervening values.

Although various embodiments of the disclosure have been described and illustrated, it will be apparent to those skilled in the art in light of the present description that numerous modifications and variations can be made. The scope of the invention is defined more particularly in the appended claims.

REFERENCES

References Cited in Background and Examples 1-6

1. Ebell M H, Smith M A, Barry H C, Ives K, Carey M. The rational clinical examination. Does this patient have strep throat? JAMA. 2000 Dec. 13; 284(22):2912-2918. PMID: 11147989
2. Ferretti J J, McShan W M, Ajdic D, Savic D J, Savic G, Lyon K, Primeaux C, Sezate S, Suvorov A N, Kenton S, Lai H S, Lin S P, Qian Y, Jia H G, Najar F Z, Ren Q, Zhu H, Song L, White J, Yuan X, Clifton S W, Roe B A, McLaughlin R. Complete genome sequence of an M1 strain of *Streptococcus pyogenes*. Proceedings of the National Academy of Sciences. 2001 Apr. 10; 98(8):4658-4663. PMCID: PMC31890
3. Johnston R J, Poholek A C, DiToro D, Yusuf I, Eto D, Barnett B, Dent A L, Craft J, Crotty S. Bcl6 and Blimp-1 are reciprocal and antagonistic regulators of T follicular helper cell differentiation. Science. American Association for the Advancement of Science; 2009 Aug. 21; 325 (5943):1006-1010. PMCID: PMC2766560
4. Yu D, Rao S, Tsai L M, Lee S K, He Y, Sutcliffe E L, Srivastava M, Linterman M, Zheng L, Simpson N, Ellyard J I, Parish I A, Ma C S, Li Q-J, Parish C R, Mackay C R, Vinuesa C G. The transcriptional repressor Bcl-6 directs T follicular helper cell lineage commitment. Immunity. 2009 Sep. 18; 31(3):457-468. PMID: 19631565
5. Nurieva R I, Chung Y, Martinez G J, Yang X O, Tanaka S, Matskevitch T D, Wang Y-H, Dong C. Bcl6 mediates the development of T follicular helper cells. Science. 2009 Aug. 21; 325(5943):1001-1005. PMCID: PMC2857334
6. Victora G D, Dominguez-Sola D, Holmes A B, Deroubaix S, Dalla-Favera R, Nussenzweig M C. Identification of human germinal center light and dark zone cells and their relationship to human B-cell lymphomas. Blood. American Society of Hematology; 2012 Sep. 13; 120(11):2240-2248. PMCID: PMC3447782
7. Crotty S. T follicular helper cell differentiation, function, and roles in disease. Immunity. Elsevier Inc; 2014 Oct. 16; 41(4):529-542. PMCID: PMC4223692
8. Gitlin A D, Shulman Z, Nussenzweig M C. Clonal selection in the germinal centre by regulated proliferation and hypermutation. Nature. Nature Research; 2014 May 29; 509(7502):637-640. PMCID:PMC4271732
9. Dan J M, Lindestam Arlehamn C S, Weiskopf D, da Silva Antunes R, Havenar-Daughton C, Reiss S M, Brigger M, Bothwell M, Sette A, Crotty S. A Cytokine-Independent Approach To Identify Antigen-Specific Human Germinal Center T Follicular Helper Cells and Rare Antigen-Specific CD4+ T Cells in Blood. J Immunol. American Association of Immunologists; 2016 Aug. 1; 197(3):983-993. PMCID: PMC4955771
10. Havenar-Daughton C, Reiss S M, Carnathan D G, Wu J E, Kendric K, Torrents de la Peña A, Kasturi S P, Dan J M, Bothwell M, Sanders R W, Pulendran B, Silvestri G, Crotty S. Cytokine Independent Detection of Antigen-Specific Germinal Center T Follicular Helper Cells in Immunized Nonhuman Primates Using a Live Cell Activation-Induced Marker Technique. J Immunol. American Association of Immunologists; 2016 Aug. 1; 197(3):994-1002. PMCID: PMC4955744
11. Crotty S. Follicular Helper CD4 T Cells (T FH). Annu Rev Immunol. 2011 Apr. 23; 29(1):621-663.
12. Locci M, Havenar-Daughton C, Landais E, Wu J, Kroenke M A, Arlehamn C L, Su L F, Cubas R, Davis M M, Sette A, Haddad E K, International AIDS Vaccine Initiative Protocol C Principal Investigators, Poignard P, Crotty S. Human circulating PD-1+CXCR3−CXCR5+ memory Tfh cells are highly functional and correlate with broadly neutralizing HIV antibody responses. Immunity. Elsevier Inc; 2013 Oct. 17; 39(4):758-769. PMCID: PMC3996844
13. Benhnia M R-E-I, McCausland M M, Laudenslager J, Granger S W, Rickert S, Koriazova L, Tahara T, Kubo R T, Kato S, Crotty S. Heavily isotype-dependent protective activities of human antibodies against vaccinia virus extracellular virion antigen B5. J Virol. 2009 December; 83(23):12355-12367. PMCID: PMC2786738
14. Crotty S, Felgner P, Davies H, Glidewell J, Villarreal L, Ahmed R. Cutting edge: long-term B cell memory in humans after smallpox vaccination. The Journal of Immunology. 2003 Nov. 15; 171(10):4969-4973. PMID: 14607890
15. Moyron-Quiroz J E, McCausland M M, Kageyama R, Sette A, Crotty S. The smallpox vaccine induces an early neutralizing IgM response. Vaccine. 2009 Dec. 10; 28(1): 140-147. PMCID: PMC2788018
16. Havenar-Daughton C, Lindqvist M, Heit A, Wu J E, Reiss S M, Kendric K, Blanger S, Kasturi S P, Landais E, Akondy R S, McGuire H M, Bothwell M, Vagefi P A, Scully E, IAVI Protocol C Principal Investigators, Tomaras G D, Davis M M, Poignard P, Ahmed R, Walker B D, Pulendran B, McElrath M J, Kaufmann D E, Crotty S. CXCL13 is a plasma biomarker of germinal center activity. Proc Natl Acad Sci USA. National Acad Sciences; 2016 Mar. 8; 113(10):2702-2707. PMCID: PMC4790995
17. Hong J J, Amancha P K, Rogers K A, Courtney C L, Havenar-Daughton C, Crotty S, Ansari A A, Villinger F. Early lymphoid responses and germinal center formation correlate with lower viral load set points and better prognosis of simian immunodeficiency virus infection. J 18. Boettler T, Choi Y S, Salek-Ardakani S, Cheng Y, Moeckel F, Croft M, Crotty S, Herrath von M. Exogenous OX40 stimulation during lymphocytic choriomeningitis virus infection impairs follicular Th cell differentiation and diverts CD4 T cells into the effector lineage by upregulating Blimp-1. J Immunol. American Association of Immunologists; 2013 Nov. 15; 191(10):5026-5035. PMCID: PMC3915873
19. Landais E, Huang X, Havenar-Daughton C, Murrell B, Price M A, Wickramasinghe L, Ramos A, Bian C B, Simek M, Allen S, Karita E, Kilembe W, Lakhi S, Inambao M, Kamali A, Sanders E J, Anzala O, Edward V, Bekker L-G, Tang J, Gilmour J, Kosakovsky-Pond S L, Phung P, Wrin T, Crotty S, Godzik A, Poignard P. Broadly Neutralizing Antibody Responses in a Large Longitudinal Sub-Saharan HIV Primary Infection Cohort. Trkola A, editor. PLoS Pathogens. Public Library of Science; 2016 January; 12(1):e1005369. PMCID: PMC4713061
20. Havenar-Daughton C, Carnathan D G, Torrents de la Peña A, Pauthner M, Briney B, Reiss S M, Wood J S, Kaushik K, van Gils M J, Rosales S L, van der Woude P, Locci M, Le K M, de Taeye S W, Sok D, Mohammed A U R, Huang J, Gumber S, Garcia A, Kasturi S P, Pulendran B, Moore J P, Ahmed R, Seumois G, Burton D R, Sanders R W, Silvestri G, Crotty S. Direct Probing of Germinal Center Responses Reveals Immunological Features and Bottlenecks for Neutralizing Antibody Responses to HIV Env Trimer. Cell Rep. 2016 Nov. 22; 17(9):2195-2209. PMCID: PMC5142765
21. Martinez G J, Hu J K, Pereira R M, Crampton J S, Togher S, Bild N, Crotty S, Rao A. Cutting Edge: NFAT Transcription Factors Promote the Generation of Follicular Helper T Cells in Response to Acute Viral Infection. J Immunol. American Association of Immunologists; 2016 Mar. 1; 196(5):2015-2019. PMCID: PMC4761453
22. Cubas R, van Grevenynghe J, Wills S, Kardava L, Santich B H, Buckner C M, Muir R, Tardif V, Nichols C, Procopio F, He Z, Metcalf T, Ghneim K, Locci M, Ancuta P, Routy J-P, Trautmann L, Li Y, McDermott A B, Koup R A, Petrovas C, Migueles S A, Connors M, Tomaras G D, Moir S, Crotty S, Haddad E K. Reversible Reprogramming of Circulating Memory T Follicular Helper Cell Function during Chronic HIV Infection. J Immunol. 2015 Dec. 15; 195(12):5625-5636. PMCID: PMC4670798
23. Streeck H, D'Souza M P, Littman D R, Crotty S. Harnessing CD4+ T cell responses in HIV vaccine development. Nat Med. Nature Research; 2013 February; 19(2):143-149. PMCID: PMC3626561
24. Tam H H, Melo M B, Kang M, Pelet J M, Ruda V M, Foley M H, Hu J K, Kumari S, Crampton J, Baldeon A D, Sanders R W, Moore J P, Crotty S, Langer R, Anderson D G, Chakraborty A K, Irvine D J. Sustained antigen availability during germinal center initiation enhances antibody responses to vaccination. Proc Natl Acad Sci USA. 2016 Oct. 25; 113(43):E6639-E6648. PMCID: PMC5086995
25. Jardine J G, Kulp D W, Havenar-Daughton C, Sarkar A, Briney B, Sok D, Sesterhenn F, Erefio-Orbea J, Kalyuzhniy O, Deresa I, Hu X, Spencer S, Jones M, Georgeson E, Adachi Y, Kubitz M, deCamp A C, Julien J-P, Wilson I A, Burton D R, Crotty S, Schief W R. HIV-1 broadly neutralizing antibody precursor B cells revealed by germline-targeting immunogen. Science. American Association for the Advancement of Science; 2016 Mar. 25; 351(6280):1458-1463. PMCID: PMC4872700
26. Bélanger S, Crotty S. Dances with cytokines, featuring TFH cells, IL-21, IL-4 and B cells. Nature Publishing Group. Nature Research; 2016 Sep. 20; 17(10):1135-1136. PMID: 27648538. PMCID: in process
27. Locci M, Wu J E, Arumemi F, Mikulski Z, Dahlberg C, Miller A T, Crotty S. Activin A programs the differentiation of human TFH cells. Nature Publishing Group. Nature Research; 2016 August; 17(8):976-984. PMCID: PMC4955732
28. Kroenke M A, Eto D, Locci M, Cho M, Davidson T, Haddad E K, Crotty S. Bcl6 and Maf cooperate to instruct human follicular helper CD4 T cell differentiation. J Immunol. American Association of Immunologists; 2012 Apr. 15; 188(8):3734-3744. PMCID: PMC3324673
29. Choi Y S, Kageyama R, Eto D, Escobar T C, Johnston R J, Monticelli L, Lao C, Crotty S. ICOS receptor instructs T follicular helper cell versus effector cell differentiation via induction of the transcriptional repressor Bcl6. Immunity. 2011 Jun. 24; 34(6):932-946. PMCID: PMC3124577
30. Locci M, Havenar-Daughton C, Landais E, Wu J, Kroenke M A, Arlehamn C L, Su L F, Cubas R, Davis M M, Sette A, Haddad E K, International AIDS Vaccine Initiative Protocol C Principal Investigators, Poignard P, Crotty S. Human circulating PD-1+CXCR3−CXCR5+ memory Tfh cells are highly functional and correlate with broadly neutralizing HIV antibody responses. Immunity. 2013 Oct. 17; 39(4):758-769. PMCID: PMC3996844
31. Crotty S, Kersh E N, Cannons J, Schwartzberg P L, Ahmed R. SAP is required for generating long-term humoral immunity. Nature. Nature Publishing Group; 2003 Jan. 16; 421(6920):282-287. PMID: 12529646
32. Kageyama R, Cannons J L, Zhao F, Yusuf I, Lao C, Locci M, Schwartzberg P L, Crotty S. The receptor Ly108 functions as a SAP adaptor-dependent on-off switch for T cell help to B cells and NKT cell development. Immunity. 2012 Jun. 29; 36(6):986-1002. PMCID: PMC3389310
33. Johnston R J, Choi Y S, Diamond J A, Yang J A, Crotty S. STAT5 is a potent negative regulator of TFH cell differentiation. J Exp Med. Rockefeller University Press; 2012 Feb. 13; 209(2):243-250. PMCID: PMC3281266
34. Choi Y S, Gullicksrud J A, Xing S, Zeng Z, Shan Q, Li F, Love P E, Peng W, Xue H-H, Crotty S. LEF-1 and TCF-1 orchestrate T(FH) differentiation by regulating differentiation circuits upstream of the transcriptional repressor Bcl6. Nature Publishing Group. 2015 September; 16(9):980-990. PMCID: PMC4545301
35. Cubas R A, Mudd J C, Savoye A-L, Perreau M, van Grevenynghe J, Metcalf T, Connick E, Meditz A, Freeman G J, Abesada-Terk G, Jacobson J M, Brooks A D, Crotty S, Estes J D, Pantaleo G, Lederman M M, Haddad E K. Inadequate T follicular cell help impairs B cell immunity during HIV infection. Nat Med. 2013 April; 19(4):494-499. PMCID: PMC3843317
36. Baugh R F, Archer S M, Mitchell R B, Rosenfeld R M, Amin R, Burns J J, Darrow D H, Giordano T, Litman R S, Li K K, Mannix M E, Schwartz R H, Setzen G, Wald E R, Wall E, Sandberg G, Patel M M, American Academy of Otolaryngology-Head and Neck Surgery Foundation. Clinical practice guideline: tonsillectomy in children. Otolaryngology—head and neck surgery: official journal of American Academy of Otolaryngology-Head and Neck Surgery. SAGE PublicationsSage C A: Los Angeles, Calif.; 2011. p. S1-30. PMID: 21493257

37. Wigton R S, Connor J L, Centor R M. Transportability of a decision rule for the diagnosis of streptococcal pharyngitis. Arch Intern Med. 1986 January; 146(1):81-83. PMID: 3510600
38. Shulman S T, Bisno A L, Clegg H W, Gerber M A, Kaplan E L, Lee G, Martin J M, Van Beneden C, Infectious Diseases Society of America. Clinical practice guideline for the diagnosis and management of group A streptococcal pharyngitis: 2012 update by the Infectious Diseases Society of America. Clinical infectious diseases: an official publication of the Infectious Diseases Society of America. 2012. p. e86-102. PMID: 22965026
39. Van Brusselen D, Vlieghe E, Schelstraete P, De Meulder F, Vandeputte C, Garmyn K, Laffut W, Van de Voorde P. Streptococcal pharyngitis in children: to treat or not to treat? Eur J Pediatr. Springer Berlin Heidelberg; 2014 October; 173(10):1275-1283. PMID: 25113742
40. Mitchell R B, Kelly J. Behavior, neurocognition and quality-of-life in children with sleep-disordered breathing. Int J Pediatr Otorhinolaryngol. 2006 March; 70(3): 395-406. PMID: 16321451
41. Shea P, Ewbank A, Gonzalez-Lugo J, Martagon-Rosado A, Martinez-Gutierrez J, Rehman H, Serrano-Gonzalez M, Fittipaldi N, Beres S, Flores A, Low D, Willey B, Musser J. Group A *Streptococcus* emm Gene Types in Pharyngeal Isolates, Ontario, Canada, 2002-2010. Emerg Infect Dis. 2011 November; 17(11):1-8.
42. Haukness H A, Tanz R R, Thomson R B, Pierry D K, Kaplan E L, Beall B, Johnson D, Hoe N P, Musser J M, Shulman S T. The heterogeneity of endemic community pediatric group a streptococcal pharyngeal isolates and their relationship to invasive isolates. J INFECT DIS. Oxford University Press; 2002 Apr. 1; 185(7):915-920. PMID: 11920315
43. Roberts A L, Connolly K L, Kirse D J, Evans A K, Poehling K A, Peters T R, Reid S D. Detection of group A *Streptococcus* in tonsils from pediatric patients reveals high rate of asymptomatic streptococcalcarriage. BMC Pediatrics. BioMed Central Ltd; 2012 Jan. 9; 12(1):3.
44. Pontin I P O, Sanchez D C J, Di Francesco R. Asymptomatic Group A *Streptococcus* carriage in children with recurrent tonsillitis and tonsillar hypertrophy. Int J Pediatr Otorhinolaryngol. 2016 July; 86:57-59. PMID: 27260580
45. Jeong J H, Lee D W, Ryu R A, Lee Y S, Lee S H, Kang J O, Tae K. Bacteriologic comparison of tonsil core in recurrent tonsillitis and tonsillar hypertrophy. Laryngoscope. 2007 December; 117(12):2146-2151. PMID: 17909446
46. Kotb M, Norrby-Teglund A, McGeer A, El-Sherbini H, Dorak M T, Khurshid A, Green K, Peeples J, Wade J, Thomson G, Schwartz B, Low D E. An immunogenetic and molecular basis for differences in outcomes of invasive group A streptococcal infections. Nat Med. 2002 Nov. 18; 8(12):1398-1404.
47. Stanevicha V, Eglite J, Sochnevs A, Gardovska D, Zavadska D, Shantere R. HLA class II associations with rheumatic heart disease among clinically homogeneous patients in children in Latvia. Arthritis Res Ther. BioMed Central; 2003; 5(6):R340-6. PMCID: PMC333411
48. Stanevicha V, Eglite J, Zavadska D, Sochnevs A, Shantere R, Gardovska D. HLA class II DR and DQ genotypes and haplotypes associated with rheumatic fever among a clinically homogeneous patient population of Latvian children. Arthritis Res Ther. BioMed Central; 2007; 9(3):R58. PMCID: PMC2206337
49. Guédez Y, Kotby A, El-Demellawy M, Galal A, Thomson G, Zaher S, Kassem S, Kotb M. HLA class II associations with rheumatic heart disease are more evident and consistent among clinically homogeneous patients. Circulation. 1999 Jun. 1; 99(21):2784-2790. PMID: 10351973
50. Kudat H, Telci G, Sozen A B, Oguz F, Akkaya V, Ozcan M, Atilgan D, Carin M, Guven O. The role of HLA molecules in susceptibility to chronic rheumatic heart disease. Int J Immunogenet. Blackwell Science Ltd; 2006 February; 33(1):41-44. PMID: 16426242
51. Rehman S, Akhtar N, Ahmad W, Ayub Q, Mehdi S Q, Mohyuddin A. Human leukocyte antigen (HLA) class II association with rheumatic heart disease in Pakistan. J Heart Valve Dis. 2007 May; 16(3):300-304. PMID: 17578052
52. Haydardedeoğlu F E, Tutkak H, Köse K, Düzgün N. Genetic susceptibility to rheumatic heart disease and streptococcal pharyngitis: association with HLA-DR alleles. Tissue Antigens. Blackwell Publishing Ltd; 2006 October; 68(4):293-296. PMID: 17026463
53. da Silva Antunes R, Paul S, Sidney J, Weiskopf D, Dan J M, Phillips E, Mallal S, Crotty S, Sette A, Lindestam Arlehamn C S. Definition of Human Epitopes Recognized in Tetanus Toxoid and Development of an Assay Strategy to Detect Ex Vivo Tetanus CD4$^+$ T Cell Responses. Bansal G P, editor. PLoS ONE. 2017; 12(1):e0169086. PMID: 28081174. PMCID: PMC5230748
54. Kasper K J, Zeppa J J, Wakabayashi A T, Xu S X, Mazzuca D M, Welch I, Baroja M L, Kotb M, Cairns E, Cleary P P, Haeryfar S M M, McCormick J K. Bacterial Superantigens Promote Acute Nasopharyngeal Infection by *Streptococcus pyogenes* in a Human MHC Class II-Dependent Manner. DeLeo F R, editor. PLoS Pathogens. 2014 May 29; 10(5):e1004155-11.
55. Kazmi S U, Kansal R, Aziz R K, Hooshdaran M, Norrby-Teglund A, Low D E, Halim A B, Kotb M. Reciprocal, Temporal Expression of SpeA and SpeB by Invasive M1T1 Group A Streptococcal Isolates In Vivo. Infection and Immunity. 2001 Aug. 1; 69(8):4988-4995.
56. Aziz R K, Kotb M. Rise and Persistence of Global M1T1 Clone of *Streptococcus pyogenes*. Emerg Infect Dis. 2008 October; 14(10):1511-1517.
57. Chang H, Shen X, Huang G, Fu Z, Zheng Y, Wang L, Li C, Liu L, Shen Y, Liu X, Yang Y. Molecular analysis of *Streptococcus pyogenes* strains isolated from Chinese children with pharyngitis. Diagnostic Microbiology and Infectious Disease. 2011 February; 69(2):117-122.
58. Nandi S, Chakraborti A, Bakshi D K, Rani A, Kumar R, Ganguly N K. Association of pyrogenic exotoxin genes with pharyngitis and rheumatic fever/rheumatic heart disease among Indian isolates of *Streptococcus pyogenes*. Lett Appl Microbiol. 2002; 35(3):237-241. PMID: 12180948
59. Weiskopf D, Bangs D J, Sidney J, Kolla R V, De Silva A D, de Silva A M, Crotty S, Peters B, Sette A. Dengue virus infection elicits highly polarized CX3CR1+ cytotoxic CD4+ T cells associated with protective immunity. Proceedings of the National Academy of Sciences. 2015 Aug. 4; 112(31):E4256-E4263. PMCID: PMC4534238
60. Kumar A, Perdomo M F, Kantele A, Hedman L, Hedman K, Franssila R. Granzyme B mediated function of Parvovirus B19-specific CD4(+) T cells. Clin Transl Immunology. Nature Publishing Group; 2015 July; 4(7):e39. PMCID: PMC4524951
61. Casazza J P, Betts M R, Price D A, Precopio M L, Ruff L E, Brenchley J M, Hill B J, Roederer M, Douek D C, Koup R A. Acquisition of direct antiviral effector functions by CMV-specific CD4+T lymphocytes with cellular maturation. J Exp Med. 2006 Dec. 26; 203(13):2865-2877.
62. Hanley P J, Cruz C R Y, Savoldo B, Leen A M, Stanojevic M, Khalil M, Decker W, Molldrem J J, Liu H, Gee A P, Rooney C M, Heslop H E, Dotti G, Brenner M K, Shpall E J, Bollard C M. Functionally active virus-specific T cells that target CMV, adenovirus, and EBV can be expanded from naive T-cell populations in cord blood and will target a range of viral epitopes. Blood. American Society of Hematology; 2009 Aug. 27; 114(9):1958-1967. PMCID: PMC2738578
63. Johnson S, Eller M, Teigler J E, Maloveste S M, Schultz B T, Soghoian D Z, Lu R, Oster A F, Chenine A L, Alter G, Dittmer U, Marovich M, Robb M L, Michael N L, Bolton D, Streeck H. Cooperativity of HIVSpecific Cytolytic CD4 T Cells and CD8 T Cells in Control of HIV Viremia. Silvestri G, editor. J Virol. 2015 Jul. 8; 89(15):7494-7505.
64. Laher F, Ranasinghe S, Porichis F, Mewalal N, Pretorius K, Ismail N, Buus S, Stryhn A, Carrington M, Walker B D, Ndung'u T, Ndhlovu Z M. HIV controllers exhibit enhanced frequencies of MHC class II tetramer+ Gag-specific CD4+ T cells in chronic clade C HIV-1 infection. J Virol. 2017 Jan. 11; JVI.02477-16. PMID: 28077659
65. Sun Q, Burton R L, Lucas K G. Cytokine production and cytolytic mechanism of CD4(+) cytotoxic T lymphocytes in ex vivo expanded therapeutic Epstein-Barr virus-specific T-cell cultures. Blood. 2002 May 1; 99(9):3302-3309. PMID: 11964297
66. Shan L, Deng K, Shroff N S, Durand C M, Rabi S A, Yang H-C, Zhang H, Margolick J B, Blankson J N, Siliciano R F. Stimulation of HIV-1-specific cytolytic T lymphocytes facilitates elimination of latent viral reservoir after virus reactivation. Immunity. 2012 Mar. 23; 36(3):491-501. PMCID: PMC3501645
67. Raveney B J E, Oki S, Hohjoh H, Nakamura M, Sato W, Murata M, Yamamura T. Eomesoderminexpressing T-helper cells are essential for chronic neuroinflammation. Nat Comms. Nature Publishing Group; 2015 Oct. 5; 6:8437. PMCID: PMC4600741
68. Takeuchi A, Badr MESG, Miyauchi K, Ishihara C, Onishi R, Guo Z, Sasaki Y, Ike H, Takumi A, Tsuji N M, Murakami Y, Katakai T, Kubo M, Saito T. CRTAM determines the CD4+ cytotoxic T lymphocyte lineage. J Exp Med. 2016 Jan. 11; 213(1):123-138. PMCID: PMC4710199
69. Collins A, Hewitt S L, Chaumeil J, Sellars M, Micsinai M, Allinne J, Parisi F, Nora E P, Bolland D J, Corcoran A E, Kluger Y, Bosselut R, Ellmeier W, Chong M M W, Littman D R, Skok J A. RUNX transcription factor-mediated association of Cd4 and Cd8 enables coordinate gene regulation. Immunity. 2011 Mar. 25; 34(3):303-314. PMCID: PMC3101577
70. Kaplan E L, Wotton J T, Johnson D R. Dynamic epidemiology of group A streptococcal serotypes associated with pharyngitis. The Lancet. 2001 Oct. 20; 358 (9290):1334-1337. PMID: 11684215
71. Tart A H, Walker M J, Musser J M. New understanding of the group A *Streptococcus* pathogenesis cycle. Trends Microbiol. 2007 July; 15(7):318-325. PMID: 17524649
72. Abe J, Forrester J, Nakahara T, Lafferty J A, Kotzin B L, Leung D Y. Selective stimulation of human T cells with streptococcal erythrogenic toxins A and B. The Journal of Immunology. 1991 Jun. 1; 146(11):3747-3750. PMID: 1903412
73. Mascini E M, Jansze M, Schellekens J F, Musser J M, Faber J A, Verhoef-Verhage L A, Schouls L, van Leeuwen W J, Verhoef J, van Dijk H. Invasive group A streptococcal disease in the Netherlands: evidence for a protective role of anti-exotoxin A antibodies. J INFECT DIS. 2000 February; 181(2):631-638. PMID: 10669348
74. Sundberg E, Jardetzky T S. Structural basis for HLA-DQ binding by the streptococcal superantigen SSA. Nat Struct Biol. 1999 February; 6(2):123-129. PMID: 10048922
75. Norrby-Teglund A, Nepom G T, Kotb M. Differential presentation of group A streptococcal superantigens by HLA class II DQ and DR alleles. Eur J Immunol. WILEY-VCH Verlag; 2002 September; 32(9):2570-2577. PMID: 12207341
76. McKinney D M, Southwood S, Hinz D, Oseroff C, Arlehamn C S L, Schulten V, Taplitz R, Broide D, Hanekom W A, Scriba T J, Wood R, Alam R, Peters B, Sidney J, Sette A. A strategy to determine HLA class II restriction broadly covering the DR, DP, and DQ allelic variants most commonly expressed in the general population. Immunogenetics. 2013 May; 65(5):357-370. PMCID: PMC3633633
77. Llewelyn M, Sriskandan S, Peakman M, Ambrozak D R, Douek D C, Kwok W W, Cohen J, Altmann D M. HLA class II polymorphisms determine responses to bacterial superantigens. The Journal of Immunology. 2004 Feb. 1; 172(3):1719-1726. PMID: 14734754
78. Llewelyn M. Human leukocyte antigen class II haplotypes that protect against or predispose to streptococcal toxic shock. Clin Infect Dis. 2005 Nov. 15; 41 Suppl 7(Supplement 7):S445-8. PMID: 16237645
79. Reglinski M, Sriskandan S. The contribution of group A streptococcal virulence determinants to the pathogenesis of sepsis. Virulence. 2014 Jan. 1; 5(1):127-136. PMCID: PMC3916366
80. Chen L, Flies D B. Molecular mechanisms of T cell co-stimulation and co-inhibition. Nature Reviews Immunology. Nature Publishing Group; 2013 April; 13(4):227-242. PMCID: PMC3786574
81. Aziz R K, Pabst M J, Jeng A, Kansal R, Low D E, Nizet V, Kotb M. Invasive M1T1 group A *Streptococcus* undergoes a phase-shift in vivo to prevent proteolytic degradation of multiple virulence factors by SpeB. Molecular Microbiology. 2003 Nov. 11; 51(1):123-134.
82. Chatellier S, Ihendyane N, Kansal R G, Khambaty F, Basma H, Norrby-Teglund A, Low D E, Mcgeer A, Kotb M. Genetic relatedness and superantigen expression in group A *streptococcus* serotype M1 isolates from patients with severe and nonsevere invasive diseases. Infection and Immunity. American Society for Microbiology (ASM); 2000 June; 68(6):3523-3534. PMCID: PMC97638
83. Reid S D, Hoe N P, Smoot L M, Musser J M. Group A *Streptococcus*: allelic variation, population genetics, and host-pathogen interactions. J Clin Invest. American Society for Clinical Investigation; 2001 February; 107(4):393-399. PMCID: PMC199275
84. McLeod J D, Walker L S, Patel Y I, Boulougouris G, Sansom D M. Activation of human T cells with superantigen (staphylococcal enterotoxin B) and CD28 confers resistance to apoptosis via CD95. The Journal of Immunology. 1998 Mar. 1; 160(5):2072-2079. PMID: 9498743
85. Lin L, Couturier J, Yu X, Medina M A, Kozinetz C A, Lewis D E. Granzyme B secretion by human memory CD4 T cells is less strictly regulated compared to memory CD8 T cells. BMC Immunol. 2014 Sep. 24; 15(1):57-15.

86. Mbitikon-Kobo F-M, Bonneville M, Sékaly R-P, Trautmann L. Ex vivo measurement of the cytotoxic capacity of human primary antigen-specific CD8 T cells. J Immunol Methods. 2012 January; 375(1-2):252-257.
87. Elavazhagan S, Fatehchand K, Santhanam V, Fang H, Ren L, Gautam S, Reader B, Mo X, Cheney C, Briercheck E, Vasilakos J P, Dietsch G N, Hershberg R M, Caligiuri M, Byrd J C, Butchar J P, Tridandapani S. Granzyme B expression is enhanced in human monocytes by TLR8 agonists and contributes to antibody-dependent cellular cytotoxicity. J Immunol. American Association of Immunologists; 2015 Mar. 15; 194(6):2786-2795. PMCID: PMC4355383
88. Bentebibel S-E, Schmitt N, Banchereau J, Ueno H. Human tonsil B-cell lymphoma 6 (BCL6)-expressing CD4+ T-cell subset specialized for B-cell help outside germinal centers. Proc Natl Acad Sci USA. 2011 Aug. 16; 108(33):E488-97. PMCID: PMC3158181
89. Rutishauser R L, Martins G A, Kalachikov S, Chandele A, Parish I A, Meffre E, Jacob J, Calame K, Kaech S M. Transcriptional repressor Blimp-1 promotes CD8(+) T cell terminal differentiation and represses the acquisition of central memory T cell properties. Immunity. 2009 Aug. 21; 31(2):296-308. PMCID: PMC2783637
90. Pearce E L, Mullen A C, Martins G A, Krawczyk C M, Hutchins A S, Zediak V P, Banica M, DiCioccio C B, Gross D A, Mao C-A, Shen H, Cereb N, Yang S Y, Lindsten T, Rossant J, Hunter C A, Reiner S L. Control of effector CD8+ T cell function by the transcription factor Eomesodermin. Science. 2003 Nov. 7; 302(5647):1041-1043. PMID: 14605368
91. Intlekofer A M, Takemoto N, Wherry E J, Longworth S A, Northrup J T, Palanivel V R, Mullen A C, Gasink C R, Kaech S M, Miller J D, Gapin L, Ryan K, Russ A P, Lindsten T, Orange J S, Goldrath A W, Ahmed R, Reiner S L Effector and memory CD8+ T cell fate coupled by T-bet and eomesodermin. Nat Immunol. 2005 Nov. 6; 6(12):1236-1244. PMID: 16273099
92. Cruz-Guilloty F, Pipkin M E, Djuretic I M, Levanon D, Lotem J, Lichtenheld M G, Groner Y, Rao A. Runx3 and T-box proteins cooperate to establish the transcriptional program of effector CTLs. J Exp Med. 2009 Jan. 19; 206(1):51-59.
93. Hatzi K, Nance J P, Kroenke M A, Bothwell M, Haddad E K, Melnick A, Crotty S. BCL6 orchestrates Tfh cell differentiation via multiple distinct mechanisms. J Exp Med. 2015 Apr. 6; 212(4):539-553. PMCID: PMC4387288
94. Schmitt N, Liu Y, Bentebibel S-E, Ueno H. Molecular Mechanisms Regulating T Helper 1 versus T Follicular Helper Cell Differentiation in Humans. Cell Rep. 2016 Jul. 26; 16(4):1082-1095. PMID: 27425607
95. Mucida D, Husain M M, Muroi S, van Wijk F, Shinnakasu R, Naoe Y, Reis B S, Huang Y, Lambolez F, Docherty M, Attinger A, Shui J-W, Kim G, Lena C J, Sakaguchi S, Miyamoto C, Wang P, Atarashi K, Park Y, Nakayama T, Honda K, Ellmeier W, Kronenberg M, Taniuchi I, Cheroutre H. Transcriptional reprogramming of mature CD4+ helper T cells generates distinct MHC class II-restricted cytotoxic T lymphocytes. Nat Immunol. 2013 Jan. 20; 14(3):281-289.
96. Qui H Z, Hagymasi A T, Bandyopadhyay S, St Rose M-C, Ramanarasimhaiah R, Ménoret A, Mittler R S, Gordon S M, Reiner S L, Vella A T, Adler A J. CD134 plus CD137 dual costimulation induces Eomesodermin in CD4 T cells to program cytotoxic Th1 differentiation. J Immunol. American Association of Immunologists; 2011 Oct. 1; 187(7):3555-3564. PMCID: PMC3178659
97. Hrvatin S, Deng F, O'Donnell C W, Gifford D K, Melton D A. MARIS: method for analyzing RNA following intracellular sorting. Aalto-Setala K, editor. PLoS ONE. Public Library of Science; 2014; 9(3):e89459. PMCID: PMC3940959
98. Linterman M A, Pierson W, Lee S K, Kallies A, Kawamoto S, Rayner T F, Srivastava M, Divekar D P, Beaton L, Hogan J J, Fagarasan S, Liston A, Smith K G C, Vinuesa C G. Foxp3+ follicular regulatory T cells control the germinal center response. Nat Med. Nature Publishing Group; 2011 Jul. 24; 17(8):975-982.
99. Cao X, Cai S F, Fehniger T A, Song J, Collins L I, Piwnica-Worms D R, Ley T J. Granzyme B and perforin are important for regulatory T cell-mediated suppression of tumor clearance. Immunity. 2007 October; 27(4):635-646. PMID: 17919943
100. Medina M A, Couturier J, Feske M L, Mahne A E, Turner M, Yu X, Kozinetz C A, Orozco A F, Hutchison A T, Savidge T C, Rodgers J R, Lewis D E. Granzyme B- and Fas ligand-mediated cytotoxic function induced by mitogenic CD28 stimulation of human memory CD4+ T cells. J Leukoc Biol. Society for Leukocyte Biology; 2012 May; 91(5):759-771. PMCID: PMC3336770
101. Krzewski K, Gil-Krzewska A, Nguyen V, Peruzzi G, Coligan J E. LAMP1/CD107a is required for efficient perforin delivery to lytic granules and NK-cell cytotoxicity. Blood. American Society of Hematology; 2013 Jun. 6; 121(23):4672-4683. PMCID: PMC3674668
102. Ma C S, Suryani S, Avery D T, Chan A, Nanan R, Santner-Nanan B, Deenick E K, Tangye S G. Early commitment of naïve human CD4+ T cells to the T follicular helper (TFH) cell lineage is induced by IL-12. Immunology and Cell Biology. Nature Publishing Group; 2009 Sep. 1; 87(8):590-600. PMID: 19721453
103. Schmitt N, Morita R, Bourdery L, Bentebibel S-E, Zurawski S M, Banchereau J, Ueno H. Human dendritic cells induce the differentiation of interleukin-21-producing T follicular helper-like cells through interleukin-12. Immunity. 2009 Jul. 17; 31(1):158-169. PMCID: PMC2731623
104. Miettinen M, Matikainen S, Vuopio-Varkila J, Pirhonen J, Varkila K, Kurimoto M, Julkunen I. Lactobacilli and streptococci induce interleukin-12 (IL-12), IL-18, and gamma interferon production in human peripheral blood mononuclear cells. Infection and Immunity. American Society for Microbiology (ASM); 1998 December; 66(12):6058-6062. PMCID: PMC108774
105. LaRock C N, Todd J, LaRock D L, Olson J. IL-1β is an innate immune sensor of microbial proteolysis. risk. 2016.
106. LaRock C N, Nizet V. Inflammasome/IL-1β Responses to Streptococcal Pathogens. Front Immunol. Frontiers; 2015; 6:518. PMCID: PMC4597127
107. Morita R, Schmitt N, Bentebibel S-E, Ranganathan R, Bourdery L, Zurawski G, Foucat E, Dullaers M, Oh S, Sabzghabaei N, Lavecchio E M, Punaro M, Pascual V, Banchereau J, Ueno H. Human blood CXCR5(+)CD4(+) T cells are counterparts of T follicular cells and contain specific subsets that differentially support antibody secretion. Immunity. 2011 Jan. 28; 34(1):108-121. PMCID: PMC3046815
108. Choi Y S, Yang J A, Yusuf I, Johnston R J, Greenbaum J, Peters B, Crotty S. Bcl6 expressing follicular helper CD4 T cells are fate committed early and have the capacity to form memory. J Immunol. American Association of Immunologists; 2013 Apr. 15; 190(8):4014-4026. PMCID: PMC3626566

References Cited in Examples 7-13

1. Johnston R J, Poholek A C, DiToro D, Yusuf I, Eto D, Barnett B, Dent A L, Craft J, Crotty S. Bcl6 and Blimp-1 are reciprocal and antagonistic regulators of T follicular helper cell differentiation. Science. American Association for the Advancement of Science; 2009 Aug. 21; 325 (5943):1006-1010. PMCID: PMC2766560
2. Choi Y S, Kageyama R, Eto D, Escobar T C, Johnston R J, Monticelli L, Lao C, Crotty S. ICOS receptor instructs T follicular helper cell versus effector cell differentiation via induction of the transcriptional repressor Bcl6. Immunity. 2011 Jun. 24; 34(6):932-946. PMCID: PMC3124577
3. Crotty S. Follicular helper CD4 T cells (TFH). Annu Rev Immunol. 2011; 29(1):621-663. PMID: 21314428
4. Crotty S. T Follicular Helper Cell Differentiation, Function, and Roles in Disease. Immunity. Elsevier Inc; 2014 Oct. 16; 41(4):529-542. PMCID: PMC4223692
5. Ebell M H, Smith M A, Barry H C, Ives K, Carey M. The rational clinical examination. Does this patient have strep throat? JAMA. 2000 Dec. 13; 284(22):2912-2918. PMID: 11147989
6. Ferretti J J, McShan W M, Ajdic D, Savic D J, Savic G, Lyon K, Primeaux C, Sezate S, Suvorov A N, Kenton S, Lai H S, Lin S P, Qian Y, Jia H G, Najar F Z, Ren Q, Zhu H, Song L, White J, Yuan X, Clifton S W, Roe B A, McLaughlin R. Complete genome sequence of an M1 strain of Streptococcus pyogenes. Proceedings of the National Academy of Sciences. 2001 Apr. 10; 98(8):4658-4663. PMCID: PMC31890
7. Nurieva R I, Chung Y, Martinez G J, Yang X O, Tanaka S, Matskevitch T D, Wang Y-H, Dong C. Bcl6 mediates the development of T follicular helper cells. Science. 2009 Aug. 21; 325(5943):1001-1005. PMCID: PMC2857334
8. Yu D, Rao S, Tsai L M, Lee S K, He Y, Sutcliffe E L, Srivastava M, Linterman M, Zheng L, Simpson N, Ellyard J I, Parish I A, Ma C S, Li Q-J, Parish C R, Mackay C R, Vinuesa C G. The transcriptional repressor Bcl-6 directs T follicular helper cell lineage commitment. Immunity. 2009 Sep. 18; 31(3):457-468. PMID: 19631565
9. Victora G D, Dominguez-Sola D, Holmes A B, Deroubaix S, Dalla-Favera R, Nussenzweig M C. Identification of human germinal center light and dark zone cells and their relationship to human B-cell lymphomas. Blood. American Society of Hematology; 2012 Sep. 13; 120(11):2240-2248. PMCID: PMC3447782
10. Crotty S. T follicular helper cell differentiation, function, and roles in disease. Immunity. Elsevier Inc; 2014 Oct. 16; 41(4):529-542. PMCID: PMC4223692
11. Gitlin A D, Shulman Z, Nussenzweig M C. Clonal selection in the germinal centre by regulated proliferation and hypermutation. Nature. Nature Research; 2014 May 29; 509(7502):637-640. PMCID:PMC4271732
12. Crotty S. Follicular Helper CD4 T Cells (T FH). Annu Rev Immunol. 2011 Apr. 23; 29(1):621-663.
13. Locci M, Havenar-Daughton C, Landais E, Wu J, Kroenke M A, Arlehamn C L, Su L F, Cubas R, Davis M M, Sette A, Haddad E K, International AIDS Vaccine Initiative Protocol C Principal Investigators, Poignard P, Crotty S. Human circulating PD-1+CXCR3−CXCR5+ memory Tfh cells are highly functional and correlate with broadly neutralizing HIV antibody responses. Immunity. Elsevier Inc; 2013 Oct. 17; 39(4):758-769. PMCID: PMC3996844
14. Benhnia M R-E-I, McCausland M M, Laudenslager J, Granger S W, Rickert S, Koriazova L, Tahara T, Kubo R T, Kato S, Crotty S. Heavily isotype-dependent protective activities of human antibodies against vaccinia virus extracellular virion antigen B5. J Virol. 2009 December; 83(23):12355-12367. PMCID: PMC2786738
15. Crotty S, Felgner P, Davies H, Glidewell J, Villarreal L, Ahmed R. Cutting edge: long-term B cell memory in humans after smallpox vaccination. The Journal of Immunology. 2003 Nov. 15; 171(10):4969-4973. PMID: 14607890
16. Moyron-Quiroz J E, McCausland M M, Kageyama R, Sette A, Crotty S. The smallpox vaccine induces an early neutralizing IgM response. Vaccine. 2009 Dec. 10; 28(1): 140-147. PMCID: PMC2788018
17. Havenar-Daughton C, Lindqvist M, Heit A, Wu J E, Reiss S M, Kendric K, Bélanger S, Kasturi S P, Landais E, Akondy R S, McGuire H M, Bothwell M, Vagefi P A, Scully E, IAVI Protocol C Principal Investigators, Tomaras G D, Davis M M, Poignard P, Ahmed R, Walker B D, Pulendran B, McElrath M J, Kaufmann D E, Crotty S. CXCL13 is a plasma biomarker of germinal center activity. Proc Natl Acad Sci USA. National Acad Sciences; 2016 Mar. 8; 113(10):2702-2707. PMCID: PMC4790995
18. Hong J J, Amancha P K, Rogers K A, Courtney C L, Havenar-Daughton C, Crotty S, Ansari A A, Villinger F. Early lymphoid responses and germinal center formation correlate with lower viral load set points and better prognosis of simian immunodeficiency virus infection. J Immunol. American Association of Immunologists; 2014 Jul. 15; 193(2):797-806. PMCID: PMC4084862
19. Boettler T, Choi Y S, Salek-Ardakani S, Cheng Y, Moeckel F, Croft M, Crotty S, Herrath von M. Exogenous OX40 stimulation during lymphocytic choriomeningitis virus infection impairs follicular Th cell differentiation and diverts CD4 T cells into the effector lineage by upregulating Blimp-1. J Immunol. American Association of Immunologists; 2013 Nov. 15; 191(10):5026-5035. PMCID: PMC3915873
20. Landais E, Huang X, Havenar-Daughton C, Murrell B, Price M A, Wickramasinghe L, Ramos A, Bian C B, Simek M, Allen S, Karita E, Kilembe W, Lakhi S, Inambao M, Kamali A, Sanders E J, Anzala O, Edward V, Bekker L-G, Tang J, Gilmour J, Kosakovsky-Pond S L, Phung P, Wrin T, Crotty S, Godzik A, Poignard P. Broadly Neutralizing Antibody Responses in a Large Longitudinal Sub-Saharan HIV Primary Infection Cohort. Trkola A, editor. PLoS Pathogens. Public Library of Science; 2016 January; 12(1):e1005369. PMCID: PMC4713061
21. Havenar-Daughton C, Carnathan D G, Torrents de la Peña A, Pauthner M, Briney B, Reiss S M, Wood J S, Kaushik K, van Gils M J, Rosales S L, van der Woude P, Locci M, Le K M, de Taeye S W, Sok D, Mohammed A U R, Huang J, Gumber S, Garcia A, Kasturi S P, Pulendran B, Moore J P, Ahmed R, Seumois G, Burton D R, Sanders R W, Silvestri G, Crotty S. Direct Probing of Germinal Center Responses Reveals Immunological Features and Bottlenecks for Neutralizing Antibody Responses to HIV Env Trimer. Cell Rep. 2016 Nov. 22; 17(9):2195-2209. PMCID: PMC5142765
22. Martinez G J, Hu J K, Pereira R M, Crampton J S, Togher S, Bild N, Crotty S, Rao A. Cutting Edge: NFAT Transcription Factors Promote the Generation of Follicular Helper T Cells in Response to Acute Viral Infection. J Immunol. American Association of Immunologists; 2016 Mar. 1; 196(5):2015-2019. PMCID: PMC4761453
23. Cubas R A, Mudd J C, Savoye A-L, Perreau M, van Grevenynghe J, Metcalf T, Connick E, Meditz A, Freeman G J, Abesada-Terk G, Jacobson J M, Brooks A D, Crotty S, Estes J D, Pantaleo G, Lederman M M, Haddad E K. Inadequate T follicular cell help impairs B cell immunity during HIV infection. Nat Med. 2013 April; 19(4):494-499. PMCID: PMC3843317
24. Streeck H, D'Souza M P, Littman D R, Crotty S. Harnessing CD4+ T cell responses in HIV vaccine development. Nat Med. Nature Research; 2013 February; 19(2):143-149. PMCID: PMC3626561
25. Tam H H, Melo M B, Kang M, Pelet J M, Ruda V M, Foley M H, Hu J K, Kumari S, Crampton J, Baldeon A D, Sanders R W, Moore J P, Crotty S, Langer R, Anderson D G, Chakraborty A K, Irvine D J. Sustained antigen availability during germinal center initiation enhances antibody responses to vaccination. Proc Natl Acad Sci USA. 2016 Oct. 25; 113(43):E6639-E6648. PMCID: PMC5086995
26. Jardine J G, Kulp D W, Havenar-Daughton C, Sarkar A, Briney B, Sok D, Sesterhenn F, Erefio-Orbea J, Kalyuzhniy O, Deresa I, Hu X, Spencer S, Jones M, Georgeson E, Adachi Y, Kubitz M, deCamp A C, Julien J-P, Wilson I A, Burton D R, Crotty S, Schief W R. HIV-1 broadly neutralizing antibody precursor B cells revealed by germline-targeting immunogen. Science. American Association for the Advancement of Science; 2016 Mar. 25; 351(6280):1458-1463. PMCID: PMC4872700
27. Bélanger S, Crotty S. Dances with cytokines, featuring TFH cells, IL-21, IL-4 and B cells. Nature Publishing Group. Nature Research; 2016 Sep. 20; 17(10):1135-1136. PMID: 27648538. PMCID: in process
28. Locci M, Wu J E, Arumemi F, Mikulski Z, Dahlberg C, Miller A T, Crotty S. Activin A programs the differentiation of human TFH cells. Nature Publishing Group. Nature Research; 2016 August; 17(8):976-984. PMCID: PMC4955732
29. Kroenke M A, Eto D, Locci M, Cho M, Davidson T, Haddad E K, Crotty S. Bcl6 and Maf cooperate to instruct human follicular helper CD4 T cell differentiation. J Immunol. American Association of Immunologists; 2012 Apr. 15; 188(8):3734-3744. PMCID: PMC3324673
30. Hatzi K, Nance J P, Kroenke M A, Bothwell M, Haddad E K, Melnick A, Crotty S. BCL6 orchestrates Tfh cell differentiation via multiple distinct mechanisms. J Exp Med. 2015 Apr. 6; 212(4):539-553. PMCID: PMC4387288
31. Locci M, Havenar-Daughton C, Landais E, Wu J, Kroenke M A, Arlehamn C L, Su L F, Cubas R, Davis M M, Sette A, Haddad E K, International AIDS Vaccine Initiative Protocol C Principal Investigators, Poignard P, Crotty S. Human circulating PD-1+CXCR3−CXCR5+ memory Tfh cells are highly functional and correlate with broadly neutralizing HIV antibody responses. Immunity. 2013 Oct. 17; 39(4):758-769. PMCID: PMC3996844
32. Crotty S, Kersh E N, Cannons J, Schwartzberg P L, Ahmed R. SAP is required for generating long-term humoral immunity. Nature. Nature Publishing Group; 2003 Jan. 16; 421(6920):282-287. PMID: 12529646
33. Kageyama R, Cannons J L, Zhao F, Yusuf I, Lao C, Locci M, Schwartzberg P L, Crotty S. The receptor Ly108 functions as a SAP adaptor-dependent on-off switch for T cell help to B cells and NKT cell development. Immunity. 2012 Jun. 29; 36(6):986-1002. PMCID: PMC3389310
34. Johnston R J, Choi Y S, Diamond J A, Yang J A, Crotty S. STAT5 is a potent negative regulator of TFH cell differentiation. J Exp Med. Rockefeller University Press; 2012 Feb. 13; 209(2):243-250. PMCID: PMC3281266
35. Cubas R, van Grevenynghe J, Wills S, Kardava L, Santich B H, Buckner C M, Muir R, Tardif V, Nichols C, Procopio F, He Z, Metcalf T, Ghneim K, Locci M, Ancuta P, Routy J-P, Trautmann L, Li Y, McDermott A B, Koup R A, Petrovas C, Migueles S A, Connors M, Tomaras G D, Moir S, Crotty S, Haddad E K. Reversible Reprogramming of Circulating Memory T Follicular Helper Cell Function during Chronic HIV Infection. J Immunol. 2015 Dec. 15; 195(12):5625-5636. PMCID: PMC4670798
36. Choi Y S, Gullicksrud J A, Xing S, Zeng Z, Shan Q, Li F, Love P E, Peng W, Xue H-H, Crotty S. LEF-1 and TCF-1 orchestrate T(FH) differentiation by regulating differentiation circuits upstream of the transcriptional repressor Bcl6. Nature Publishing Group. 2015 September; 16(9):980-990. PMCID: PMC4545301
37. Dan J M, Lindestam Arlehamn C S, Weiskopf D, da Silva Antunes R, Havenar-Daughton C, Reiss S M, Brigger M, Bothwell M, Sette A, Crotty S. A Cytokine-Independent Approach To Identify Antigen-Specific Human Germinal Center T Follicular Helper Cells and Rare Antigen-Specific CD4+ T Cells in Blood. J Immunol. American Association of Immunologists; 2016 Aug. 1; 197(3):983-993. PMCID: PMC4955771
38. Havenar-Daughton C, Reiss S M, Carnathan D G, Wu J E, Kendric K, Torrents de la Peña A, Kasturi S P, Dan J M, Bothwell M, Sanders R W, Pulendran B, Silvestri G, Crotty S. Cytokine-Independent Detection of Antigen-Specific Germinal Center T Follicular Helper Cells in Immunized Nonhuman Primates Using a Live Cell Activation-Induced Marker Technique. J Immunol. American Association of Immunologists; 2016 Aug. 1; 197(3):994-1002. PMCID: PMC4955744
39. da Silva Antunes R, Paul S, Sidney J, Weiskopf D, Dan J M, Phillips E, Mallal S, Crotty S, Sette A, indestam Arlehamn C S. Definition of Human Epitopes Recognized in Tetanus Toxoid and Development of an Assay Strategy to Detect Ex Vivo Tetanus CD4+ T Cell Responses. Bansal G P, editor. PLoS ONE. 2017; 12(1):e0169086. PMID: 28081174. PMCID: PMC5230748
40. Baugh R F, Archer S M, Mitchell R B, Rosenfeld R M, Amin R, Burns J J, Darrow D H, Giordano T, Litman R S, Li K K, Mannix M E, Schwartz R H, Setzen G, Wald E R, Wall E, Sandberg G, Patel M M, American Academy of Otolaryngology-Head and Neck Surgery Foundation. Clinical practice guideline: tonsillectomy in children. Otolaryngology—head and neck surgery: official journal of American Academy of Otolaryngology-Head and Neck Surgery. SAGE Publications Sage C A: Los Angeles, Calif.; 2011. p. S1-30. PMID: 21493257
41. Wigton R S, Connor J L, Centor R M. Transportability of a decision rule for the diagnosis of streptococcal pharyngitis. Arch Intern Med. 1986 January; 146(1):81-83. PMID: 3510600
42. Shulman S T, Bisno A L, Clegg H W, Gerber M A, Kaplan E L, Lee G, Martin J M, Van Beneden C, Infectious Diseases Society of America. Clinical practice guideline for the diagnosis and management of group A streptococcal pharyngitis: 2012 update by the Infectious Diseases Society of America. Clinical infectious diseases: an official publication of the Infectious Diseases Society of America. 2012. p. e86-102. PMID: 22965026
43. Van Brusselen D, Vlieghe E, Schelstraete P, De Meulder F, Vandeputte C, Garmyn K, Laffut W, Van de Voorde P.

Streptococcal pharyngitis in children: to treat or not to treat? Eur J Pediatr. Springer Berlin Heidelberg; 2014 October; 173(10):1275-1283. PMID: 25113742
44. Mitchell R B, Kelly J. Behavior, neurocognition and quality-of-life in children with sleep-disordered breathing. Int J Pediatr Otorhinolaryngol. 2006 March; 70(3): 395-406. PMID: 16321451
45. Shea P, Ewbank A, Gonzalez-Lugo J, Martagon-Rosado A, Martinez-Gutierrez J, Rehman H, Serrano-Gonzalez M, Fittipaldi N, Beres S, Flores A, Low D, Willey B, Musser J. Group A Streptococcus emm Gene Types in Pharyngeal Isolates, Ontario, Canada, 2002-2010. Emerg Infect Dis. 2011 November; 17(11):1-8.
46. Haukness H A, Tanz R R, Thomson R B, Pierry D K, Kaplan E L, Beall B, Johnson D, Hoe N P, Musser J M, Shulman S T. The heterogeneity of endemic community pediatric group a streptococcal pharyngeal isolates and their relationship to invasive isolates. J INFECT DIS. Oxford University Press; 2002 Apr. 1; 185(7):915-920. PMID: 11920315
47. Roberts A L, Connolly K L, Kirse D J, Evans A K, Poehling K A, Peters T R, Reid S D. Detection of group A Streptococcus in tonsils from pediatric patients reveals high rate of asymptomatic streptococcal carriage. BMC Pediatrics. BioMed Central Ltd; 2012 Jan. 9; 12(1):3.
48. Pontin I P O, Sanchez D C J, Di Francesco R. Asymptomatic Group A Streptococcus carriage in children with recurrent tonsillitis and tonsillar hypertrophy. Int J Pediatr Otorhinolaryngol. 2016 July; 86:57-59. PMID: 27260580
49. Jeong J H, Lee D W, Ryu R A, Lee Y S, Lee S H, Kang J O, Tae K. Bacteriologic comparison of tonsil core in recurrent tonsillitis and tonsillar hypertrophy. Laryngoscope. 2007 December; 117(12):2146-2151. PMID: 17909446
50. Kotb M, Norrby-Teglund A, McGeer A, El-Sherbini H, Dorak M T, Khurshid A, Green K, Peeples J, Wade J, Thomson G, Schwartz B, Low D E. An immunogenetic and molecular basis for differences in outcomes of invasive group A streptococcal infections. Nat Med. 2002 Nov. 18; 8(12):1398-1404.
51. Stanevicha V, Eglite J, Sochnevs A, Gardovska D, Zavadska D, Shantere R. HLA class II associations with rheumatic heart disease among clinically homogeneous patients in children in Latvia. Arthritis Res Ther. BioMed Central; 2003; 5(6):R340-6. PMCID: PMC333411
52. Stanevicha V, Eglite J, Zavadska D, Sochnevs A, Shantere R, Gardovska D. HLA class II DR and DQ genotypes and haplotypes associated with rheumatic fever among a clinically homogeneous patient population of Latvian children. Arthritis Res Ther. BioMed Central; 2007; 9(3): R58. PMCID: PMC2206337
53. Shulman S T, Tanz R R, Dale J B, Beall B, Kabat W, Kabat K, Cederlund E, Patel D, Rippe J, Li Z, Sakota V, North American Streptococcal Pharyngitis Surveillance Group. Seven-Year Surveillance of North American Pediatric Group A Streptococcal Pharyngitis Isolates. Clinical Infectious Diseases. 2009 July; 49(1):78-84.
54. McKinney D M, Southwood S, Hinz D, Oseroff C, Arlehamn C S L, Schulten V, Taplitz R, Broide D, Hanekom W A, Scriba T J, Wood R, Alam R, Peters B, Sidney J, Sette A. A strategy to determine HLA class II restriction broadly covering the DR, DP, and DQ allelic variants most commonly expressed in the general population. Immunogenetics. 2013 May; 65(5):357-370. PMCID: PMC3633633
55. Shet A, Kaplan E L. Clinical use and interpretation of group A streptococcal antibody tests: a practical approach for the pediatrician or primary care physician. Pediatr Infect Dis J. 2002 May; 21(5):420-6-quiz 427-30. PMID: 12150180
56. Mascini E M, Jansze M, Schellekens J F, Musser J M, Faber J A, Verhoef-Verhage L A, Schouls L, van Leeuwen W J, Verhoef J, van Dijk H. Invasive group A streptococcal disease in the Netherlands: evidence for a protective role of anti-exotoxin A antibodies. J INFECT DIS. 2000 February; 181(2):631-638. PMID: 10669348
57. Abe J, Forrester J, Nakahara T, Lafferty J A, Kotzin B L, Leung D Y. Selective stimulation of human T cells with streptococcal erythrogenic toxins A and B. The Journal of Immunology. 1991 Jun. 1; 146(11):3747-3750. PMID: 1903412
58. Spaulding A R, Salgado-Pabon W, Kohler P L, Horswill A R, Leung D Y M, Schlievert P M. Staphylococcal and Streptococcal Superantigen Exotoxins. Clinical Microbiology Reviews. 2013 Jul. 3; 26(3):422-447.
59. Norrby-Teglund A, Kaul R, Low D E, Mcgeer A, Andersson J, Andersson U, Kotb M. Evidence for the presence of streptococcal-superantigen-neutralizing antibodies in normal polyspecific immunoglobulin G. Infection and Immunity. American Society for Microbiology (ASM); 1996 December; 64(12):5395-5398. PMCID: PMC174535
60. Reglinski M, Sriskandan S. The contribution of group A streptococcal virulence determinants to the pathogenesis of sepsis. Virulence. 2014 Jan. 1; 5(1):127-136. PMCID: PMC3916366
61. Norrby-Teglund A, Low D E, Mcgeer A, Kotb M. Superantigenic activity produced by group A streptococcal isolates is neutralized by plasma from IVIG-treated streptococcal toxic shock syndrome patients. Adv Exp Med Biol. 1997; 418:563-566. PMID: 9331714
62. Norrby-Teglund A, Basma H, Andersson J, Mcgeer A, Low D E, Kotb M. Varying titers of neutralizing antibodies to streptococcal superantigens in different preparations of normal polyspecific immunoglobulin G: implications for therapeutic efficacy. Clinical Infectious Diseases. 1998 March; 26(3):631-638. PMID: 9524835
63. Nooh M M, Nookala S, Kansal R, Kotb M. Individual Genetic Variations Directly Effect Polarization of Cytokine Responses to Superantigens Associated with Streptococcal Sepsis: Implications for Customized Patient Care. The Journal of Immunology. 2011 Feb. 15; 186(5): 3156-3163.
64. Othman A, Al-motarreb A, HA M 3. Human leukocyte antigen class II genetic variants are highly associated with rheumatic heart disease in Yemeni patients. Journal of the Saudi Heart Association. 2013 April; 25(2):126.
65. Kudat H, Telci G, Sozen A B, Oguz F, Akkaya V, Ozcan M, Atilgan D, Carin M, Guven O. The role of HLA molecules in susceptibility to chronic rheumatic heart disease. Int J Immunogenet. Blackwell Science Ltd; 2006 February; 33(1):41-44. PMID: 16426242
66. Querec T D, Akondy R S, Lee E K, Cao W, Nakaya H I, Teuwen D, Pirani A, Gernert K, Deng J, Marzolf B, Kennedy K, Wu H, Bennouna S, Oluoch H, Miller J, Vencio R Z, Mulligan M, Aderem A, Ahmed R, Pulendran B. Systems biology approach predicts immunogenicity of the yellow fever vaccine in humans. Nature Publishing Group. Nature Publishing Group; 2009 January; 10(1): 116-125. PMCID: PMC4049462
67. Cunningham M W, McCormack J M, Fenderson P G, Ho M K, Beachey E H, Dale J B. Human and murine antibodies cross-reactive with streptococcal M protein and myosin recognize the sequence GLN-LYSSER-LYS- GLN in M protein. The Journal of Immunology. 1989 Oct. 15; 143(8):2677-2683. PMID: 2677144
68. Basma H, Norrby-Teglund A, Mcgeer A, Low D E, El-Ahmedy O, Dale J B, Schwartz B, Kotb M. Opsonic antibodies to the surface M protein of group A streptococci in pooled normal immunoglobulins (IVIG): potential impact on the clinical efficacy of WIG therapy for severe invasive group A streptococcal infections. Infection and Immunity. American Society for Microbiology (ASM); 1998 May; 66(5):2279-2283. PMCID: PMC108192
69. Carapetis J R, Steer A C, Mulholland E K, Weber M. The global burden of group A streptococcal diseases. Lancet Infect Dis. 2005 November; 5(11):685-694. PMID: 16253886
70. Bisno A L Group A streptococcal infections and acute rheumatic fever. N Engl J Med. Massachusetts Medical Society; 1991 Sep. 12; 325(11):783-793. PMID: 1870652
71. MD DEM, MD MM, PhD PDSC, PhD PXJ. Rheumatic heart disease. The Lancet. Elsevier Ltd; 2012 Mar. 10; 379(9819):953-964.
72. Ellis N M J, Li Y, Hildebrand W, Fischetti V A, Cunningham M W. T cell mimicry and epitope specificity of cross-reactive T cell clones from rheumatic heart disease. The Journal of Immunology. 2005 Oct. 15; 175 (8):5448-5456. PMID: 16210652
73. Dinkla K, Rohde M, Jansen W T M, Kaplan E L, Chhatwal G S, Talay S R. Rheumatic fever-associated *Streptococcus pyogenes* isolates aggregate collagen. J Clin Invest. 2003 June; 111(12):1905-1912. PMCID: PMC161421
74. Malkiel S, Liao L, Cunningham M W, Diamond B. T-Cell-dependent antibody response to the dominant epitope of streptococcal polysaccharide, N-acetyl-glucosamine, is cross-reactive with cardiac myosin. Infection and Immunity. American Society for Microbiology (ASM); 2000 October; 68(10):5803-5808. PMCID: PMC101540
75. Gorton D, Sikder S, Williams N L, Chilton L, Rush C M, Govan B L, Cunningham M W, Ketheesan N. Repeat exposure to group A streptococcal M protein exacerbates cardiac damage in a rat model of rheumatic heart disease. Autoimmunity. Taylor & Francis; 2016 December; 49(8): 563-570. PMCID: PMC5177596
76. Lauth X, Köckritz-Blickwede von M, McNamara C W, Myskowski S, Zinkernagel A S, Beall B, Ghosh P, Gallo R L, Nizet V. M1 protein allows Group A streptococcal survival in phagocyte extracellular traps through cathelicidin inhibition. J Innate Immun. 2009; 1(3):202-214. PMCID: PMC3241932
77. Oseroff C, Sidney J, Vita R, Tripple V, McKinney D M, Southwood S, Brodie T M, Sallusto F, Grey H, Alam R, Broide D, Greenbaum J A, Kolla R, Peters B, Sette A. T cell responses to known allergen proteins are differently polarized and account for a variable fraction of total response to allergen extracts. J Immunol. American Association of Immunologists; 2012 Aug. 15; 189(4):1800-1811. PMCID: PMC3411923
78. Michon F, Moore S L, Kim J, Blake M S, Auzanneau F-I, Johnston B D, Johnson M A, Pinto B M. Doubly branched hexasaccharide epitope on the cell wall polysaccharide of group A streptococci recognized by human and rabbit antisera. Infection and Immunity. 2005 October; 73(10): 6383-6389. PMCID: PMC1230941
79. Adderson E E, Shikhman A R, Ward K E, Cunningham M W. Molecular analysis of polyreactive monoclonal antibodies from rheumatic carditis: human anti-N-acetyl-glucosamine/anti-myosin antibody V region genes. The Journal of Immunology. 1998 Aug. 15; 161(4):2020-2031. PMID:

The invention claimed is:

1. A method for treatment of a subject for tonsillitis, recurrent tonsillitis, or strep throat, the method comprising:
   processing a biological sample from a subject, wherein the biological sample is a tonsillar tissue or a lymph node tissue sample,
   the sample being suspected of including Granzyme B+germinal center T follicular helper cells (Granzyme B+GC Tfh cells), by measuring an amount of the Granzyme B+GC Tfh cells which are specific for or responsive to Streptococcal pyrogenic exotoxin A (SpeA), and
   comparing the measured amount to a reference amount obtained from a subject without strep throat or tonsillitis, wherein if the measured amount of Granzyme B+GC Tfh cells is greater than the amount in the reference amount it is indicative that the subject has, is at risk of having, or is need of treatment for tonsillitis, recurrent tonsillitis, or strep throat and
   treating the subject if the measured amount of Granzyme B+GC Tfh cells is more than the amount in the reference amount based on the determining step with an agent that decreases the Granzyme B+GC Tfh cells in the subject.

2. The method of claim 1, wherein measuring the Granzyme B+GC Tfh cells specific for or responsive to SpeA is performed using an antigen-specific CD4 T cell activation induced marker (AIM) assay.

3. The method of claim 2, wherein the antigen-specific CD4 T cell AIM assay comprises detecting CD25, Ox40 and PD-L1.

4. The method of claim 1, wherein treating the subject comprises administering a vaccination comprising SpeA, or an SpeA peptide for tonsillitis, recurrent tonsillitis, or strep throat.

5. The method of claim 1, wherein the reference amount is obtained by processing a control sample which is a sample from the subject prior to the treatment, and wherein an increase in the measured amount of Granzyme B+GC Tfh cells compared to the reference amount is indicative that the treatment is effective, or wherein the measuring Granzyme B+GC Tfh cells specific for or responsive to SpeA is performed using an activation induced marker (AIM) assay.

6. The method of claim 1, wherein the method comprises providing an agent for treatment of the subject for tonsillitis, recurrent tonsillitis, or strep throat, wherein the agent is selected from an immunization with SpeA, or an SpeA peptide, or a peptide, protein, recombinant protein, recombinant peptides, antibody, small molecule, ligand mimetic, or a nucleic acid that modulates, reduces, inhibits, decreases or blocks SpeA.

7. A method for evaluating a condition status in a subject, the condition being a disease or disorder associated with impaired germinal centers, the method comprising:
   a. providing a biological sample, wherein the biological sample is a tonsillar tissue or a lymph node tissue sample, from said subject, the sample being suspected of including Granzyme B+germinal center T follicular helper cells (Granzyme B+GC Tfh cells);
   b. processing the sample to determine a concentration, activation, differentiation, proliferation or activity level of said Granzyme B+GC Tfh cells in said sample;
   c. comparing the concentration, activation, differentiation, proliferation or activity level to a reference level obtained from a subject without strep throat, tonsillitis or an autoimmune disease or an average measurement or value gathered from a population of healthy individuals that do not have strep throat, tonsillitis or an autoimmune disease;

d. evaluating the condition status based on at least the comparison in step (c), the condition being associated with impaired germinal centers, wherein the condition status is the disease or disorder associated with impaired germinal centers is tonsillitis, strep throat, recurrent tonsillitis, or the autoimmune disease in the subject based on Granzyme B+GC Tfh cells in said sample compared to the reference level; and e. further comprising treating said subject at least based on said comparison by administering an agent that modulates, increases, enhances, elicits, stimulates, promotes activation, differentiation, proliferation, number or activity of Granzyme B+killer GC Tfh cells, wherein the agent stimulates activation, differentiation, proliferation, number or activity of Granzyme B+killer GC Tfh cells so as to modulate the concentration of said Granzyme B+killer GC Tfh cells in said subject to treat the autoimmune disease.

8. The method of claim 7, further comprising the step of determining response or resistance to treatment for a disease or disorder associated with impaired germinal centers in a subject undergoing treatment for a disease or disorder associated with impaired germinal centers.

9. The method of claim 7, further comprising treating the autoimmune disease, the method comprising administering an agent to said subject for modulating, increasing, enhancing, eliciting, stimulating or promoting activation, differentiation, proliferation, number or activity of Granzyme B+GC Tfh cells.

10. The method of claim 9, further comprising administering to the subject an effective amount of a purified Granzyme B- germinal center T follicular helper cell population sufficient to treat the tonsillitis, strep throat, or recurrent tonsillitis.

11. The method of claim 7, wherein the autoimmune disease is an autoantibody associated autoimmune disease.

12. The method of claim 10, further comprising treating unstimulated GC Tfh cells to have modified gene expression, wherein the modified gene expression comprises expression of Granzyme B and at least one of: increased expression of at least one of: PRDM1 (BLIMP1), decreased expression of BCL1, increased expression of ICOS, increased expression of GZMB, decreased expression of CD28, increased expression of CTLA4, increased expression of EOMES, or increased expression of TBX21 (T-bet), to make Granzyme B+GC Tfh cells.

13. The method of claim 1, wherein treating the subject for tonsillitis, recurrent tonsillitis, or strep throat comprises administering an agent to the subject that: a) increases SpeA specific Granzyme B- germinal center T follicular helper cells, b) increases antibodies against SpeA, c) modulates, reduces, inhibits, decreases or blocks SpeA in an amount sufficient to treat tonsillitis or strep throat in the subject, or d) modulates, reduces, inhibits, decreases or blocks differentiation or activity of the Granzyme B+killer GC Tfh cells.

14. The method of claim 4, wherein the vaccination for tonsillitis or strep throat further comprises an adjuvant.

* * * * *